United States Patent
Wallack et al.

(10) Patent No.: US 12,178,560 B2
(45) Date of Patent: Dec. 31, 2024

(54) EFFICIENT ARTIFICIAL INTELLIGENCE ANALYSIS OF RADIOGRAPHIC IMAGES WITH COMBINED PREDICTIVE MODELING

(71) Applicant: Vetology Innovations, LLC, San Diego, CA (US)

(72) Inventors: Seth Wallack, San Diego, CA (US); Ruben Venegas, San Diego, CA (US); Ariel Ayaviri Omonte, Santa Cruz de la Sierra (BO); Pratheev Sabaratnam Sreetharan, Cambridge, MA (US); Yuan-Ching Spencer Teng, Brøndby Strand (DK)

(73) Assignee: Vetology Innovations, LLC, San Diego, CA (US)

( * ) Notice: Subject to any disclaimer, the term of this patent is extended or adjusted under 35 U.S.C. 154(b) by 806 days.

(21) Appl. No.: 17/134,990

(22) Filed: Dec. 28, 2020

(65) Prior Publication Data
US 2021/0202092 A1 Jul. 1, 2021

Related U.S. Application Data

(63) Continuation of application No. PCT/US2020/066580, filed on Dec. 22, 2020.
(Continued)

(51) Int. Cl.
*A61B 5/055* (2006.01)
*G06T 7/00* (2017.01)
(Continued)

(52) U.S. Cl.
CPC ............ *A61B 5/055* (2013.01); *G06T 7/0012* (2013.01); *G06T 7/11* (2017.01); *G06V 10/763* (2022.01);
(Continued)

(58) Field of Classification Search
CPC ...... A61B 5/055; A61B 5/0077; A61B 5/7264; G06T 7/0012; G06T 7/11;
(Continued)

(56) References Cited

U.S. PATENT DOCUMENTS 9,721,340 B2   8/2017  Gillies et al.
11,494,669 B2 * 11/2022  Hazard .................. G06N 20/00
(Continued)

OTHER PUBLICATIONS

Notification of Transmittal of the International Search Report and the Written Opinion of the International Searching Authority, or the Declaration, PCT/US2020/066582, Mar. 16, 2021, pp. 1-11.

*Primary Examiner* — Lewis G West
(74) *Attorney, Agent, or Firm* — Armis IP Law, LLC

(57) ABSTRACT

A system, an image analyzer and a method for diagnosing a presence of a disease or a condition in an image of a subject, for example, a veterinary patient, are provided including: classifying the image to a body region, and obtaining a classified, labeled, cropped, and oriented sub-image; directing the sub-image to artificial intelligence processor for obtaining an evaluation result, and comparing the evaluation result to a database library of evaluation results and matched written templates or a dataset cluster to obtain at least one cluster result; measuring the distance between the cluster result and the evaluation result to obtain at least one cluster diagnosis; and assembling the cluster diagnosis and the matched written templates to obtain a report to display the report to a radiologist. These system, analyzer and method are achieved in greatly reduced lengths of time and are useful for cost and time savings.

36 Claims, 73 Drawing Sheets

Related U.S. Application Data

(60) Provisional application No. 63/083,422, filed on Sep. 25, 2020, provisional application No. 62/980,669, filed on Feb. 24, 2020, provisional application No. 62/954,046, filed on Dec. 27, 2019.

(51) Int. Cl.
*G06T 7/11* (2017.01)
*G06V 10/762* (2022.01)
*G16H 30/20* (2018.01)
*G16H 50/20* (2018.01)

(52) U.S. Cl.
CPC ............ G16H 30/20 (2018.01); G16H 50/20 (2018.01); *G06T 2207/20132* (2013.01)

(58) Field of Classification Search
CPC . G06T 2207/20132; G06T 2207/10116; G06T 2207/30004; G06V 10/763; G06V 2201/03; G06V 10/70; G16H 30/20; G16H 50/20; G16H 30/40; G16H 50/50; G06F 18/2321; G06F 18/23213; G06N 20/00

See application file for complete search history.

(56) References Cited

U.S. PATENT DOCUMENTS

| | | | |
|---|---|---|---|
| 11,718,322 B2* | 8/2023 | Raichelgauz | G06F 18/23213 701/301 |
| 11,756,655 B2* | 9/2023 | Eltoukhy | G16H 20/00 703/11 |
| 11,842,810 B1* | 12/2023 | Trees | G06Q 10/06395 |
| 2008/0267471 A1* | 10/2008 | Yu | G06T 7/0012 382/128 |
| 2009/0076853 A1 | 3/2009 | Sagawa | |
| 2020/0143279 A1* | 5/2020 | West | G06N 3/08 |
| 2020/0160032 A1* | 5/2020 | Allen | G16H 50/30 |

* cited by examiner

Organ Eval Findings for Lungs

| Code | Name | Ai Eval Type | Category | Actions |
|---|---|---|---|---|
| perihilar_infiltrate 401 | perihilar infiltrate | Perihilar Infiltrate | base | |
| lung_pneumonia 402 | alveolar | Pneumonia | base | |
| bronchial 403 | bronchial | Bronchitis | base | |
| lung_interstitial 404 | interstitial | Interstitial | base | |
| dynamic_airway_disease 405 | dynamic airway | HypoPlastic Trachea | base | |
| pulmonary_nodules 406 | pulmonary nodules | Pulmonary Nodules | base | |
| pleural_effusion 407 | pleural effusion | Pleural Effusion | base | |
| Bronchial_interstitial | | | combined | |
| ... | | | | |

FIG. 4

Findings: Airway/Pulmonary Findings

Finding Config:
Alveolar_Bronchial_Dynamic_Airway_Interstitial_Perihilar_Pleural_Effusion_Pulmonary_Nodules Code: Alveolar_Bronchial_Dynamic_Airway_Interstitial_Perihilar_Pleural_Effusion_Pulmonary_Nodules Base Organ Findings
interstitial
501

Base Organ Findings
bronchial
502

Base Organ Findings
alveolar
503

Base Organ Findings
perihilar infiltrate
504

Base Organ Findings
dynamic airway
505

Base Organ Findings
pulmonary nodules
506

Base Organ Findings
pleural effusion
507

FIG. 5A

Finding Combined Rules

Code:
Severe_Alveolar_Mild_Bronchial_Minimal_Dynamic_Ai
Template MODERATE TO SEVERE INTERSTITIAL
TO ALVEOLAR PATTERN; PULMONARY
NODULES or NODULAR PATTERN; PLEURAL
EFFUSION or PLEURAL FISSURE LINES; MILD
BRONCHITIS; MINIMAL DYNAMIC AIRWAY
DISEASE.
Case Priority: VERY-HIGH
Priority: 7    508

Code:
Mild_Alveolar_Mild_Bronchial_Minimal_Dynamic_Airwa
Template PLEURAL EFFUSION or PLEURAL
FISSURE LINES; PULMONARY NODULES or
NODULAR PATTERN; MILD INTERSTITIAL TO
ALVEOLAR PATTERN; MILD BRONCHITIS;
MINIMAL DYNAMIC AIRWAY DISEASE.
Case Priority: VERY-HIGH
Priority: 7    509

Code:
Moderate_Alveolar_Mild_Bronchial_Minimal_Dynamic_
Template PLEURAL EFFUSION or PLEURAL
FISSURE LINES; PULMONARY NODULES or
NODULAR PATTERN; MILD INTERSTITIAL TO
ALVEOLAR PATTERN; MILD BRONCHITIS;
MINIMAL DYNAMIC AIRWAY DISEASE.
Case Priority: VERY-HIGH
Priority: 7    510

Code:
Severe_Alveolar_Moderate_Bronchial_Minimal_Dynamic_A
Template PULMONARY NODULES or NODULAR
PATTERN; PLEURAL EFFUSION or PLEURAL
FISSURE LINES; SEVERE INTERSTITIAL TO
ALVEOLAR PATTERN; MODERATE BRONCHIAL
PATTERN; DYNAMIC AIRWAY DISEASE.
Case Priority: VERY-HIGH
Priority: 7    511

FIG. 5B

Code:
Severe_Alveolar_Moderate_Bronchial_Mild_Dynamic_A COPY
Template MODERATE to SEVERE INTERSTITIAL TO ALVEOLAR PATTERN; PLEURAL FISSURE LINES or PLEURAL EFFUSION; MODERATE BRONCHIAL PATTERN; MILD DYNAMIC AIRWAY DISEASE; PULMONARY NODULE OR FEW NODULES.
Case Priority: VERY-HIGH
Priority: 7      512

Code:
Severe_Alveolar_Moderate_Bronchial_Mild_Dynamic_A
Template PULMONARY NODULES or NODULAR PATTERN; PLEURAL EFFUSION or PLEURAL FISSURE LINES; SEVERE INTERSTITIAL TO ALVEOLAR PATTERN; MODERATE BRONCHIAL PATTERN; DYNAMIC AIRWAY DISEASE.
Case Priority: VERY-HIGH
Priority: 7      513

Code:
Moderate_Alveolar_Mild_Bronchial_Mild_Dynamic_Airw
Template PLEURAL EFFUSION or PLEURAL FISSURE LINES; PULMONARY NODULES or NODULAR PATTERN; MODERATE INTERSTITIAL TO ALVEOLAR PATTERN; MILD BRONCHITIS; MILD DYNAMIC AIRWAY DISEASE.
Case Priority: VERY-HIGH
Priority: 7      514

Code:
Severe_Alveolar_Moderate_Bronchial_Minimal_Dynami
Template PULMONARY NODULES or NODULAR PATTERN; PLEURAL EFFUSION or PLEURAL FISSURE LINES; SEVERE INTERSTITIAL TO ALVEOLAR PATTERN; MODERATE BRONCHIAL PATTERN; DYNAMIC AIRWAY DISEASE.
Case Priority: VERY-HIGH
Priority: 7      515

FIG. 5C

Code:
Severe_Alveolar_Mild_Bronchial_Minimal_Dynamic_Air
Template Based on the AI airway/pulmonary findings, the probability of this patient having clinically detectable respiratory signs is VERY HIGH (>75%)
Case Priority: VERY-HIGH
Priority: 7

516

Code:
Mild_Alveolar_Mild_Bronchial_Minimal_Dynamic_Airwa
Template Based on the AI airway/pulmonary findings, the probability of this patient having clinically detectable respiratory signs is VERY HIGH (>75%)
Case Priority: VERY-HIGH
Priority: 7

517

Code:
Moderate_Alveolar_Mild_Bronchial_Minimal_Dynamic_
Template Based on the AI airway/pulmonary findings, the probability of this patient having clinically detectable respiratory signs is VERY HIGH (>75%)
Case Priority: VERY-HIGH
Priority: 7

518

Code:
Severe_Alveolar_Moderate_Bronchial_Mild_Dynamic_A
Template Based on the AI airway/pulmonary findings, the probability of this patient having clinically detectable respiratory signs is VERY HIGH (>75%)
Case Priority: VERY-HIGH
Priority: 7

Code:
Severe_Alveolar_Moderate_Bronchial_Mild_Dynamic_A
Template Based on the AI airway/pulmonary findings, the probability of this patient having clinically detectable respiratory signs is VERY HIGH (>75%)
Case Priority: VERY-HIGH
Priority: 7        520

Code:
Severe_Alveolar_Moderate_Bronchial_Mild_Dynamic_A
Template Based on the AI airway/pulmonary findings, the probability of this patient having clinically detectable respiratory signs is VERY HIGH (>75%)
Case Priority: VERY-HIGH
Priority: 7        521

Code:
Moderate_Alveolar_Mild_Bronchial_Mild_Dynamic_Airw
Template Based on the AI airway/pulmonary findings, the probability of this patient having clinically detectable respiratory signs is VERY HIGH (>75%)
Case Priority: VERY-HIGH
Priority: 7        522

Code:
Severe_Alveolar_Moderate_Bronchial_Minimal_Dynami
Template Based on the AI airway/pulmonary findings, the probability of this patient having clinically detectable respiratory signs is VERY HIGH (>75%)
Case Priority: VERY-HIGH
Priority: 7        523

FIG. 5E

Code:
Severe_Alveolar_Mild_Bronchial_Minimal_Dynamic_Air
_3
Template The evaluation has detected soft tissue
pulmonary nodules.
Case Priority: VERY-HIGH
Priority: 7

524

Code:
Mild_Alveolar_Mild_Bronchial_Minimal_Dynamic_Airwa
Template The evaluation has detected pleural fluid
and a soft tissue pulmonary nodule, a few nodules or
mass lesion.
Case Priority: VERY-HIGH
Priority: 7

Code:
Moderate_Alveolar_Mild_Bronchial_Minimal_Dynamic_
Template The evaluation has detected pleural fluid and a soft tissue pulmonary nodule, a few nodules or mass lesion.
Case Priority: VERY-HIGH
Priority: 7

526

Code:
Severe_Alveolar_Moderate_Bronchial_Mild_Dynamic_
_3
Template The evaluation has detected soft tissue pulmonary nodules and pleural fluid.
Case Priority: VERY-HIGH
Priority: 7

527

Code:
Severe_Alveolar_Moderate_Bronchial_Mild_Dynamic_
Template The evaluation has detected pleural fluid and a pulmonary nodular pattern.
Case Priority: VERY-HIGH
Priority: 7

528

Code:
Severe_Alveolar_Moderate_Bronchial_Mild_Dynamic_
_3
Template The evaluation has detected soft tissue pulmonary nodules and pleural fluid.
Case Priority: VERY-HIGH
Priority: 7

Code:
Moderate_Alveolar_Mild_Bronchial_Mild_Dynamic_Airw
Template The evaluation has detected pleural fluid and a soft tissue pulmonary nodule, a few nodules or mass lesion.
Case Priority: VERY-HIGH
Priority: 7   530

Code:
Severe_Alveolar_Moderate_Bronchial_Minimal_Dynam
3
Template The evaluation has detected soft tissue pulmonary nodules and pleural fluid.
Case Priority: VERY-HIGH
Priority: 7   531

Code:
Severe_Alveolar_Mild_Bronchial_Minimal_Dynamic_Air
Template In the PRESENCE of respiratory signs in a dog < 7 years of age, aspiration or bacterial pneumonia, pneumonitis (allergic or parasitic (including heartworm pathosis) would be likely.
Case Priority: VERY-HIGH
Priority: 7   532

Code:
Mild_Alveolar_Mild_Bronchial_Minimal_Dynamic_Airwa
Template In the PRESENCE of respiratory signs in a dog < 7 years of age, aspiration or bacterial pneumonia, pneumonitis (allergic or parasitic (including heartworm pathosis) would be likely.
Case Priority: VERY-HIGH
Priority: 7   533

FIG. 5H

Code:
Moderate_Alveolar_Mild_Bronchial_Minimal_Dynamic_
Template In older dogs, a pulmonary mass or pulmonary nodules, pulmonary hemorrhage, pleural effusion or PTE are primary considerations.
Case Priority: VERY-HIGH
Priority: 7

534

Code:
Severe_Alveolar_Moderate_Bronchial_Mild_Dynamic_
Template In older dogs, a pulmonary mass or pulmonary nodules, pulmonary hemorrhage, pleural effusion or PTE are primary considerations.
Case Priority: VERY-HIGH
Priority: 7

Code:
Severe_Alveolar_Moderate_Bronchial_Mild_Dynamic_A
5
Template In the PRESENCE of respiratory signs in a dog < 7 years of age, aspiration or bacterial pneumonia, pneumonitis (allergic or parasitic (including heartworm pathosis) would be likely.
Case Priority: VERY-HIGH
Priority: 7
536

Code:
Severe_Alveolar_Moderate_Bronchial_Mild_Dynamic_A
5
Template In the ABSENCE of respiratory signs, lung lobe collapse or severe atelectasis secondary to anesthesia or deep sedation could artifactually create this appearance.
Case Priority: VERY-HIGH
Priority: 7
537

Code:
Moderate_Alveolar_Mild_Bronchial_Mild_Dynamic_Airw
Template In the ABSENCE of respiratory signs, lung lobe collapse or severe atelectasis secondary to anesthesia or deep sedation could artifactually create this appearance.
Case Priority: VERY-HIGH
Priority: 7
538

Code:
Severe_Alveolar_Moderate_Bronchial_Minimal_Dynami
5
Template In the ABSENCE of respiratory signs, lung lobe collapse or severe atelectasis secondary to anesthesia or deep sedation could artifactually create this appearance.
Case Priority: VERY-HIGH
Priority: 7
539

FIG. 5J

FIG. 5K

Code: 544

Moderate_Alveolar_Mild_Bronchial_Mild_Dynamic_Airw

Template If this AI evaluation is inconsistent with your assessment or the clinical picture, a Vetology AI overread may be beneficial.
Case Priority: VERY-HIGH

Code: 545

Severe_Alveolar_Moderate_Bronchial_Minimal_Dynam

Template If this AI evaluation is inconsistent with your assessment or the clinical picture, a Vetology AI overread may be beneficial.
Case Priority: VERY-HIGH

FIG. 5L

Code:
Severe_Alveolar_Moderate_Bronchial_Mild_Dynamic_A
Template Given this combination of above thoracic findings, a radiologist over read may be beneficial.
Case Priority: VERY-HIGH
Priority: 7
546

Code:
Severe_Alveolar_Mild_Bronchial_Minimal_Dynamic_Ai
Template MODERATE TO SEVERE INTERSTITIAL TO ALVEOLAR PATTERN; PULMONARY NODULES or NODULAR PATTERN; PLEURAL EFFUSION or PLEURAL FISSURE LINES; MILD BRONCHITIS; MINIMAL DYNAMIC AIRWAY DISEASE.
Case Priority: HIGH
Priority: 7
547

Code:
Severe_Alveolar_Mild_Bronchial_Minimal_Dynamic_Ai
Template Based on the AI airway/pulmonary findings, the probability of this patient having clinically detectable respiratory signs is HIGH (75%)
Case Priority: HIGH
Priority: 7
548

Code:
Severe_Alveolar_Mild_Bronchial_Minimal_Dynamic_Ai 5
Template The evaluation has detected soft tissue pulmonary nodules.
Case Priority: HIGH
Priority: 7
549

FIG. 5M

Code:
Severe_Alveolar_Mild_Bronchial_Minimal_Dynamic_Ai
Template In the PRESENCE of respiratory signs in a dog < 7 years of age, aspiration or bacterial pneumonia, pneumonitis (allergic or parasitic (including heartworm pathosis) would be likely.
Case Priority: HIGH
Priority: 7
550

Code:
Severe_Alveolar_Mild_Bronchial_Minimal_Dynamic_Air
4
Template In the ABSENCE of respiratory signs, lung lobe collapse or severe atelectasis secondary to anesthesia or deep sedation could artifactually create this appearance.
Case Priority: HIGH
Priority: 7
551

Code:
Severe_Alveolar_Mild_Bronchial_Minimal_Dynamic_Ai
Template Minimal dynamic airway disease has been detected.
Case Priority: HIGH
Priority: 7
552

Code:
Severe_Alveolar_Mild_Bronchial_Minimal_Dynamic_Air
Template If this AI evaluation is inconsistent with your assessment or the clinical picture, a Vetology AI overread may be beneficial.
Case Priority: HIGH
Priority: 7
553

FIG. 5N

```
HTTP 200 OK
Allow: GET, HEAD, OPTIONS
Content-Type: application/json
Vary: Accept {
    "vhs": "http://192.168.149.93:8443/vhs/",
    "ai": "http://192.168.149.93:8443/ai/",
    "heart_failure": "http://192.168.149.93:8443/heart_failure/",
    "pneumonia": "http://192.168.149.93:8443/pneumonia/",
    "bronchitis": "http://192.168.149.93:8443/bronchitis/",
    "interstitial": "http://192.168.149.93:8443/interstitial/",
    "diseased_lung": "http://192.168.149.93:8443/diseased_lung/",
    "hypoplastic_trachea": "http://192.168.149.93:8443/hypoplastic_trachea/",
    "cardiomegaly": "http://192.168.149.93:8443/cardiomegaly/",
    "pulmonary_nodules": "http://192.168.149.93:8443/pulmonary_nodules/",
    "pleural_effusion": "http://192.168.149.93:8443/pleural_effusion/",
    "dog_clr": "http://192.168.149.93:8443/dog_clr/",
    "feline_clr": "http://192.168.149.93:8443/feline_clr/",
    "gastritis": "http://192.168.149.93:8443/gastritis/",
    ...
```

FIG. 6

```
{
    "id": 22,
    "img": "http://192.168.149.93:8443/media/bronchitis/67aca9bc845c4e11abced81d8b67d4cd.jpg",
    "heatmap": "http://192.168.149.93:8443/media/bronchitis/67aca9bc845c4e11abced81d8b67d4cd_heatmap.jpg",
    "view": "lateral",
    "label": "Normal",
    "probability": 0.6745642423362976,
    "tag": "prod"
},
{
    "id": 23,
    "img": "http://192.168.149.93:8443/media/bronchitis/55bc975c38ed4e8d940c075b25fe6f1c.jpg",
    "heatmap": "http://192.168.149.93:8443/media/bronchitis/55bc975c38ed4e8d940c075b25fe6f1c_heatmap.jpg",
    "view": "lateral",
    "label": "Abnormal",
    "probability": 0.6156090392303347,
    "tag": "prod"
},
{
    "id": 24,
    "img": "http://192.168.149.93:8443/media/bronchitis/3e02a48ab0db4603a6edad17eb4fdd04.jpg",
    "heatmap": "http://192.168.149.93:8443/media/bronchitis/3e02a48ab0db4603a6edad17eb4fdd04_heatmap.jpg",
    "view": "vd",
    "label": "Normal",
    "probability": 0.7173665165380118,
    "tag": "prod"
},
...
```

FIG. 8

Started At:
2020-05-31 21:20:51

Finished At:
2020-05-31 21:23:24

901

"2020-05-31T21:20:51.090518+00:00",
"2020-05-31T21:23:23.862204+00:00",
"2020-05-31T21:23:23.865251+00:00",
"2020-05-31T21:23:24.077730+00:00",
"2020-05-31T21:23:24.718757+00:00"

AI Specie Log

V2 Case Specie: Unknown
AI Image specie for image 1258883466851: Dog (0.6414720416069)
AI Case Specie: Canine (0.6414720416069)
Acceptance Threshold: 0.15
Overwrite Threshold: 0.15
Final Evaluated Species: Canine

Body Part Screening Eval

Vetology AI Rapid Cardiopulmonary Evaluation

{
  "code": "pulmonary_osteomas"
}

Organ Specific Evaluation

Heart

Lungs

{
  "id": 190513,
  "created_at": "2020-05-31 21:23:32",
  "updated_at": "2020-05-31 21:23:32",

FIG. 9A

Case Eval Type Evaluation

Perihilar Infiltrate

{
"label": "Normal",
"probability": 0.6556207673454285
}
———— 902

[
"2020-05-31T21:23:23.928857+00:00"
]

Pneumonia

{
"label": "Normal",
"probability": 0.7955293278111948
}
———— 904

[
"2020-05-31T21:23:23.936606+00:00"
]

Bronchitis

{
"label": "Normal",
"probability": 0.6211781632237244
}

[
"2020-05-31T21:23:23.950483+00:00"
]

Interstitial

{
"label": "Normal",
"probability": 0.5601854324340082
}

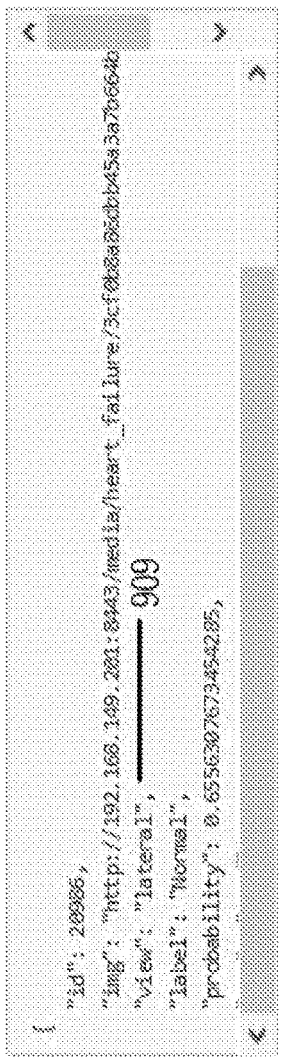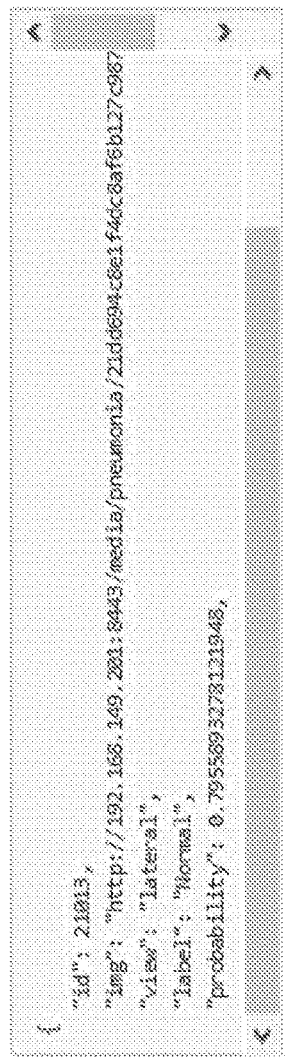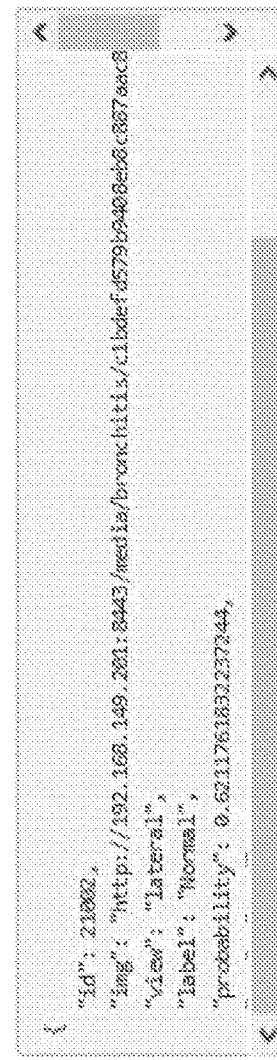
FIG. 9D

```
Organ Specific Evaluation Json Case ID: 1504307
[
  {
    "id" : 404558,
    "ai_eval_type_id" = 2,
    "ai_case_eval_id" = 208001,
    "result" = {
      "label" = "normal",
      "probability" = 0.6540343287852411
    },
    "partial_results" = null,
    "log" = [
      "2020-05-28T17:08:24.843338-00:00 > AI Case Perihilar
    ],
    "started_at" = "2020-05-28 17:08:24",
    "finished_at" = "2020-05-28 17:08:24",
    "created_at" = "2020-05-28 17:08:24",
    "updated_at" = "2020-05-28 17:08:24",
    "ai_eval_type" = {
      "id" = 1,
      "name" = "perihilar infiltrate",
      "code" = "perihilar_infiltrate",
      "created_at" = "2018-12-27 18:25:28",
      "updated_at" = null,
      "enabled" = true,
```

FIG. 10

| case_id | perihilar_infiltrate | pneumonia | bronchitis | interstitial | diseased_lungs | hypo_plastic_trachea | cardiomegaly | pulmonary_nodules | pleural_effusion | ... |
|---|---|---|---|---|---|---|---|---|---|---|
| 1494474 | 0.333914 | 0.39642 | 0.237695 | 0.281116 | 0.238178 | 0.22276 | 0.070676 | 0.308683 | 0.196377 | ... |
| 1494473 | 0.455546 | 0.505307 | 0.252694 | 0.367649 | 0.451428 | 0.427483 | 0.397948 | 0.100435 | 0.415581 | ... |
| 1494472 | 0.333914 | 0.39642 | 0.237695 | 0.281116 | 0.238178 | 0.22276 | 0.070676 | 0.308683 | 0.196377 | ... |
| 1494470 | 0.384345 | 0.624489 | 0.610528 | 0.510519 | 0.695193 | 0.174614 | 0.054147 | 0.751004 | 0.62115 | ... |
| 1494471 | 0.433104 | 0.981548 | 0.820927 | 0.886503 | 0.966835 | 0.950579 | 0.997265 | 0.840377 | 0.997095 | ... |
| 1494469 | 0.494026 | 0.85793 | 0.329557 | 0.392661 | 0.280339 | 0.270056 | 0.026974 | 0.019649 | 0.547702 | ... |
| 1494452 | 0.344261 | 0.989305 | 0.3145 | 0.819 | 0.784475 | 0.460203 | 0.152565 | 0.514604 | 0.349647 | ... |
| 1494463 | 0.870427 | 0.775081 | 0.908024 | 0.893298 | 0.940675 | 0.781937 | 0.991577 | 0.743715 | 0.897896 | ... |
| 1494453 | 0.502589 | 0.917159 | 0.270194 | 0.595008 | 0.351601 | 0.18943 | 0.259505 | 0.046976 | 0.48746 | ... |
| 1494454 | 0.106133 | 0.444564 | 0.141481 | 0.223801 | 0.120926 | 0.322191 | 0.006671 | 0.019114 | 0.080124 | ... |
| 1494456 | 0.285027 | 0.225674 | 0.254145 | 0.345074 | 0.274006 | 0.299289 | 0.010647 | 0.011645 | 0.180383 | ... |
| 1494457 | 0.436355 | 0.847291 | 0.939316 | 0.849704 | 0.958877 | 0.907486 | 0.987323 | 0.732015 | 0.928844 | ... |
| 1494460 | 0.246364 | 0.64014 | 0.494485 | 0.494849 | 0.592864 | 0.561506 | 0.590078 | 0.152525 | 0.489386 | ... |
| 1494449 | 0.820403 | 0.936119 | 0.979869 | 0.952452 | 0.991972 | 0.910322 | 0.927216 | 0.997826 | 0.988489 | ... |
| 1494447 | 0.675039 | 0.67249 | 0.762049 | 0.705719 | 0.728959 | 0.480946 | 0.406918 | 0.76759 | 0.745071 | ... |
| 1494448 | 0.261456 | 0.649615 | 0.266807 | 0.378916 | 0.486878 | 0.276155 | 0.110669 | 0.285894 | 0.143016 | ... |
| 1494445 | 0.820403 | 0.936119 | 0.979869 | 0.952452 | 0.991972 | 0.910322 | 0.927216 | 0.997826 | 0.988489 | ... |
| ... | ... | ... | ... | ... | ... | ... | ... | ... | ... | ... |

FIG. 12A

| | 1203 | | | | 1204 |
|---|---|---|---|---|---|
| label | embeddi ng_x | embeddi ng_y | centroid_ embeddi ng_x | centroid_ embeddi ng_y | centroid_ caseid |
| 43 | -9.0274 | -32.0377 | -6.95176 | -32.4319 | 1494474 |
| 25 | 20.0796 | -8.63867 | 21.12844 | -9.60563 | 1491954 |
| 43 | -9.0274 | -32.0377 | -6.95176 | -32.4319 | 1494474 |
| 122 | -9.93983 | 6.279617 | -9.52419 | 7.988142 | 1494470 |
| 26 | -6.79981 | 53.30278 | -5.89616 | 52.43982 | 1487444 |
| 1 | 26.82523 | -24.6248 | 26.87982 | -22.7032 | 1493129 |
| 74 | 7.56528 | 13.09128 | 8.247137 | 9.308992 | 1489605 |
| 40 | -1.41839 | 53.82275 | -2.22823 | 53.4397 | 1494463 |
| 1 | 26.8911 | -23.6762 | 26.87982 | -22.7032 | 1493129 |
| 89 | 17.0323 | -42.3759 | 15.76051 | -41.5215 | 1494149 |
| 16 | 9.361856 | -37.2028 | 5.264326 | -40.6652 | 1491427 |
| 166 | -8.47965 | 52.58028 | -9.48024 | 52.46748 | 1494457 |
| 56 | 13.51117 | -3.60323 | 13.606687 | -2.17455 | 1486703 |
| 90 | 7.941667 | 55.33223 | 6.815841 | 55.77559 | 1484763 |
| 78 | -1.06159 | 23.28821 | -3.45683 | 21.00824 | 1494447 |
| 38 | 18.5095 | -25.4157 | 16.128885 | -22.5868 | 1494448 |
| 90 | 7.699446 | 54.71375 | 6.815841 | 55.77559 | 1484763 |
| ... | ... | ... | ... | ... | ... |

FIG. 12B

Ai Cluster Models

| ID | Name | # Clusters | Body Part | Started At | Finished At | Actions |
|---|---|---|---|---|---|---|
| 32 | test_info_thorax_cluste ring<br>test_info_thorax_clustering | 5 | thorax | 2020-09-23 05:13:42 | 2020-09-23 05:15:31 | |
| 31 | Thorax Clustering 1<br>Antuan_thorax_clustering_1 | 50 | thorax | 2020-09-16 22:36:24 | 2020-09-16 22:40:45 | |
| 30 | Thorax 97<br>thorax_97 | 97 | thorax | 2020-09-11 12:48:28 | 2020-09-14 16:59:32 | |
| 29 | Thorax Test min<br>thorax_test_min | 10 | thorax | 2020-09-11 12:32:52 | 2020-09-11 12:34:16 | |
| 28 | Seth Abomen 97<br>seth_abomen_97 | 97 | abdomen | 2020-09-03 14:41:13 | 2020-09-07 22:43:33 | |

Screening Evaluation Config

| ID | Name | Code | Title | Body Region | Cluster Model | Status | Created At |
|---|---|---|---|---|---|---|---|
| 1 | Veotogy AI Rapid Cardiopulmonary Evaluation-Current | thorax_screening | CAMNE AI Cardiopulmonary Screening | thorax | Thorax Clustering 1 Disabled | | 2019-02-20 10:01:47 | Actions ▼ |
| 2 | Veotogy AI Abdomen Screening | abdomen_screeni ng | AI Abdomen Screening | abdomen | Seth Abdomen 97 Enabled | | 2020-06-16 07:05:16 | Actions ▼ |
| 3 | example | example_code | None | thorax | Thorax clustering with new models Enabled | | 2020-07-02 15:26:41 | Actions ▼ |

FIG. 15

Cluster Model Logs

Cluster model build logs- Item 7 from AI cluster model details for Thorax 97

```
[
"2020-09-11T12:48:28.725513+00:00 > ==== Starting Async Process",
"2020-09-11T12:48:28.938134+00:00 > ==== SendDataforClustering",
"2020-09-11T12:48:28.944826+00:00 > Parameters to get all the cases",
"2020-09-11T12:48:58.889188+00:00 > Sending Data to AI Clustering API",
"2020-09-11T12:48:58.893843+00:00 > Requesting Token to AI API",
"2020-09-11T12:48:59.047888+00:00 > Token generated.",
"2020-09-11T12:48:59.117256+00:00 > Sending cluster model to: http://192.168.149.93:8443
"2020-09-11T12:48:59.224458+00:00 > {\"id\":137,\"tag\":\"thorax_97\",\"features\":[\"br
"2020-09-11T12:48:59.224707+00:00 > CSV Data Sent for Clustering",
"2020-09-11T12:49:02.149403+00:00 > ==== Checking if Clusters for Cluster Model: thorax
"2020-09-11T12:49:02.169088+00:00 > Requesting Token to AI API",
"2020-09-11T12:49:02.447958+00:00 > Token generated.",
"2020-09-11T12:49:02.448163+00:00 > Get cluster model to: http://192.168.149.93:8443//cl
"2020-09-11T12:49:02.486720+00:00 > {\"id\":137,\"tag\":\"thorax_97\",\"features\":[\"br
"2020-09-11T12:50:01.744496+00:00 > ==== Checking if Clusters for Cluster Model: thorax
"2020-09-11T12:50:01.756478+00:00 > Requesting Token to AI API",
"2020-09-11T12:50:01.946116+00:00 > Token generated.",
"2020-09-11T12:50:01.946434+00:00 > Get cluster model to: http://192.168.149.93:8443//cl
"2020-09-11T12:50:01.999583+00:00 > {\"id\":137,\"tag\":\"thorax_97\",\"features\":[\"br
"2020-09-11T12:50:02.000512+00:00 > ==== Starting Importing Clusters from AI",
"2020-09-11T12:50:02.035910+00:00 > Creating AI clusters in DB",
"2020-09-11T12:50:02.906783+00:00 > Requesting Data from AI server",
```

Close

FIG. 16B

Evaluation Models Config

Add New Entry

| ID | Name | Code | Status | Body Region | |
|----|------|------|--------|-------------|---|
| 1 | Vertebral Heart Score | vhs | | thorax | Actions ▼ |
| 2 | Perihilar infiltrate | perihilar_infiltrate | | thorax | Actions ▼ |
| 3 | Pneumonia | pneumonia | | thorax | Actions ▼ |
| 4 | Bronchitis | bronchitis | | thorax | Actions ▼ |

AI Eval Tester

Success AI Results

Perihilar Infiltrate
Label: Abnormal
Probability: 0.7884457111358843

Pneumonia
Label: Abnormal
Probability: 0.7685036800403618

Bronchitis
Label: Abnormal
Probability: 0.6527054889669418

Interstitial
Label: Abnormal
Probability: 0.7859766930341721

Diseased Lungs
Label: Abnormal
Probability: 0.8071300536394119

HypoPlastic Trachea
Label: Abnormal
Probability: 0.6790897101163864

Cardiomegaly
Label: Abnormal
Probability: 0.9989846497774124

Pulmonary Nodules
Label: Abnormal
Probability: 0.5190156655146645

Pleural Effusion
Label: Abnormal
Probability: 0.9480154067277908

Gastritis
Label: Normal
Probability: 0.8872566592512307

Ascites
Label: Normal
Probability: 0.8921146243810634

Colitis
Label: Normal
Probability: 0.9621179401874542

Body Part Screening Result

Abdomen AI Screening v2

```
{
  "code": "clustering_result"
}
```

Conclusion

No definitive abdominal abnormalities are appreciated. Gastroenteritis is suspected. There is no evidence of small bowel obstruction. This is of doubtful clinical significance at this time. Gastric contents may represent residual ingesta and administered medications.

← 1801

Evaluation findings finding_testA

1) A ventral dorsal and both lateral radiographs of the abdomen are provided.
2) There is no effusion.
3) The stomach contains a moderate amount of soft tissue opacity that is stippled with gas.
4) A few punctate mineral densities are also present within the stomach.
5) Small intestines are minimally filled.

AiCluster Tag :

Ranking Sentences

Scope: All

| ID | Sentence | Ranking | Scope | Started At |
|---|---|---|---|---|
| 72841 | Large soft tissue opacity mass effect in the caudal thorax. | 1 | conclusion ← 1806 | 1 sentence 2020-09-14 16:58:50 |
| 72834 | Orthogonal radiographs of the thorax are submitted for review. | 1 | finding ← 1807 | 1 sentence 2020-09-14 16:58:50 |
| 72845 | Further imaging is needed. | 1 | recommendation ← 1808 | 1 sentence 2020-09-14 16:58:51 |
| 72842 | The primary differential is neoplasia associated with the accessory lung lobe. | 2 | conclusion | 1 sentence 2020-09-14 16:58:50 |

Read Finalized: 04/24/2020 12:35　　　　Page 1 of 2　　　　Read Finalized: 04/24/2020 12:35

FULL REPORT Radu Index

Case
ID  1493684
DOS  04/23/2020
Priority  Normal

Clinic

Patient
Name:
Current Age:
Age when report:
Sex:
Species: canine
Breed: labrador
Weight: 41.80 lb

Clinic Doctor

Consultant

History

Chronic non productive cough, eating/drinking WNL. Blood work sent to the lab, Heart worm test-negative

Findings

Three good-quality orthogonal thoracic radiographs dated _____ are available for review. There are no previous radiographs available for comparison.

Airway findings: The trachea, tracheal bifurcation and carina are normal. There is a moderate mainly bronchointerstitial pattern. The worst affected region as the right caudal along low. No masses or nodules are seen.

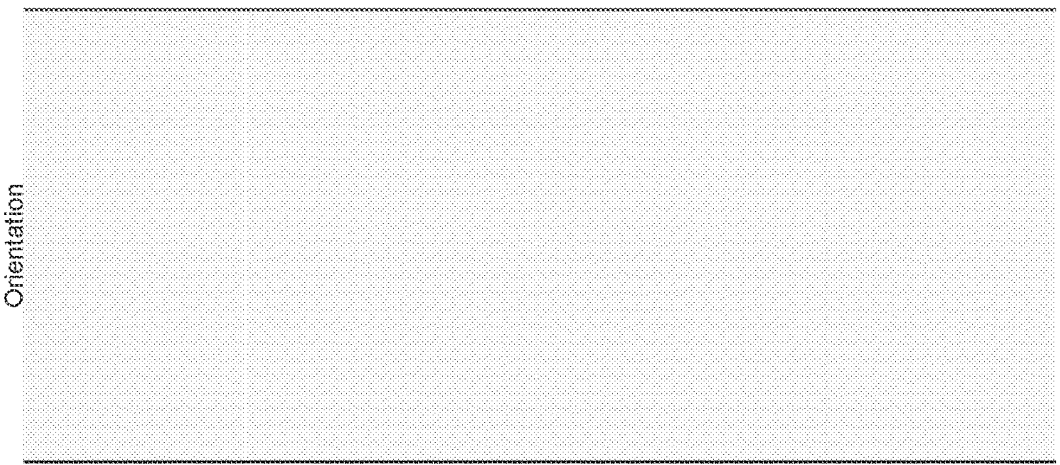
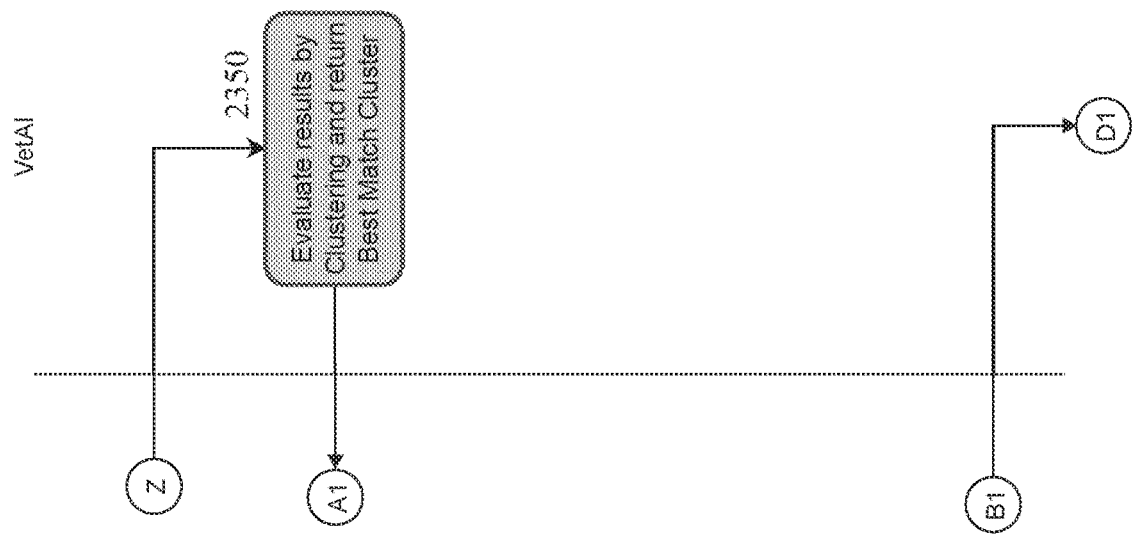
FIG. 23Q

EFFICIENT ARTIFICIAL INTELLIGENCE ANALYSIS OF RADIOGRAPHIC IMAGES WITH COMBINED PREDICTIVE MODELING

RELATED APPLICATION

This application is a continuation of International application PCT/US20/66580 filed Dec. 22, 2020 entitled "Efficient artificial intelligence analysis of radiographic images with combined predictive modeling" by inventors Seth Wallack, Ariel Ayaviri Omonte, Ruben Venegas, Yuan-Ching Spencer Teng and Pratheev Sabaratnam Sreetharan which claims the benefit of and priority to U.S. provisional applications Ser. No. 62/954,046 filed Dec. 27, 2019 and to 62/980,669 filed Feb. 24, 2020, both entitled "Efficient Artificial Intelligence Analysis of Radiographic Images" by inventors Seth Wallack, Ariel Ayaviri Omonte and Ruben Venegas; and U.S. provisional application Ser. No. 63/083,422 filed Sep. 25, 2020 entitled "Efficient artificial intelligence analysis of radiographic images with combined predictive modeling" by inventors Seth Wallack, Ariel Ayaviri Omonte, Ruben Venegas, Yuan-Ching Spencer Teng and Pratheev Sabaratnam Sreetharan, each of which is hereby incorporated by reference herein in its entirety.

BACKGROUND

Artificial intelligence (AI) processors, e.g., trained neural networks are useful to process radiographic images of animals to determine probabilities that the imaged animals have certain conditions. Typically, separate AI processors are used to evaluate respective body regions (e.g., thorax, abdomen, shoulder, fore limbs, hind limbs, etc.) and/or particular orientations (e.g., ventral dorsal (VD) view, lateral view, etc.) of each such body region. A specific AI processor determines for a respective body region and/or orientation, probabilities that particular conditions exist with respect to the body region in question. Each such AI processor includes a large number of trained models to evaluate respective conditions or organs within the imaged region. For example, with respect to a lateral view of an animal's thorax, an AI processor employs different models to determine probabilities that the animal has certain conditions relating to the lungs, such as perihilar infiltrate, pneumonia, bronchitis, pulmonary nodules, etc.

The amount of processing that is performed by each such AI processor, and the amount of time that is needed to complete such processing is extensive. The task either requires (1) a manual identification and cropping of each image to define a particular body region and orientation prior to the image being evaluated by a specific AI processor or (2) feeding the images into each AI processor for evaluation. Unlike human radiology in which radiographic studies are limited to specific areas, veterinary radiology routinely includes multiple unlabeled images, with multiple body regions of unknown orientation, within a single study.

In a conventional workflow for processing a radiographic image of an animal, the system assumes that a user-identified body region is contained in the image. The user-identified image is then sent to specific AI processors that, for example, use machine learning models to evaluate the probability of the presence of a medical condition for that specific body region. However, requiring the user to identify body region creates friction in the conventional workflow and leads to errors if the identified body region is incorrect or if multiple regions are contained in the image. Additionally, the conventional workflow becomes inefficient (or breaks down) when images without user identification of body region are sent to the system. When this occurs, the conventional workflow is inefficient because unidentified images are sent to a large number of AI processors which are not specific to the imaged body region. Further, the conventional workflow is prone to false results because incorrect region identification results in images being sent to AI processors that are configured to evaluate different body regions.

The conventional workflow for analyzing diagnostic features of a radiograph using AI and preparing a report based on AI model diagnostic results in an exponential number of possible output reports. An AI model diagnostic result provides either a normal or an abnormal determination with respect to a particular condition. In some AI models, a determination of the severity of a particular condition e.g. normal, minimal, mild, moderate, or severe, is also provided. A collection of AI model diagnostic results determine which report is to be selected from premade report templates. The process of creating and choosing a single report template from a collection of AI model diagnostic results scales exponentially with the number of AI models. Six different AI model normal/abnormal diagnostic results require 64 different report templates (two raised to the sixth power). Ten models require 1,024 templates, and 16 models require 65,536 templates. AI models that detect severity scale even more poorly, for example 16 severity detection models with 5 possible severities each would require over 150 billion templates. Therefore, a manually created report for each combination of AI model diagnostic results does not scale well to a large number of AI models being interpreted together.

Therefore, there exists a need for a novel system which has several fully automated stages of image preprocessing and image analysis, including determining whether the received image includes a particular body region in a particular orientation (lateral view, etc.); cropping the image appropriately; creating one or more sub-images from an original image that contains more than one body region or region of interest; labeling the original image and any sub-images created; and evaluating the cropped image and sub-images against targeted AI models. Further, there exists a need for a novel system which analyzes and provides a diagnostic radiologist report based on a large number of test results, including but not limited to, AI model results.

SUMMARY

An aspect of the invention described herein provides a method for analyzing a diagnostic radiographic image or an image of a subject, the method including: processing automatically the radiographic image of the subject using a processor for classifying the image to one or more body regions or body regions and orienting and cropping a classified image to obtain at least one oriented, cropped and labeled sub-image for each body region that is automatically classified; directing the sub-image to at least one artificial intelligence processor; and evaluating the sub-image by the artificial intelligence processor thereby analyzing the radiographic image of the subject.

An embodiment of the method further includes using the artificial intelligence processor for assessing the sub-image for body regions and for a presence of a medical condition. Body regions are for example: thorax, abdomen, forelimbs, hindlimbs, etc. An embodiment of the method further includes using the artificial intelligence processor for diagnosing the medical condition from the sub-image. An embodiment of the method further includes using artificial intelligence processor for assessing the sub-image for a positioning of the subject. An embodiment of the method further includes rectifying the positioning of the subject to proper positioning.

In an embodiment of the method, the processor automatically rapidly processing the radiographic image to obtain the sub-image. In an embodiment of the method, the processor processing the radiographic image to obtain the sub-image in: less than about one minute, less than about 30 seconds, less than about 20 seconds, less than about 15 seconds, less than about 10 seconds, or less than about 5 seconds. In an embodiment of the method, evaluating further includes comparing the sub-image to a plurality of reference radiographic images in at least one of a plurality of libraries. In an embodiment of the method, the plurality of libraries each includes a respective plurality of the reference radiographic images.

In an embodiment of the method, each of the plurality of libraries include respective plurality of reference radiographic images specific or non-specific to an animal species. An embodiment of the method further includes matching the sub-image to a reference radiographic image thereby assessing orientation and at least one body region. In an embodiment of the method, the reference radiographic images are oriented in Digital Imaging and Communication in Medicine (DICOM) standard hanging protocol.

In an embodiment of the method, cropping further includes isolating a specific body region in the sub-image. An embodiment of the method further includes categorizing the reference radiographic images according to veterinary radiographic standard body region labels. In an embodiment of the method, orienting further includes adjusting the radiographic image to veterinary radiographic standard hanging protocol. In an embodiment of the method, cropping further includes trimming the radiographic sub-images to a standard aspect ratio. In an alternative embodiment of the method, cropping further does not include trimming the radiographic sub-images to a standard aspect ratio. In an embodiment of the method, classifying further includes identifying and labeling body region according to veterinary standard body region labels. In an embodiment of the method, classifying further includes comparing the radiographic image to a library of sample standard radiographic images.

An embodiment of the method further includes matching the radiographic image to a sample standard image in the library thereby classifying the radiographic image to one or more body regions. In an embodiment of the method, cropping further includes identifying a boundary in the radiographic image delineating each classified body region. An embodiment of the method further includes prior to classifying, extracting a signature of the radiographic image. In an embodiment of the method, the radiographic image is from a radiology exam selected from: radiographs viz., X-ray, magnetic resonance imaging (MRI), magnetic resonance angiography (MRA), computed tomography (CT), fluoroscopy, mammography, nuclear medicine, Positron emission tomography (PET), and ultrasound. In an embodiment of the method, the radiographic image is a photograph.

In an embodiment of the method, the subject is selected from: a mammal, a reptile, a fish, an amphibian, a chordate, and a bird. In an embodiment of the method, the mammal is selected from: dog, cat, rodent, horse, sheep, cow, goat, camel, alpaca, water buffalo, elephant, and human. In an embodiment of the method, the subject is selected from: a pet, a farm animal, a high value zoo animal, a wild animal, and a research animal. An embodiment of the method further includes automatically generating at least one report with evaluation of the sub-image by the artificial intelligence processor.

An aspect of the invention described herein provides a system for analyzing radiographic images of a subject, the system including: a receiver to receive a radiographic image of the subject; at least one processor to automatically run an image identification and processing algorithm to identify, crop, orient and label at least one body region in the image to obtain a sub-image; at least one artificial intelligence processor to evaluate the sub-image; and a device to display the sub-image and evaluated artificial intelligence result.

In an embodiment of the system, the processor automatically rapidly processes the radiographic image to obtain the sub-image. In an embodiment of the system, the processor processes the radiographic image to obtain the labeled image in: less than one minute, less than 30 seconds, less than 20 seconds, less than 15 seconds, less than 10 seconds, or less than 5 seconds. An embodiment of the system further includes a library of standard radiographic images. In an embodiment of the system, the standard radiographic images comply with veterinary norms for hanging protocol and body region labels.

An aspect of the invention described herein provides a method for rapidly and automatically preparing radiographic images of a subject for display, the method including: processing an unprocessed radiographic image of the subject using a processor to algorithmically classify the image to one or more separate body region categories, by automatically cropping, extracting a signature and comparing a cropped, oriented image signature to a database of signatures of images of known orientation and body regions to obtain a best match orientation and body region labeling; and, presenting each prepared body region labeled image on a display device and for analysis.

An aspect of the invention described herein provides an improvement in a veterinary radiograph diagnostic image analyzer, the improvement including running a rapid algorithm with a processor that pre-processes a radiograph image of a subject to automatically identify one or more body regions in the image; the processor further functions to perform at least one of: automatically creating a separate sub-image for each identified body region, cropping and optionally normalizing an aspect ratio of each sub-image created, automatically labeling each sub-image as a body region, automatically orienting the body region in the sub-image, and the processor further automatically directs the diagnostic sub-image to at least one artificial intelligence processor specific for evaluating cropped, oriented and labeled diagnostic sub-image.

An aspect of the invention described herein provides a method for identifying and diagnosing a presence of a disease or a condition in at least one image of a subject, the method including: classifying the image to one or more body regions, labelling and orientating the image to obtain a classified, labeled and oriented sub-image; directing the sub-image to at least one artificial intelligence (AI) processor to obtain an evaluation result, and comparing the evaluation result to a database with evaluation results and matched written templates or at least one dataset cluster to obtain at least one cluster result; measuring the distance between the cluster result and the evaluation result to obtain at least one cluster diagnosis; and assembling the cluster diagnosis to obtain a report thereby identifying and diagnosing the presence of the disease or the condition in the subject. The evaluation result is synonymous with AI result, AI processor result and classification result are used interchangeably.

An embodiment of the method further includes prior to classifying, obtaining at least one radiographic image or one data point of the subject. An embodiment of the method further includes prior to comparing, compiling the dataset cluster using a clustering tool selected from: K-means clustering, Mean shift clustering, Density-Based Spatial Clustering, Expectation-Maximization (EM) Clustering, and Agglomerative Hierarchical Clustering. In an embodiment of the method, compiling further includes obtaining, processing, evaluating, and constructing a library of a plurality of identified and diagnosed dataset and corresponding medical reports selected from: radiology reports, laboratory reports, histology reports, physical exam reports, and microbiology reports, with a plurality of known diseases or conditions.

In an embodiment of the method, processing further includes classifying the plurality of identified and diagnosed dataset images to the body regions to obtain a plurality of classified dataset images, and orienting and cropping the plurality of classified dataset images to obtain a plurality of oriented, cropped and labeled dataset sub-images. In an embodiment of the method, evaluating further includes directing the plurality of oriented, cropped and labeled dataset sub-images and corresponding medical reports to at least one AI processor to obtain at least one diagnosed AI processor result. In an embodiment of the method, directing further includes classifying the plurality of oriented, cropped and labeled dataset sub-images and corresponding medical reports with at least one variable selected from: species, breed, weight, sex, and location.

In an embodiment of the method, constructing the library of the plurality of identified and diagnosed dataset images further includes creating at least one cluster of the diagnosed AI processor result to obtain at least one AI processor exemplar result and thereby compiling the dataset cluster. In some embodiments the AI processor exemplar result is an exemplar case, an exemplar result, an exemplar point, or an exemplar. These terms are synonymous and interchangeably used. An embodiment of the method further includes assigning at least one cluster diagnosis to the cluster of the diagnosed AI processor result. In an embodiment of the method, assigning cluster diagnosis further includes adding reports within the cluster and/or additional information written by an evaluator. In an embodiment of the method, measuring further includes determining a distance between the cluster result and at least one selected from: the evaluation result, the dataset cluster, and a centroid of the cluster result.

An embodiment of the method further includes selecting a result from: a case within the cluster that has the nearest match, a result from another case in the cluster, and a centroid case. In an embodiment of the method selecting further includes adding result information of the cluster result by an evaluator to the report generated from the cluster. An embodiment of the method further includes editing the report by removing a portion of the report of the cluster diagnosis which is less than a threshold of prevalence in a plurality of reports in the cluster. In an embodiment of the method, report is generated from words that are deemed acceptable for use in report generation. The words in the report are obtained from the closest matching exemplar result case or from centroid case. The words that are acceptable for report generation are excluded if the words include at least one identifier selected from: a subject name, date, reference to a prior study, or any other word that could generate a report that was not universally usable for all new cases that match closest to that exemplar result. This selection process is performed by Natural Language Processing (NLP).

In an embodiment of the method, the threshold of prevalence designated by an evaluator, is selected to be less than at about 80%. In an embodiment of the method, rapidly processing the evaluation result by a diagnostic AI processor to obtain the report. In an embodiment of the method, the diagnostic AI processor processing the image to obtain the report in: less than about ten minutes, less than about 9 minutes, less than about 8 minutes, less than about 7 minutes, less than about 6 minutes, less than about 5 minutes, less than about 4 minutes, less than about 3 minutes, less than about 2 minutes, or less than about 1 minute. In an embodiment of the method, the library of identified and diagnosed dataset images with known diseases and conditions are categorized to at least one of a plurality of animal species.

An embodiment of the method further includes identifying the diagnosed AI processor result with an identification tag. An embodiment of the method further includes selecting and adding the image and/or a medical result of the subject to the dataset cluster.

An aspect of the invention described herein provides a system for diagnosing a presence of a disease or a condition in an image and/or a medical result, of a subject, the system including: a receiver to receive an image and/or the medical result of the subject; at least one processor to automatically run an image identification and processing algorithm to identify, crop, orient and label at least one body region in the image to obtain a sub-image; at least one artificial intelligence processor to evaluate the sub-image and/or the medical result and obtain an evaluation result; and at least one diagnostic artificial intelligence processor to automatically run a cluster algorithm to compare the evaluation result to obtain a cluster result, measure distance between cluster result and a previously created cluster result from a specific dataset defined by one or more variables, evaluation result to obtain cluster diagnosis, and assemble a report.

In an embodiment of the method, the diagnostic AI processor automatically rapidly processes the image, and/or the medical result to generate a report. In an embodiment of the method, the diagnostic AI processor processes the image and/or the medical result to obtain the report in: less than about ten minutes, less than about 9 minutes, less than about 8 minutes, less than about 7 minutes, less than about 6 minutes, less than about 5 minutes, less than about 4 minutes, less than about 3 minutes, less than about 2 minutes, or less than about 1 minute. An embodiment of the method further includes a device to display the generated report.

An aspect of the invention described herein provides a method for diagnosing a presence of a disease or a condition in at least one image of a subject, the method including: classifying the image to at least one body region, labelling, cropping, and orientating the image to obtain at least one classified, labeled, cropped, and oriented sub-image; directing the sub-image to at least one artificial intelligence (AI) processor for processing and obtaining an evaluation result, and comparing the evaluation result to a database library having a plurality of evaluation results and a matched written templates or at least one dataset cluster to obtain at least one cluster result; measuring the distance between the cluster result and the evaluation result to obtain at least one cluster diagnosis; and assembling the cluster diagnosis and the matched written templates to obtain a report and displaying the report to a radiologist thereby identifying and diagnosing the presence of the disease or the condition in the subject.

An embodiment of the method further includes after displaying, analyzing the report and confirming the presence of the disease or the condition. An alternative embodiment of the method further includes editing the written templates. In an embodiment of the method, obtaining the report has a process time: less than about 5 minutes, less than about 2 minutes, or less than about 1 minute. In an embodiment of the method, obtaining the report has a process time: less than about 10 minutes, less than about 7 minutes, or less than about 6 minutes.

In an embodiment of the method, processing the sub-image further includes training the AI processor for diagnosing the presence of the disease or the condition in the image of the subject. In an embodiment of the method, training the AI processor further includes: communicating a library of training images to the AI processor; choosing a training image having the disease or the condition from the library of training images; and comparing the training image to the library of training images thereby training the AI processor.

In an embodiment of the method, the library of training images includes positive control training images and negative control training images. In an embodiment of the method, the positive control training images have the disease or the condition of the training image. In an embodiment of the method, the negative control training images do not have the disease or the condition of the training image. In various embodiments of the method, the negative control training images may have diseases or conditions other than the disease or the condition of the training image. In an embodiment of the method, the library of training images further includes at least one of medical data, metadata, and auxiliary data.

Figure 1:
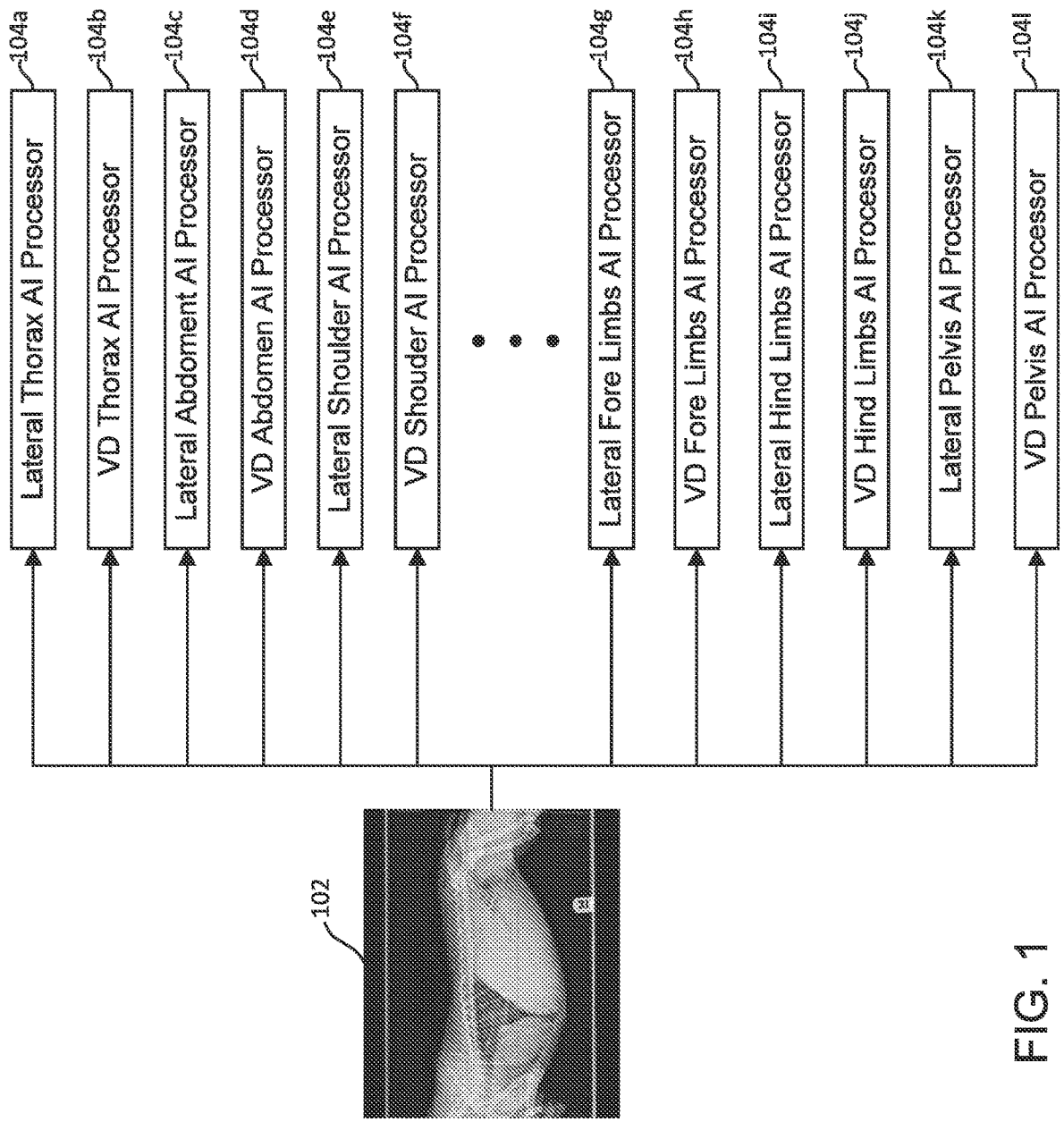
FIG. 1 is a schematic drawing of a conventional workflow for processing a radiographic image 102 of an animal. As commonly represented in the veterinary field, the image 102 does not indicate portion(s) of the animal. The image 102 is processed by each of a large number of AI processors 104a-104l to determine if that body region is present on the image and the probabilities that the animal represented in the image 102 has certain conditions. Each of the AI processors 104a-104l evaluate the image 102 by comparing the image to one or more machine learning models that have each been trained to determine a probability that the animal has a particular condition.
Figure 2:
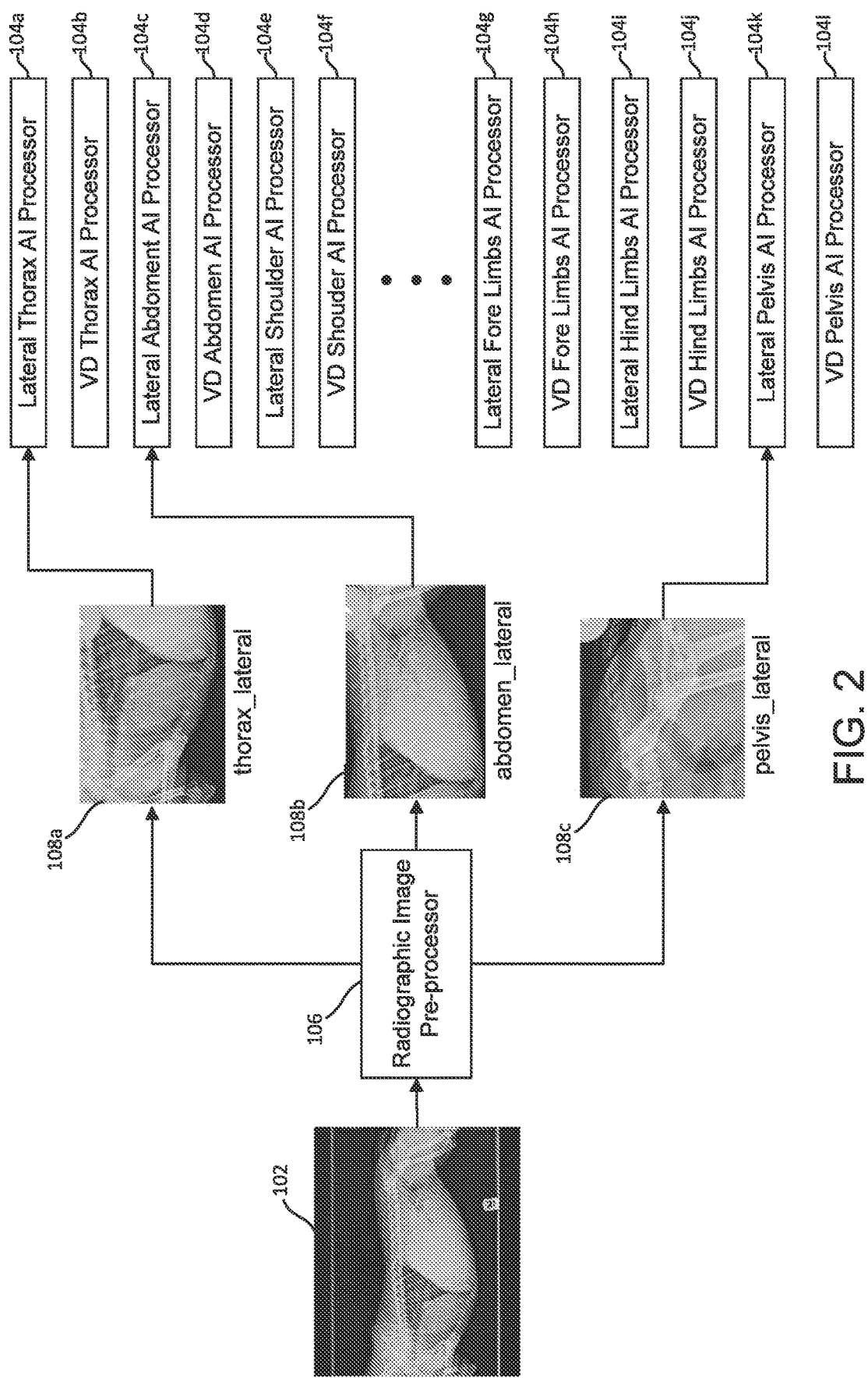
FIG. 2 is a schematic drawing of an embodiment of the system or the methods described herein. A radiographic image pre-processor 106 is deployed to pre-process the image 102 to generate one or more sub-images 108 that each corresponds to a particular view of a specific body region. Three sub-images 108a-c were generated, with one sub-image 108a identified and cropped as a lateral view of a thorax of the animal, second sub-image 108b identified and cropped as a lateral view of the animal's abdomen, and third sub-image 108c identified and cropped as a lateral view of the animal's pelvis.

As indicated, the sub-image 108a is processed only by the lateral thorax AI processor 104a, the sub-image 108b is processed only by the lateral abdomen AI processor 104c, and the sub-image 108c is processed only by the lateral pelvis AI processor 104k. In some embodiments, the sub-images 108 is tagged to identify the body region and/or view that sub-image 108 represents.

Figure 3:
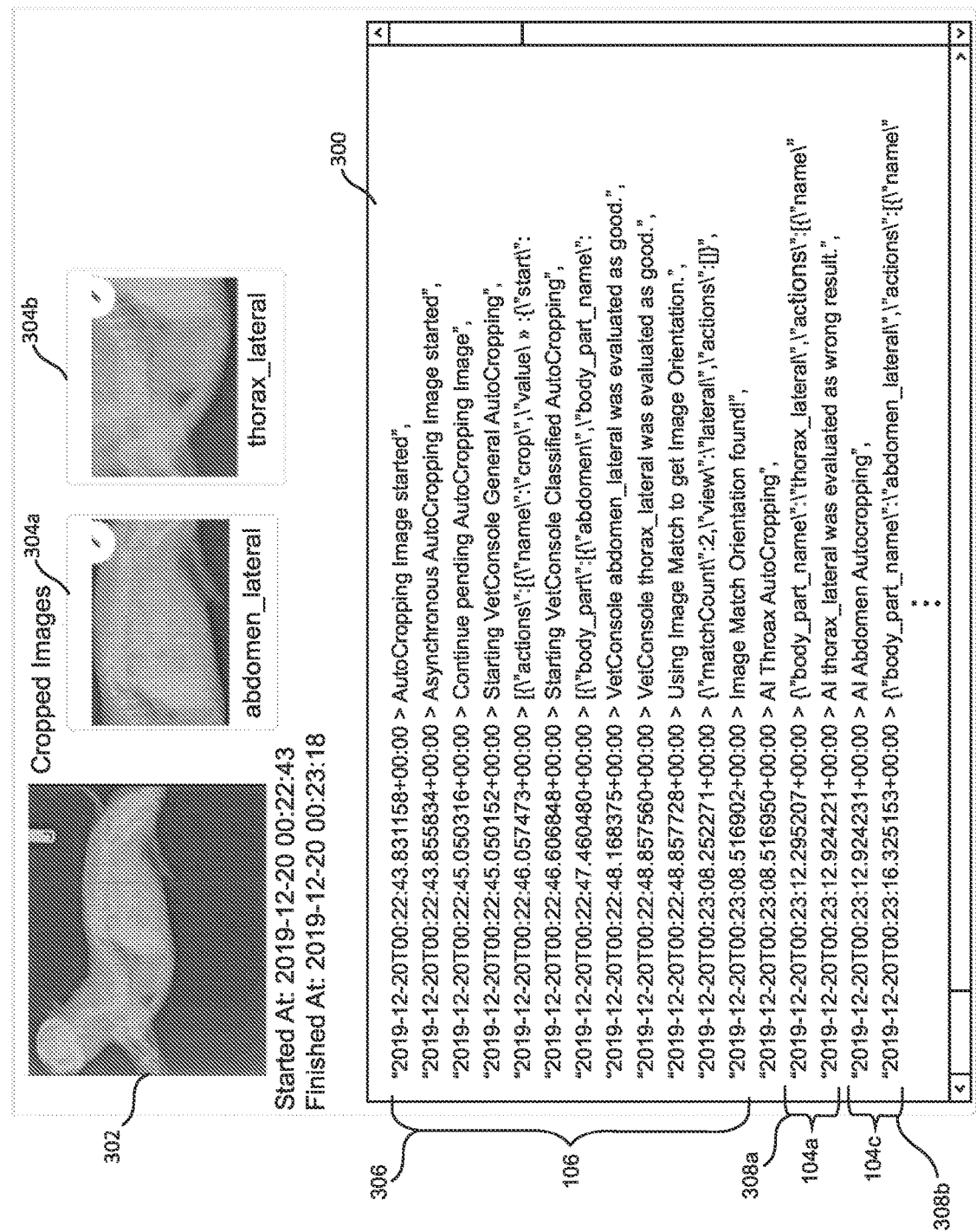

FIG. 3 is a description of a set of computer operations performed by an embodiment of the system or the method of the invention herein for the novel workflow described herein. An image 302 is processed using the radiographic image pre-processor 106 followed by a subset of AI processors 104 corresponding to identified body regions/views. Cropped images 304a, 304b of respective body regions/views that are identified by the system are shown. The total time taken by the radiographic image pre-processor to determine that the image 302 represented both a "lateral thorax" image and a "lateral abdomen" image, as reflected by the time stamps for the log entries corresponding to the bracket 306, was twenty-four seconds.

FIG. 4 is a set of conventional single condition base organ findings 401 to 407 for lungs in a radiograph followed by combinations of at least two single condition base organ findings. The permutations and combinations of seven single condition base organ findings result in exponential number of report templates.

FIG. 5A-FIG. 5N are a set of base organ findings for lungs classified based on severity as normal, minimal, mild, moderate, and severe and displayed as separate AI model results templates. The boxes 501 to 557 represent a single line item in a specific AI report template. The single line item is selected based on each AI model result template matching the finding listed under heading "Code".

FIG. 6 is a collection of individual binary models (or a library of AI models) which are deployed for analyzing radiographic images to obtain a probability result of the radiographic image being negative or positive for the condition or classification.

Figure 7:
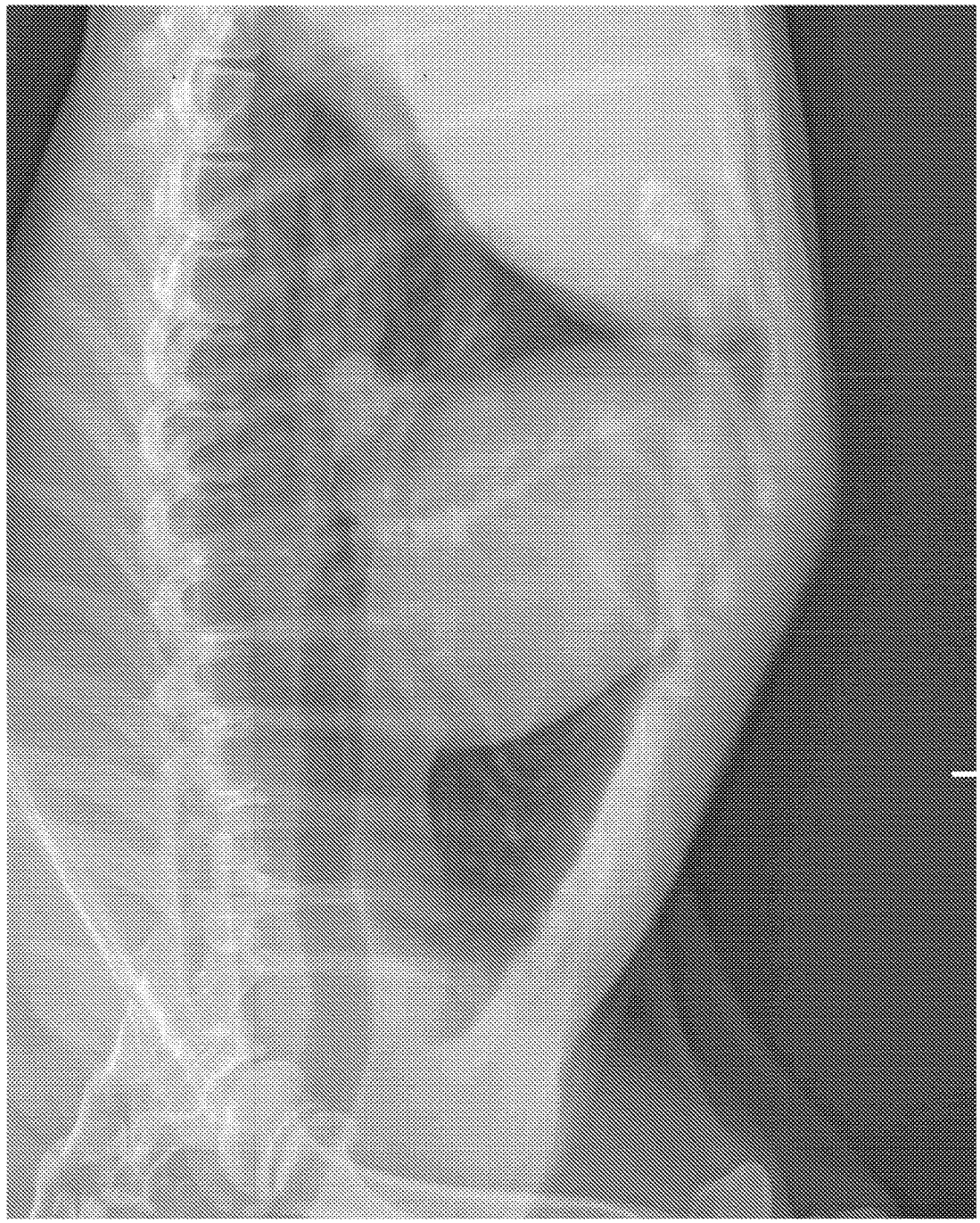

FIG. 7 is a lateral thoracic radiograph of a dog, the image having been preprocessed, cropped, labeled and identified. The radiograph image is analyzed by the library of binary AI models displayed in FIG. 6.

FIG. 8 is a screenshot of results of a single binary AI model obtained by analyzing a series of lateral radiographic images similar to the image of FIG. 7 through a specific binary AI model, for example, a bronchitis AI model.

Figure 9C:
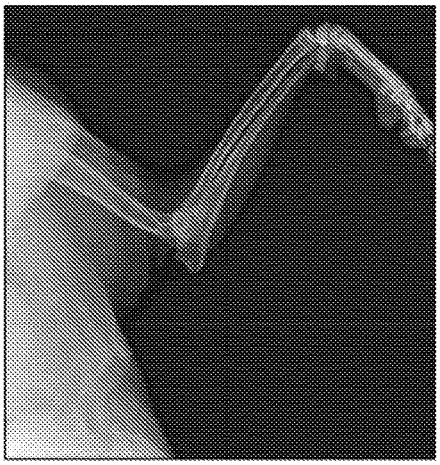
Figure 9E:
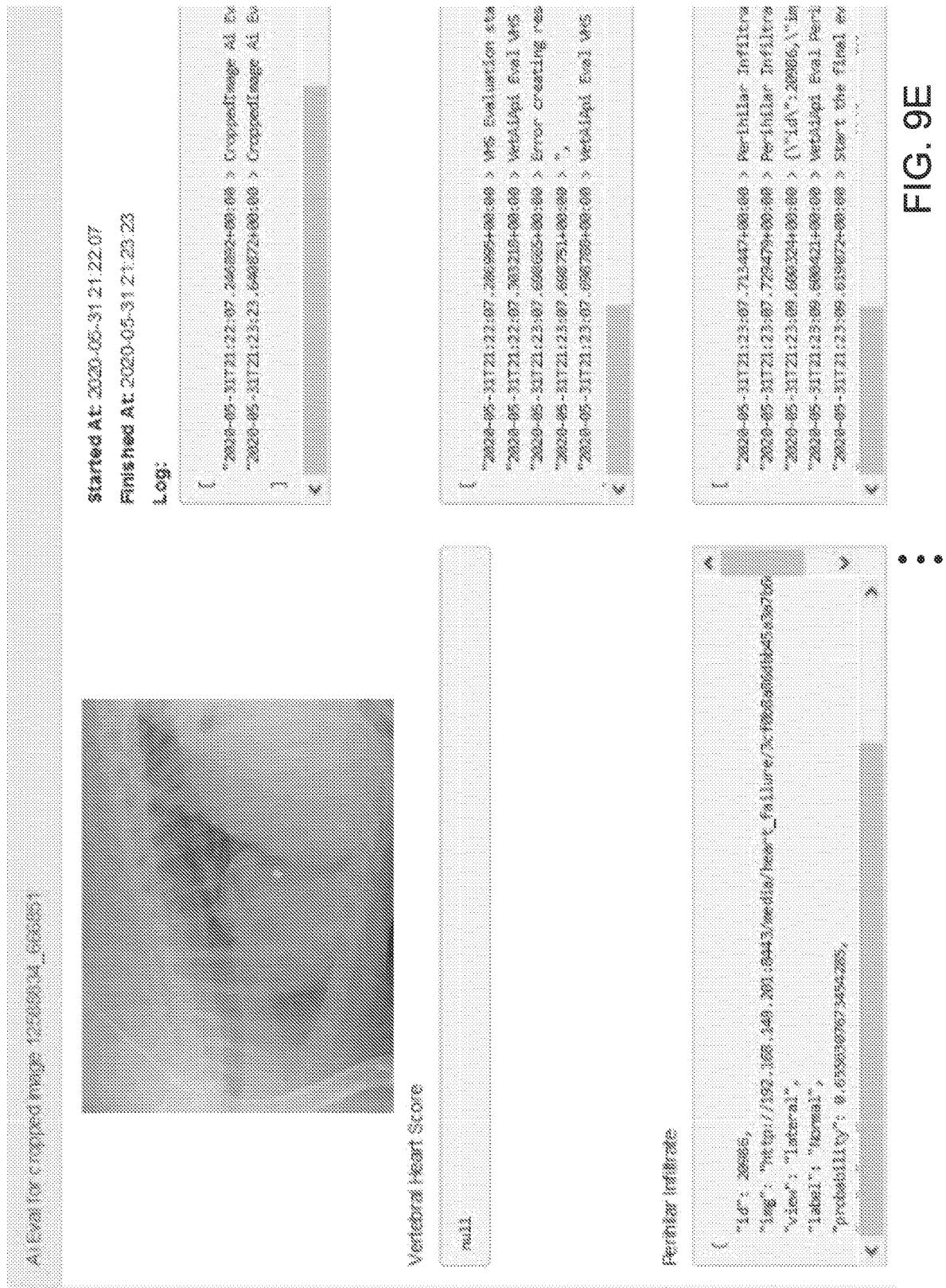

FIG. 9A-FIG. 9E are a set of screenshots showing each AI model result of a radiographic image. The visual collection of each individual AI model result per image and the AI model result mean for all images were evaluated for that specific case. The mean evaluation result for each model is created by assembling the individual image evaluation results, and is displayed at the top of the screen in FIG. 9A. Each individual image and the AI model result for that image are displayed in FIG. 9B-FIG. 9E. The time stamp 901 in FIG. 9A shows that the AI analysis was completed in less than three minutes. FIG. 9B shows results for individual AI models such as perihilar infiltrate, pneumonia, bronchitis, interstitial, diseased lungs, hypoplastic trachea, cardiomegaly, pulmonary nodules, and pleural effusion. For each AI model a label identifies the image as "normal" 902 or "abnormal" 903. Further, a probability 904 of the image being "normal" or "abnormal" for the AI model single condition is provided. FIG. 9C shows four images which are obtained by classifying and cropping a single radiographic image. The time stamps 905-908 show that the AI analysis was completed in less than two minutes. FIG. 9D and FIG. 9E show results for each AI model for the radiographic image which includes the label, the probability and the view (909) of the radiographic image, for example, lateral, dorsal, anteroposterior, posteroanterior, ventrodorsal, dorsoventral, etc.

FIG. 10 is a screenshot of an AI case result displayed in JavaScript Object Notation (JSON) format. The JSON format facilitates copying the mean evaluation results for all models in a case which may be transferred to an AI Evaluation Tester for testing to evaluate the mean evaluation results by comparing to a cluster result.

Figure 11:
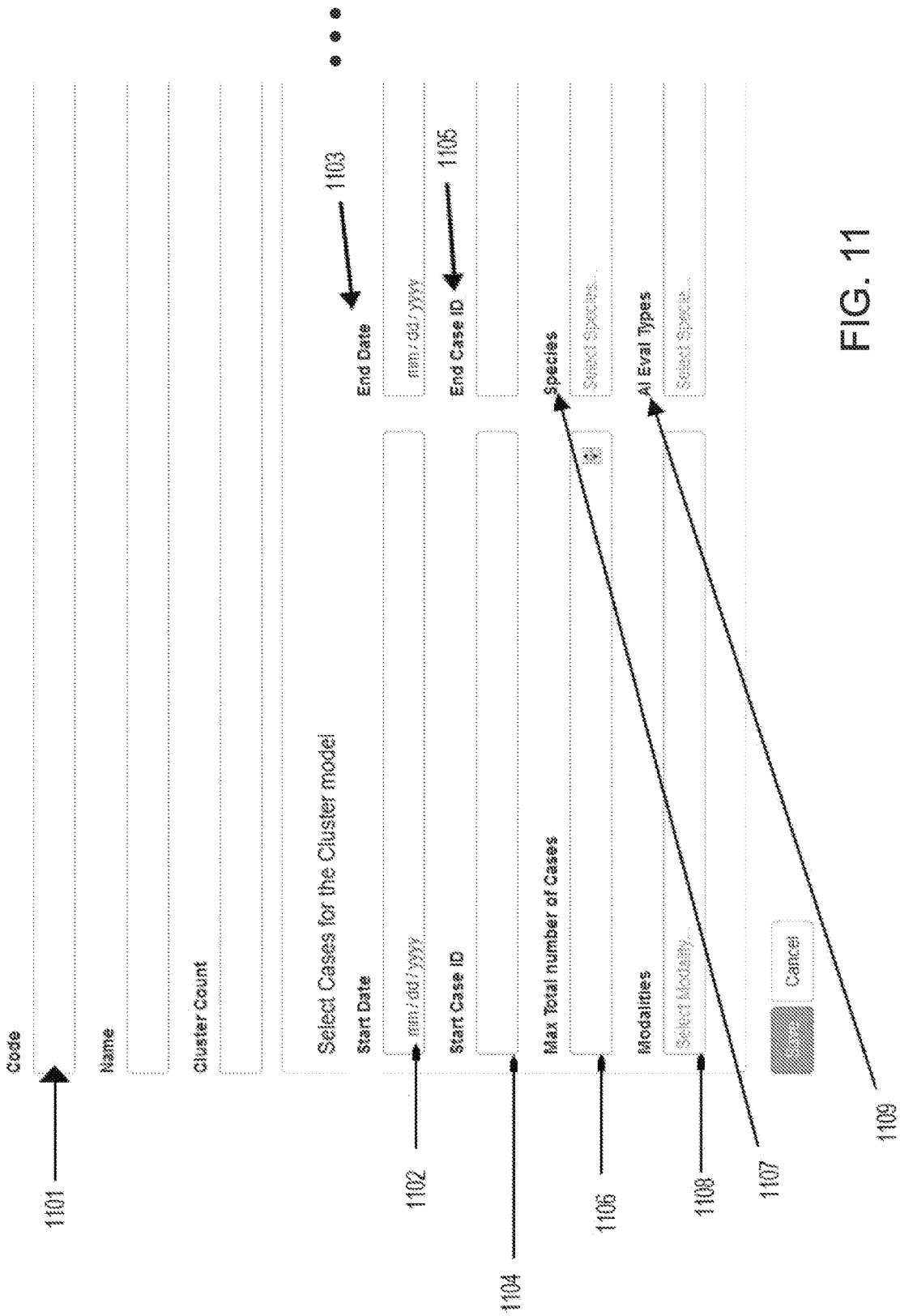

FIG. 11 is a screenshot of a graphical user interface which allows a user to create a K-Means cluster. The user assigns a name 1101 for the new cluster under "Code". The user selects various parameters to create a cluster. The user chooses a start Case date 1102 and an end Case date 1103 to select the cases. The user chooses a start Case ID 1104 and an end Case ID 1105 to select the cases. The user chooses a maximum number of cases 1106 that are to be included in the cluster. The user chooses species 1107 such as dog, cat, dog or cat, human, etc. for the cases to be included in the cluster. The user selects specific diagnostic modalities 1108 such as X-ray, CT, MRI, blood analysis, urinalysis, etc. to be included in creating the cluster. The user specifies separating the evaluation results into a specific number of clusters. The number of clusters range from a minimum of one cluster to a maximum number of clusters limited only by total number of cases entered into the cluster.

FIG. 12A-FIG. 12B is a screenshot of AI cluster results listed as a numerical table. The far left column 1201 is the case ID, the next nine columns are the mean evaluation results 1202 for each binary model for the specific case ID, the next column is the cluster label or cluster location 1203 which includes the specific case based on the collection of evaluation results, the next four columns are the cluster coordinates and centroid coordinates, the last number is the case ID 1204 of the centroid or center of that specific cluster. The radiologist report for the best matched case ID is obtained. This radiologist report is then used to generate the report for the new AI case. This process allows for infinite scalability in terms of the number of AI models incorporated compared to the conventional semi-manual process of report creation.

Figure 13:
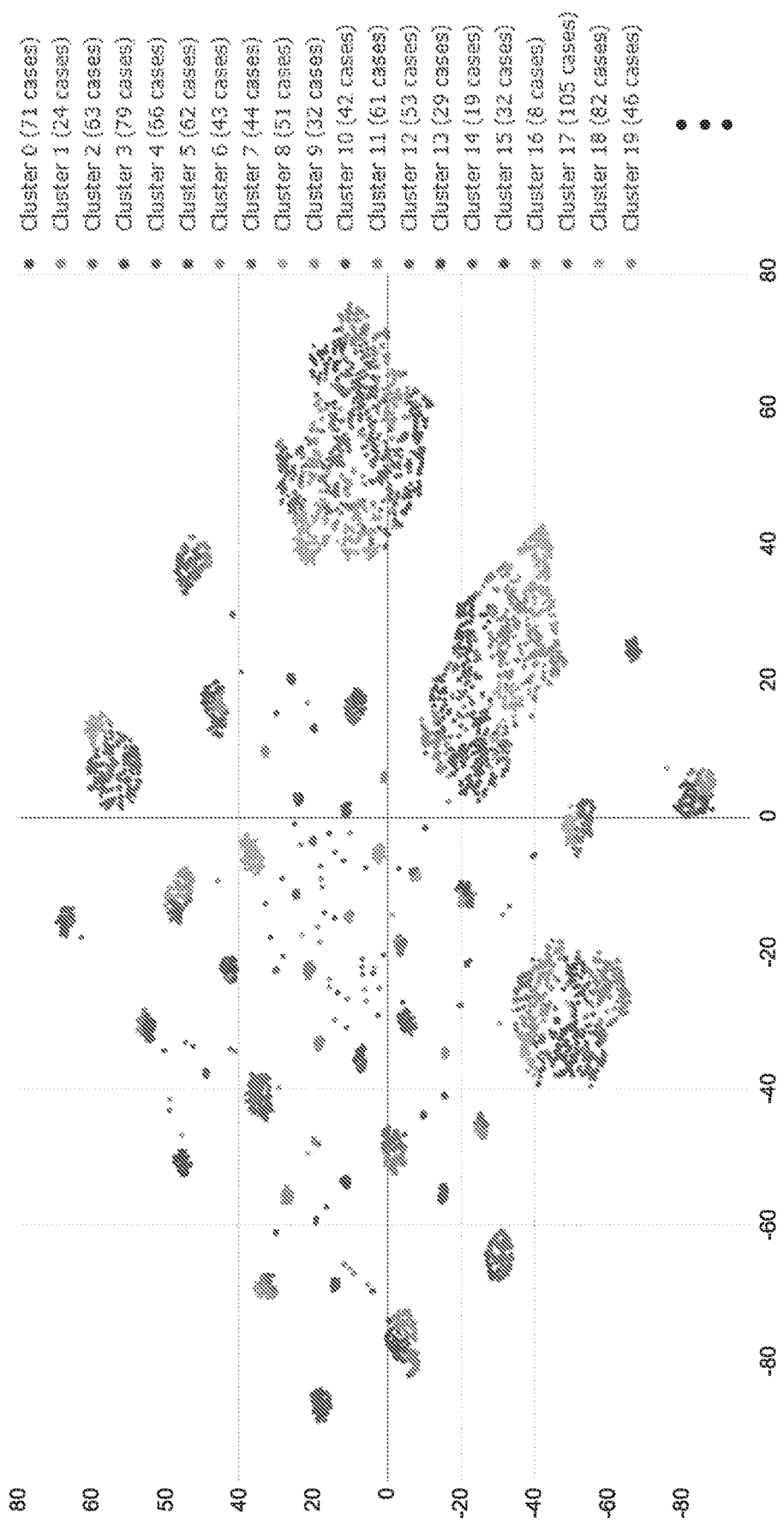

FIG. 13 is an example of a clustering graph. The clustering graph is created by dividing the mean evaluation results into multiple different clusters depending on user defined parameters 1102-1108. This example clustering graph is divided in 180 different clusters each represented by collection nearby of dots of a single color plotted on the graph.

FIG. 14 is a screenshot of user interface showing AI cluster models generated based on user defined parameters 1102-1108. The first column from the left shows the cluster ID 1401, the second column shows assigned name of the cluster model 1402, the third column shows the number of different clusters 1403 into which the AI data have been divided, fourth column shows the body region 1404 that has been evaluated based on cluster data results.

FIG. 15 is a screenshot of a user interface showing screening evaluation configuration. The user interface allows assigning a specific "cluster model" 1502 to a specific "screening evaluation configuration" name 1501. The status 1503 of the screening evaluation configuration provides additional data about the configuration such as whether the configuration is in live, testing or draft mode. The live mode is for production and the testing mode is for development.

Figure 16A:
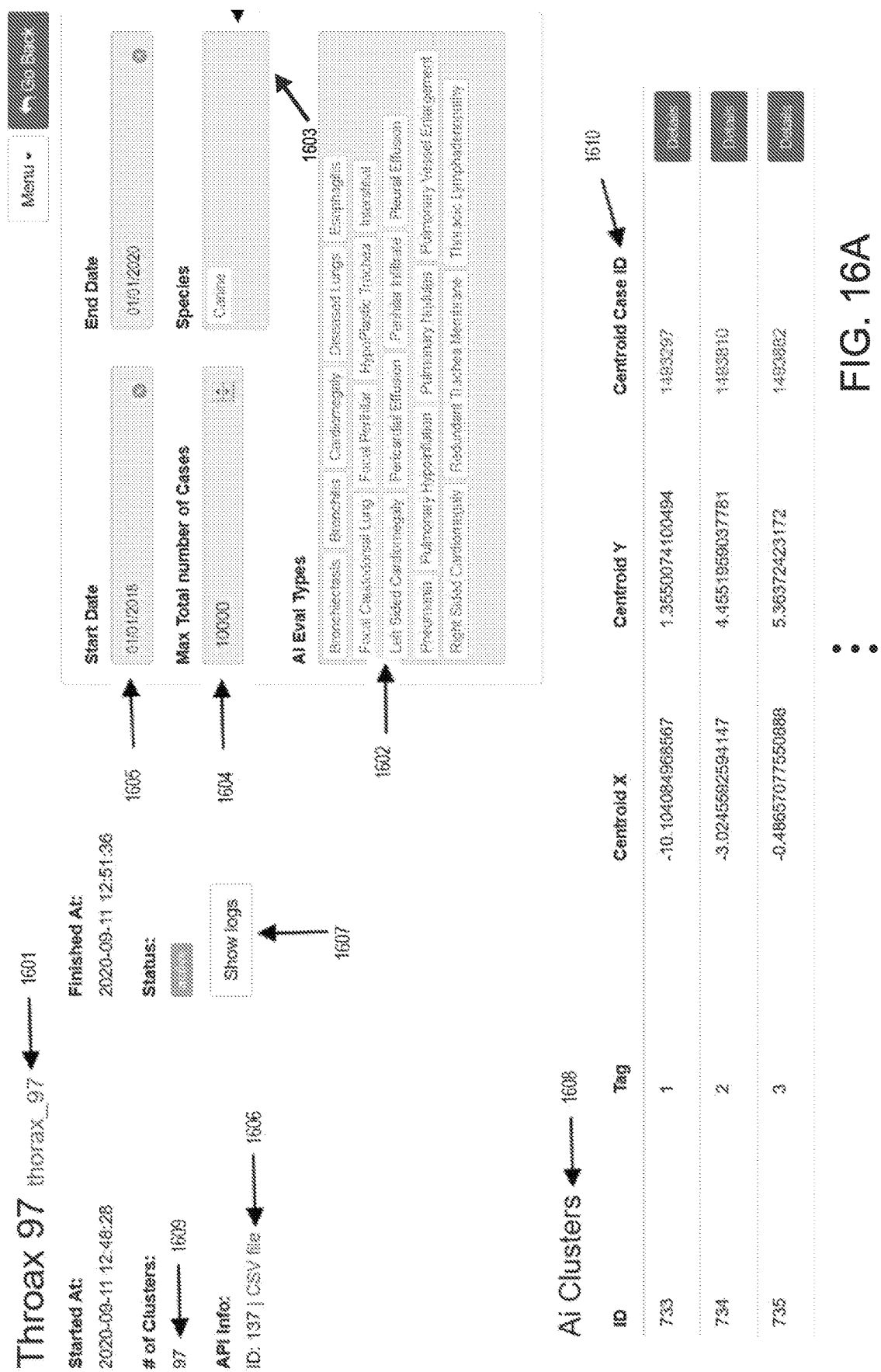

FIG. 16A-FIG. 16C are a set of screenshots of a user interface showing the details for a specific cluster model. FIG. 16A shows a user interface displaying data for a cluster model 1601 Thorax 97. The AI evaluation classifier types 1602 included in the cluster are listed. The species or a collection of species 1603 specific for the cluster model are displayed. The maximum number of cases 1604 with evaluation results used to generate the cluster are displayed. The user interface shows the start and end dates 1605 for cases used to create the cluster. A link 1606 to the comma separated value (CSV) file of FIG. 12A-FIG. 12B showing the cluster in numerical table format is displayed. A portion of sub-clusters 1608 created from the parameters 1602-1605 are listed. The total number of sub-clusters 1609 created for this cluster group are displayed. For each sub-cluster a centroid case ID 1610 is displayed. A link to the log 1607 for building the cluster is displayed. FIG. 16B is a screenshot of the log created for cluster model 1601 Thorax 97. FIG. 16C is a screenshot of a portion of AI evaluation models including vertebral heart score, perihilar infiltrate, pneumonia, bronchitis, interstitial, and diseased lungs.

Figure 17A:
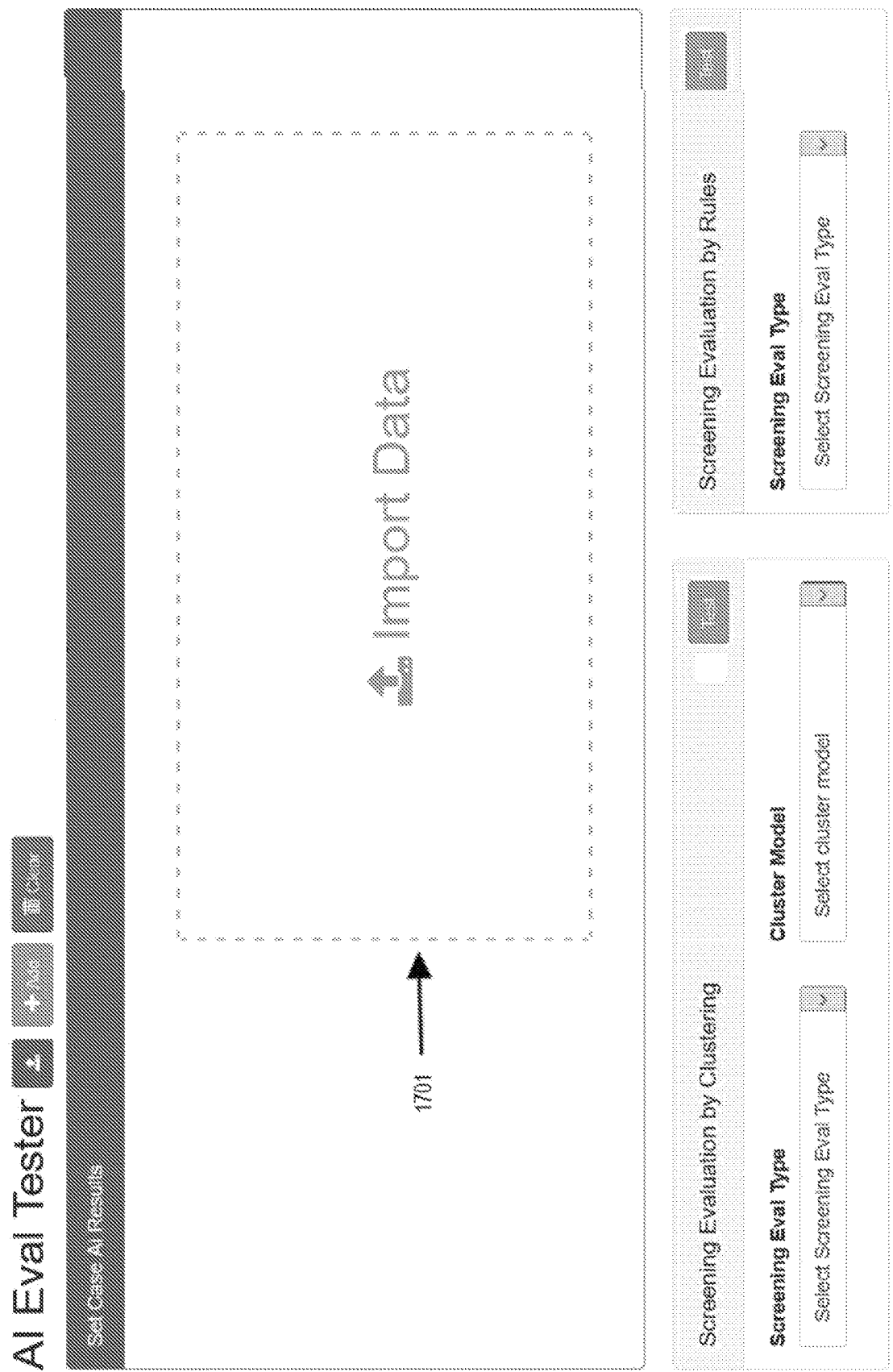
Figure 17D:
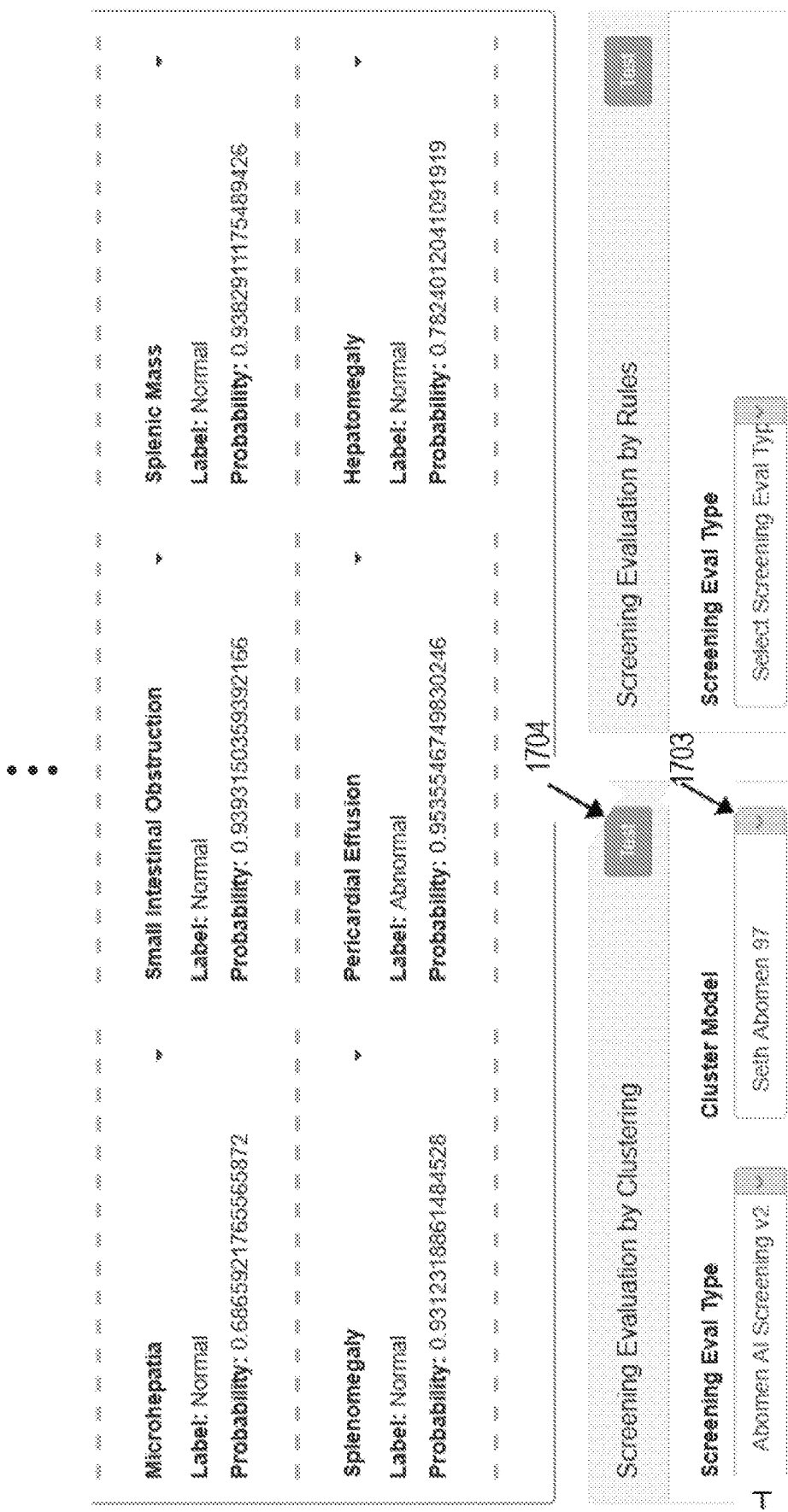

FIG. 17A-FIG. 17D are a set of screenshots of a user interface for AI Evaluation Tester. FIG. 17A shows user interface (AI Eval Tester) in which the values of mean evaluation results for all models in JSON format of FIG. 10 are imported 1701 to analyze the closest matched case/exemplar result match in a cluster using K-means clustering from a case cluster made from an AI dataset. FIG. 17B shows the values of mean evaluation results for all models in JSON format of FIG. 10 being imported into the AI Evaluation tester. FIG. 17C and FIG. 17D show the evaluation results which have been imported for the specific case. FIG. 17D shows screening evaluation type 1702 and the cluster model 1703 associated with the screening evaluation type being selected by the user. By clicking test 1704, the evaluation results displayed in FIG. 10 are analyzed and assigned to the closest matched case/exemplar result match in a cluster. The closest radiologist report, top ranking radiologist sentences and centroid radiologist report for the exemplar result match cluster are collected and displayed.

Figure 18B:
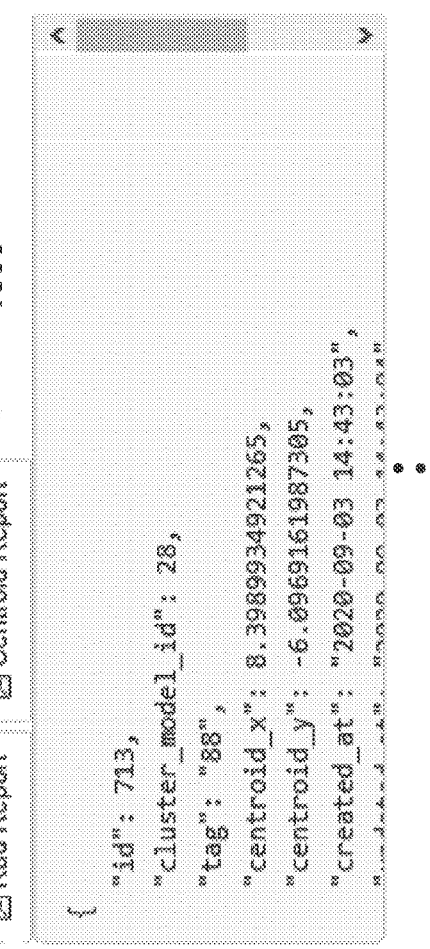
Figure 18D:
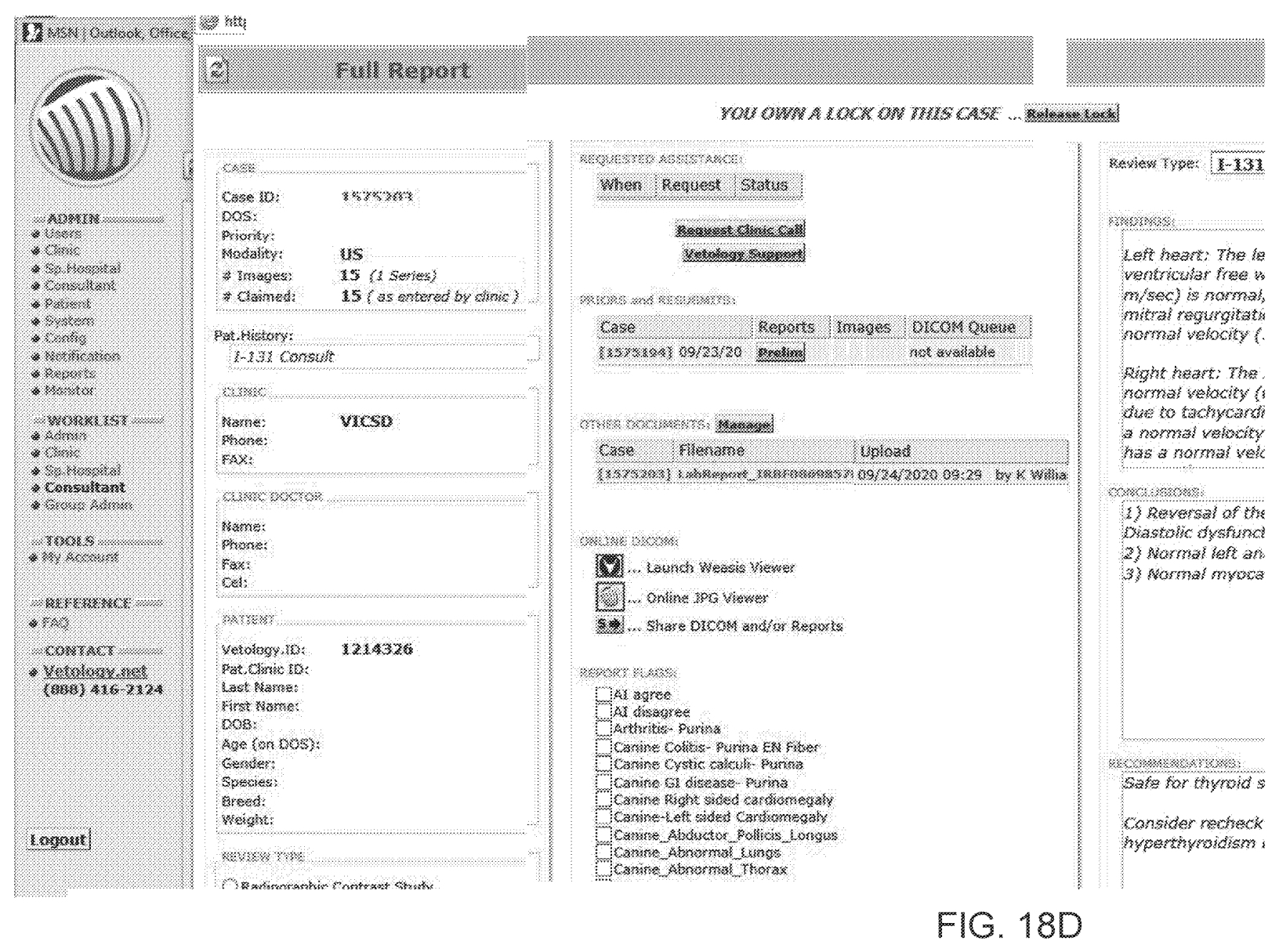

FIG. 18A-FIG. 18D are a set of screenshots of a user interface. FIG. 18A and FIG. 18B are a set of screenshots of the user interface which shows the result displayed after clicking test 1704 on the AI Evaluation tester. The diagnosis and conclusory findings 1801 from radiologist report that are closest to the evaluation results based on previously created cluster results are displayed. The evaluation findings 1802 are selected from radiologist reports in the cluster of the evaluation results and filtered based on the prevalence of a specific sentence in the findings section of the specific cluster. The recommendations 1803 from the radiologist report in the cluster are selected based on prevalence of each sentence or a similar sentence in the recommendations section of this cluster. The interface 1804 shows the radiologist report of the cluster and the interface 1805 shows the radiologist report of the centroid of the cluster. FIG. 18C is a screenshot of a user interface which lists the ranking of the sentences in a radiology report based on the specific cluster results. The sentences include conclusory sentences 1806, findings sentences 1807, and recommendations sentences 1808. FIG. 18D is a screenshot of a user interface which allows the user to edit the radiology report by editing the findings section 1809, the conclusion section 1810 or the recommendation section 1811 by adding or removing specific sentences.

FIG. 19 is a radiologist report for the closest match dataset case, which is used to generate the radiology report for the new case. The AI Evaluation tester displays the closest radiologist report to the current AI evaluation results based on similarity of the evaluation results between the new image AI evaluation results and the AI evaluation results within the cluster and the radiologist report from the centroid of the selected cluster.

Figure 20A:
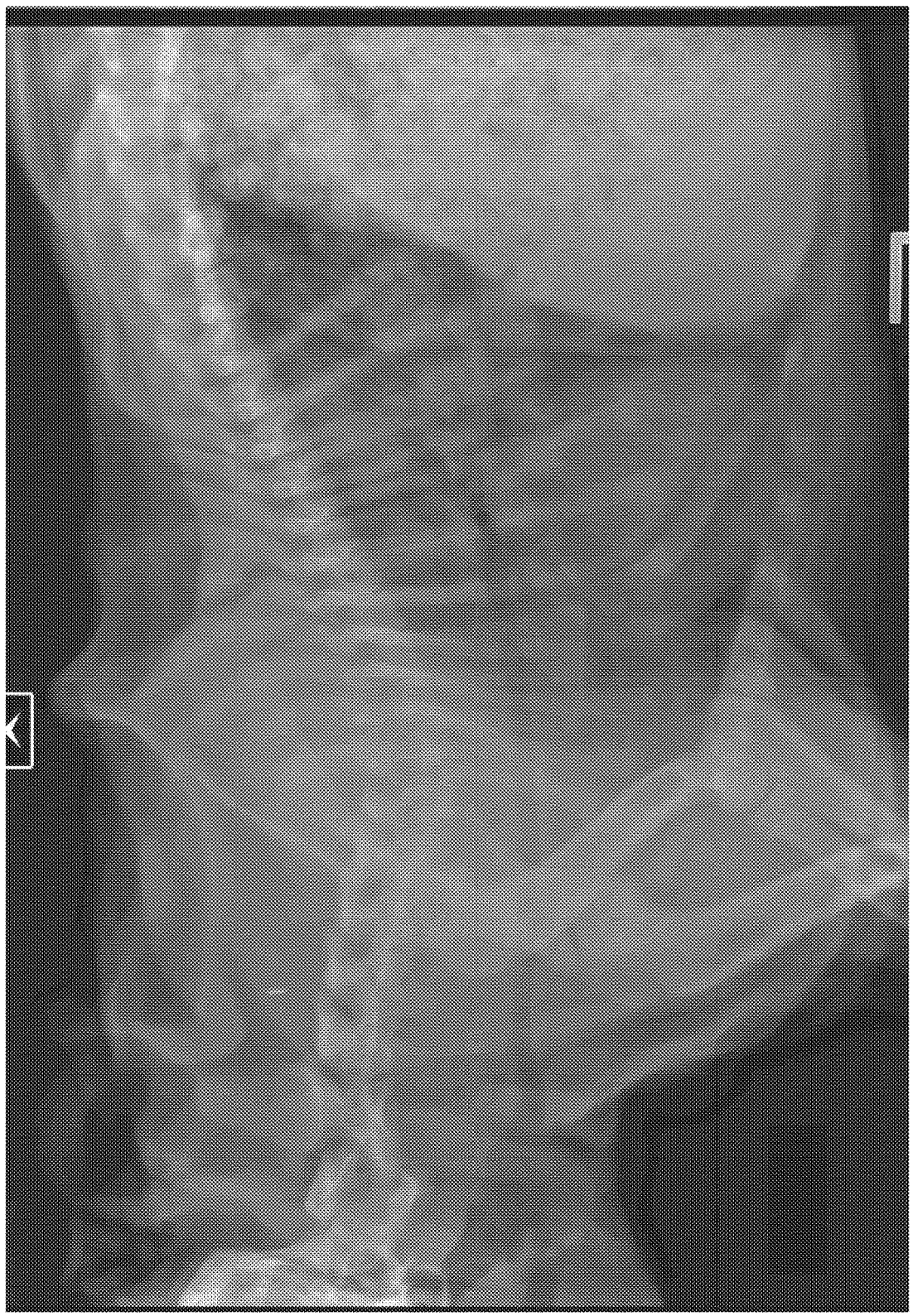
Figure 20B:
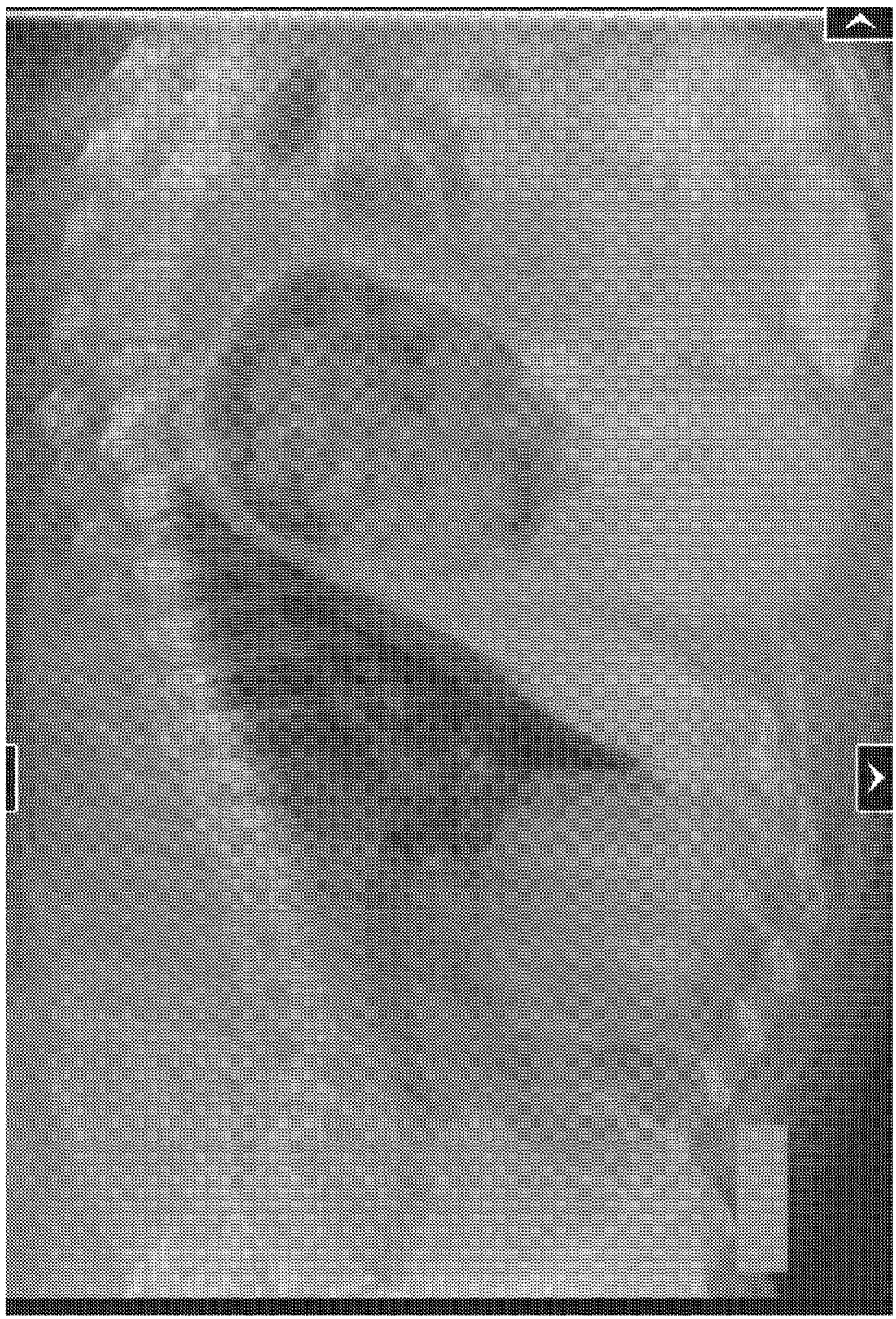

FIG. 20A and FIG. 20B are a set of radiographs. FIG. 20A is the newly received radiograph being analyzed and FIG. 20B is the radiograph that is selected by the results of the AI evaluation as the closest match based on the cluster model. The cluster match is based on AI evaluation results rather than image match results.

Figure 21A:
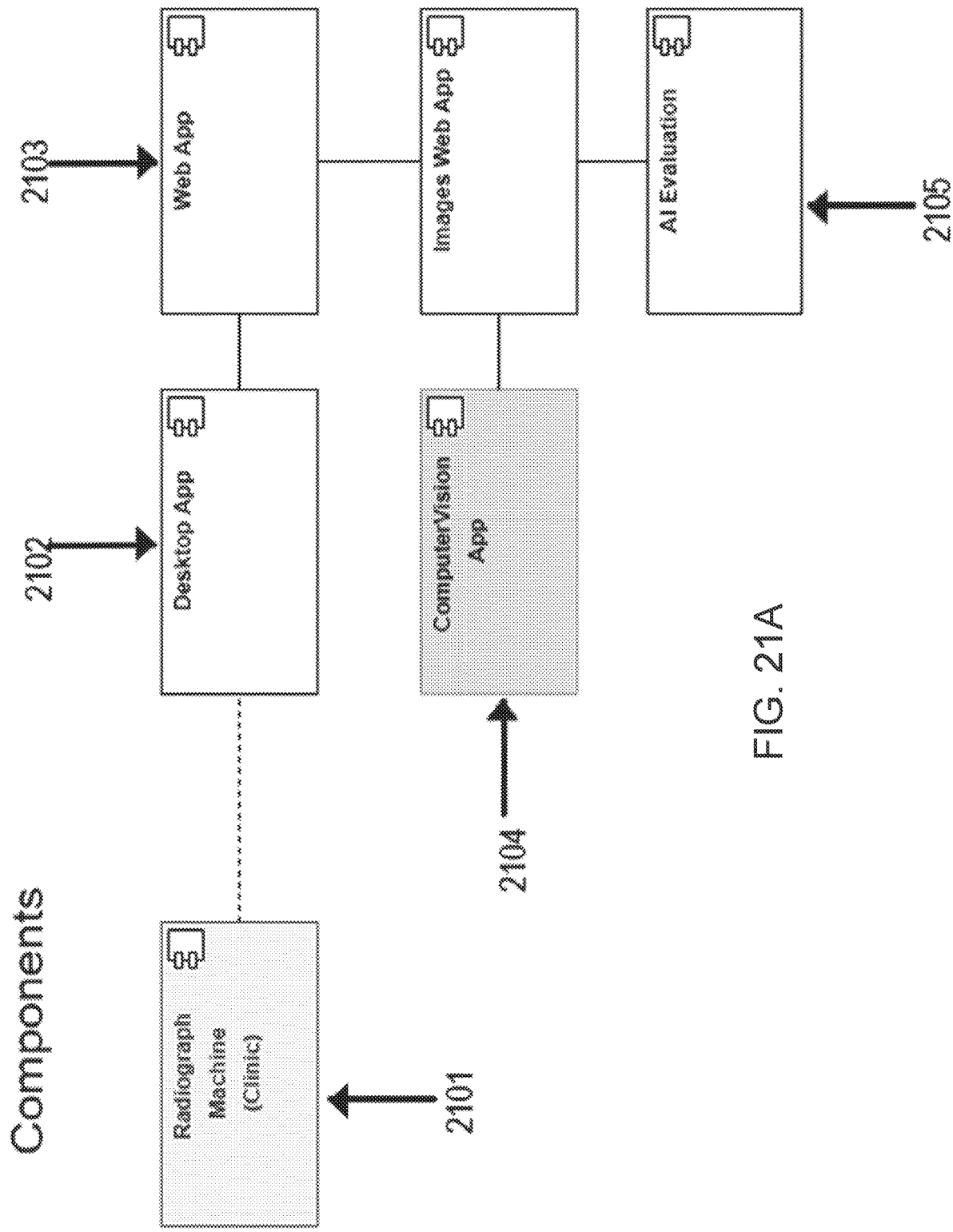
Figure 21B:
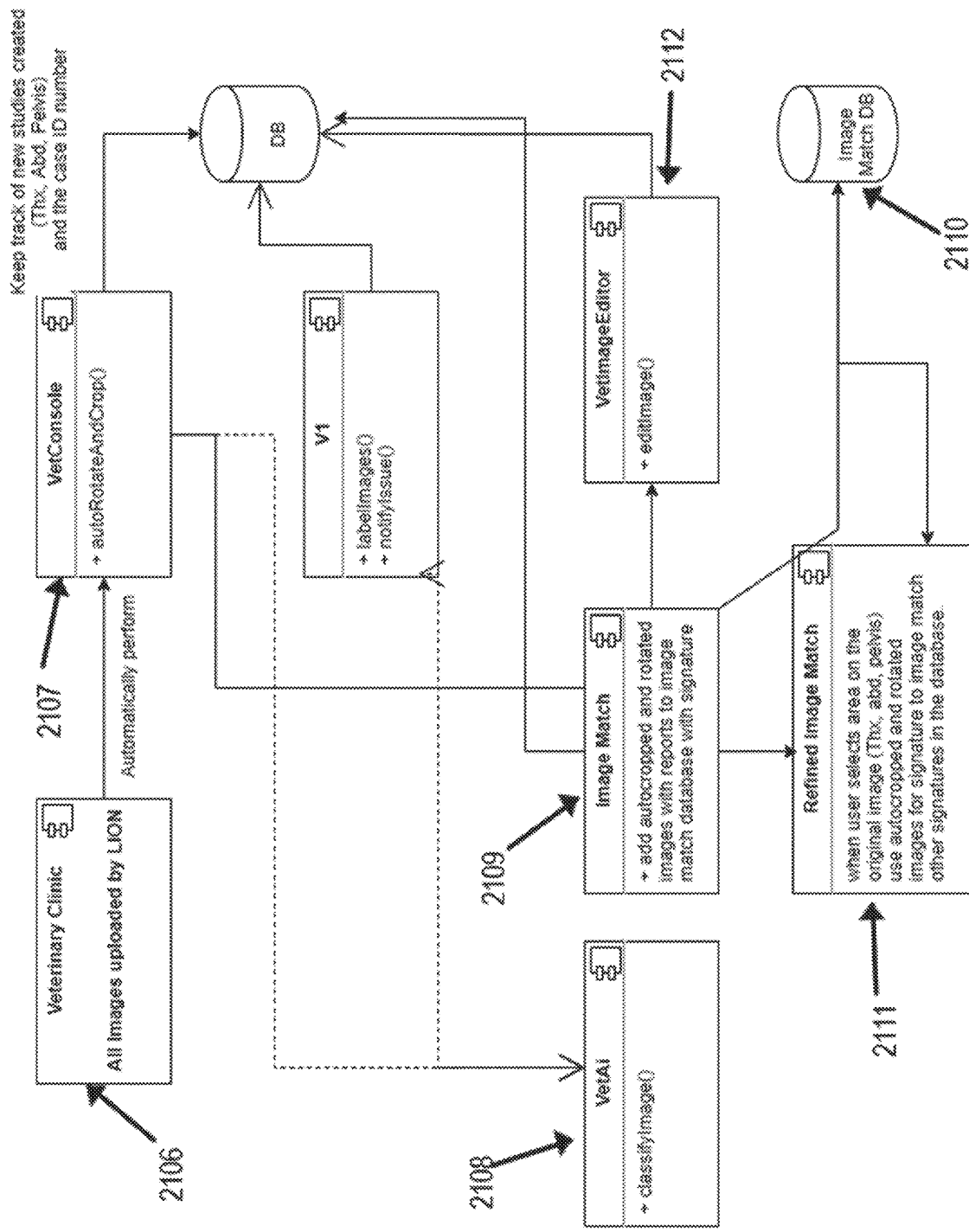

FIG. 21A and FIG. 21B are a set of schematic drawings of the components in an AI radiograph processing unit. FIG. 21A is a schematic drawing showing that the radiograph machine 2101 sends the radiographic image to a desktop application 2102 which directs the image to a web application 2103. The computer vision application 2104 and the web application directs the images to an image web application which directs the image to AI evaluation 2105. FIG. 21B is a schematic drawing of components in an image match AI processing. The images uploaded in Local Interface to Online Network (LION) 2106 in a veterinary clinic are directed to a VetConsole 2107 which autorotates and auto-crops the images to obtain sub-images. The sub-images are directed to three locations. The first location is to the VetAI console 2108 to classify the image. The second location is to image match console 2109 to add the sub-images with reports to image match database. The third location is to the image database 2110 which stores new images and the corresponding case ID numbers. The image match console 2109 directs the images to refined image match console 2111 or VetImage Editor console 2112 for further processing.

Figure 22A:
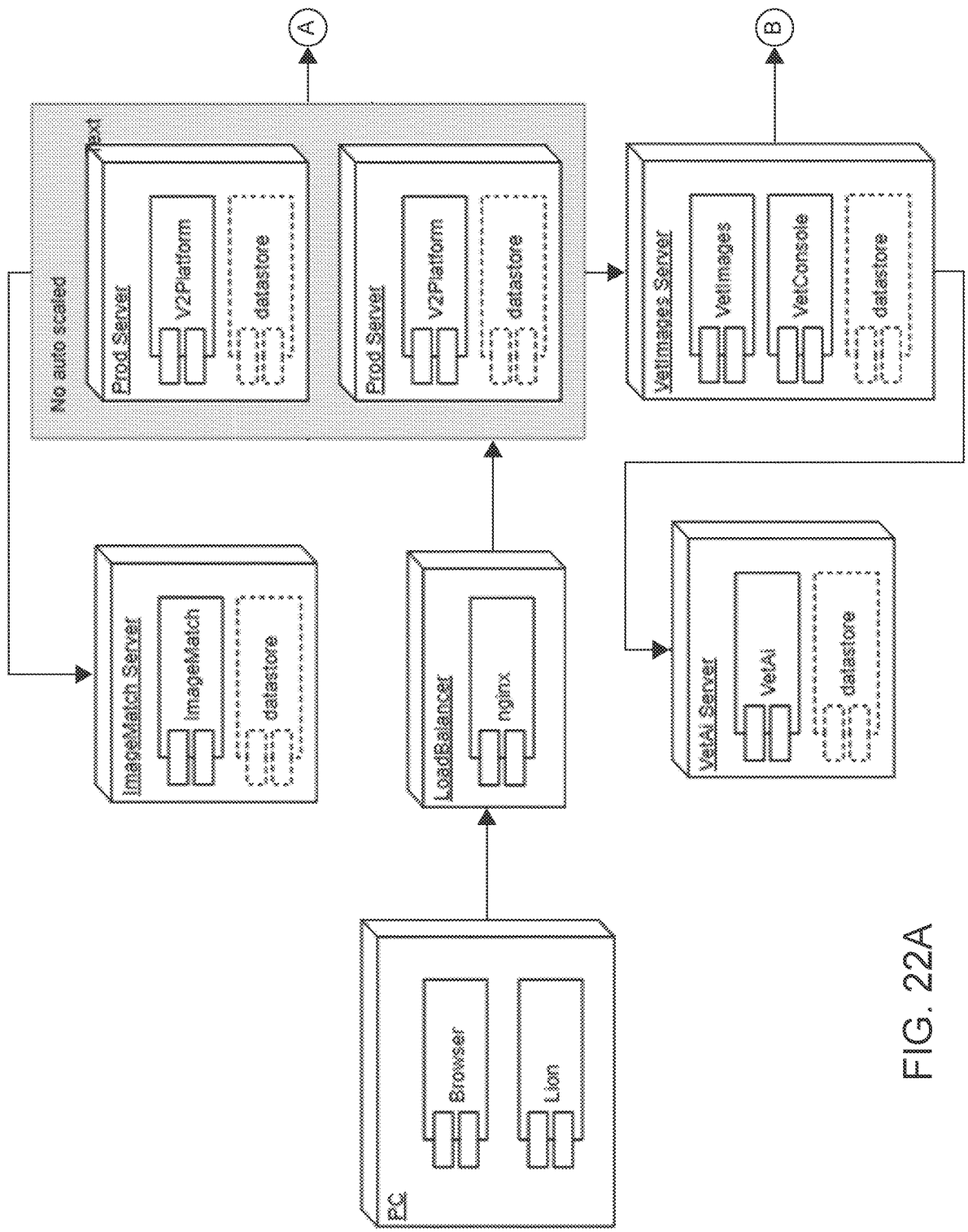
Figure 22B:
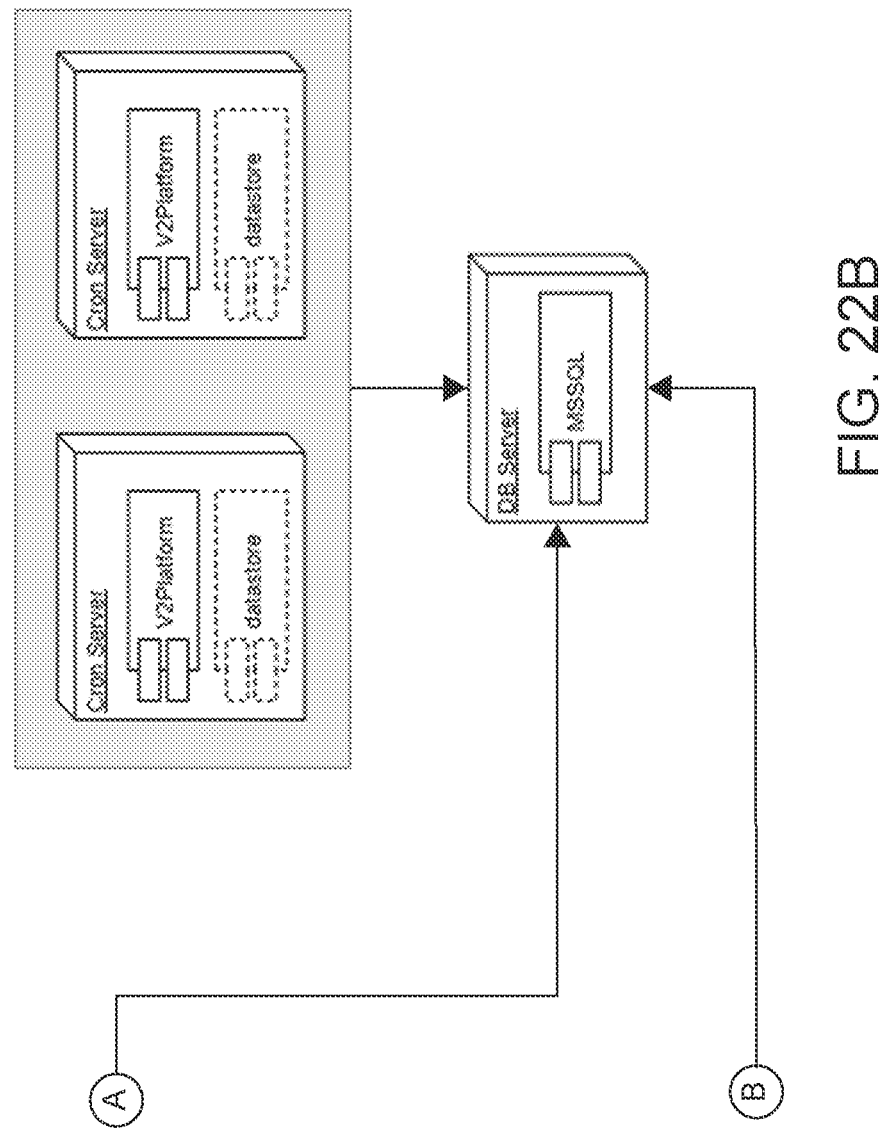
Figure 22C:
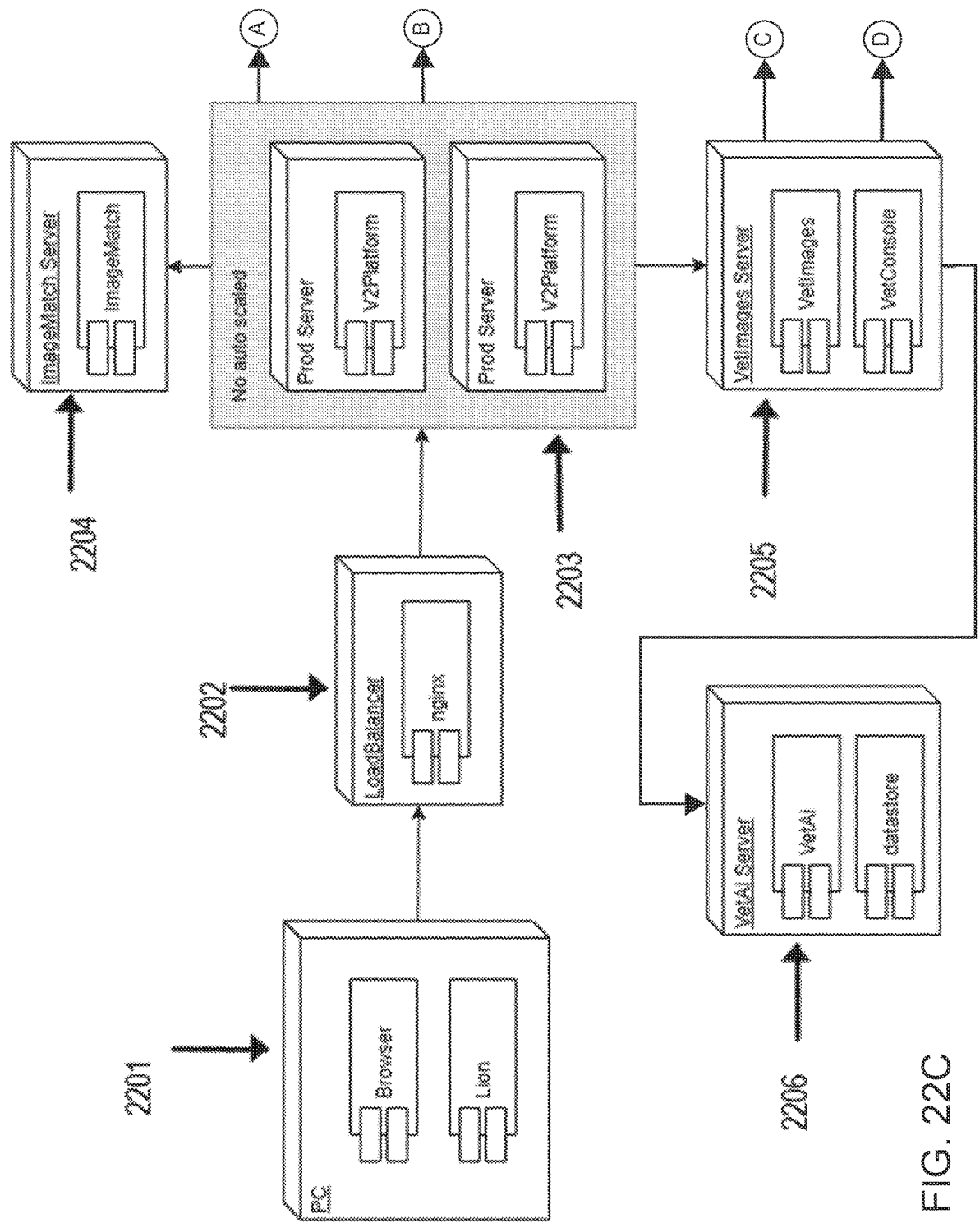
Figure 22D:
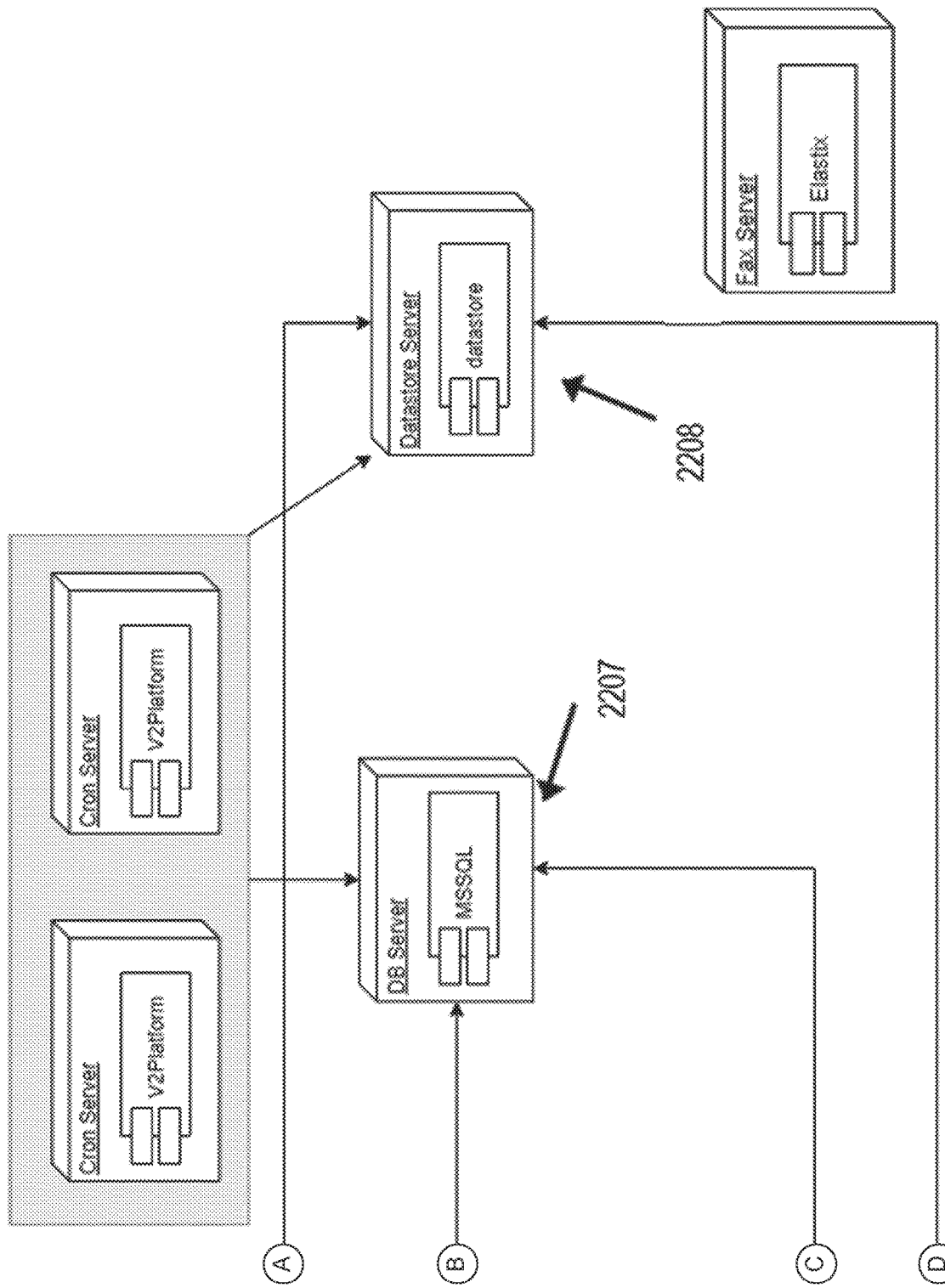

FIG. 22A-FIG. 22B are a set of schematic drawings of the server architecture for image matching. FIG. 22A-FIG. 22B are a schematic drawing of the server architecture being currently used in AI radiograph analysis. FIG. 22C-FIG. 22D are is a schematic drawing of the server architecture for AI radiograph analysis including pre-processing the radiographic images, analyzing the images using AI diagnostic processors and preparing reports based on clustering results. The image from the PC 2201 is directed to a NGINX load balancing server 2202 which directs the image to V2 cloud platform 2203. The image is then directed to the image match server 2204, the VetImages server 2205 and the database Microsoft SQL server 2207. The VetImages server direct the image to VetAI server 2206, the database Microsoft SQL server 2207 and the datastore server 2208.

Figure 23A:
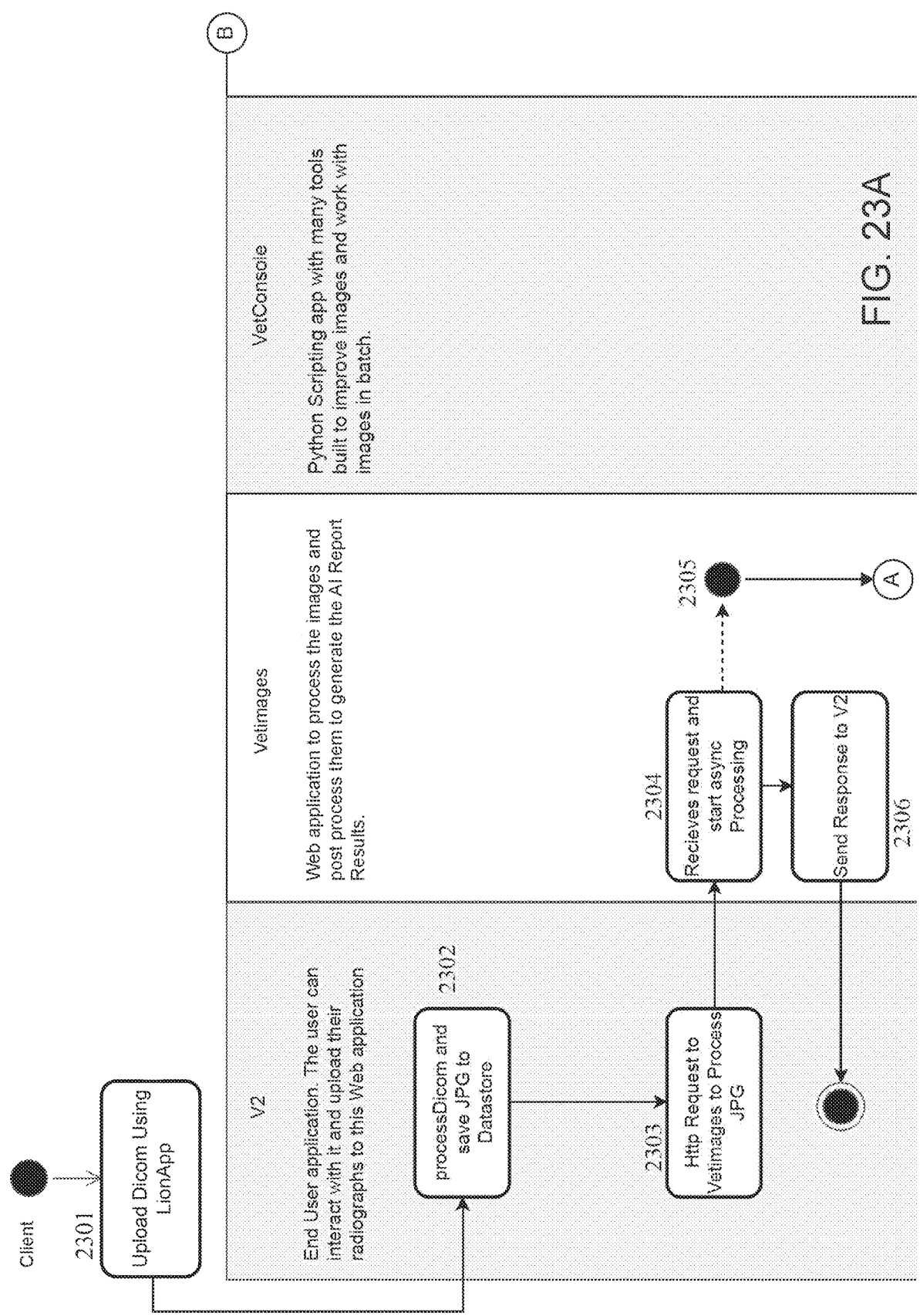
Figure 23B:
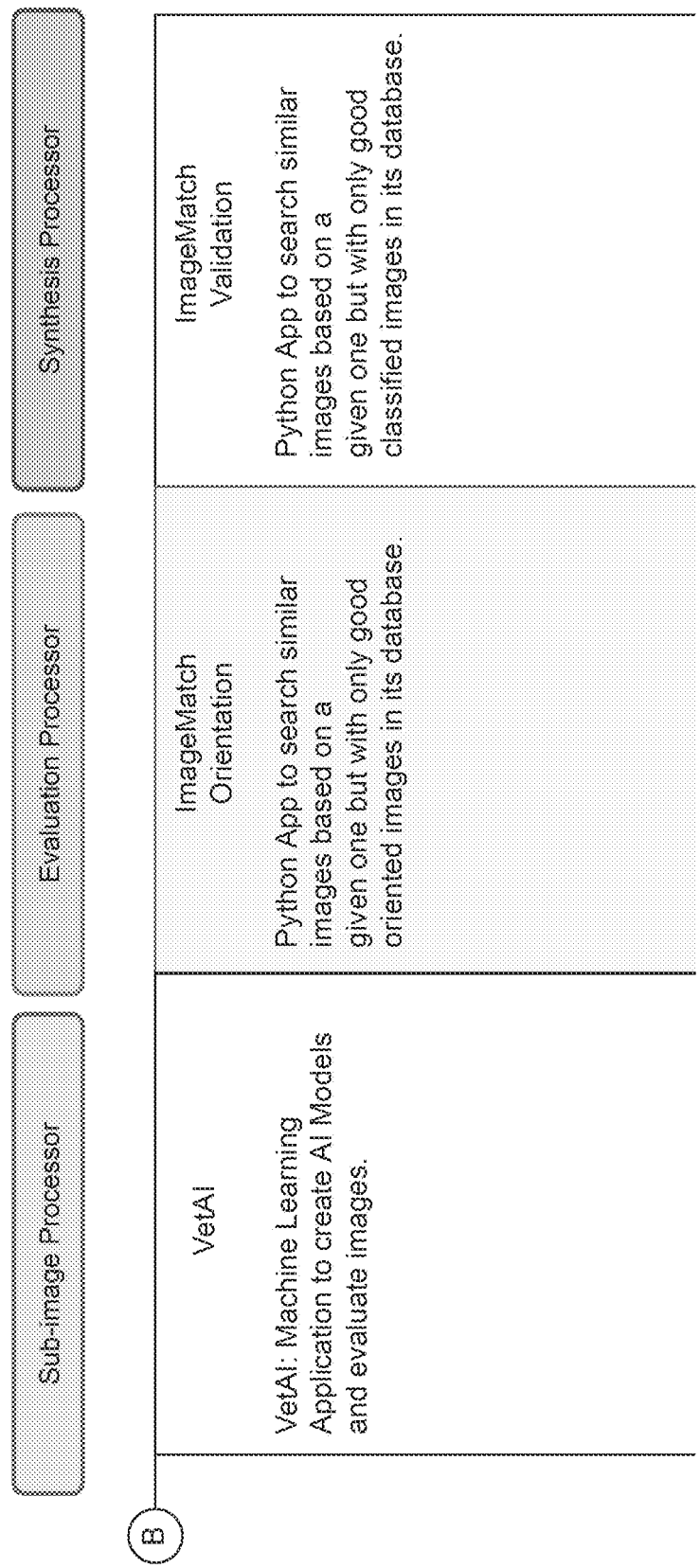
Figure 23C:
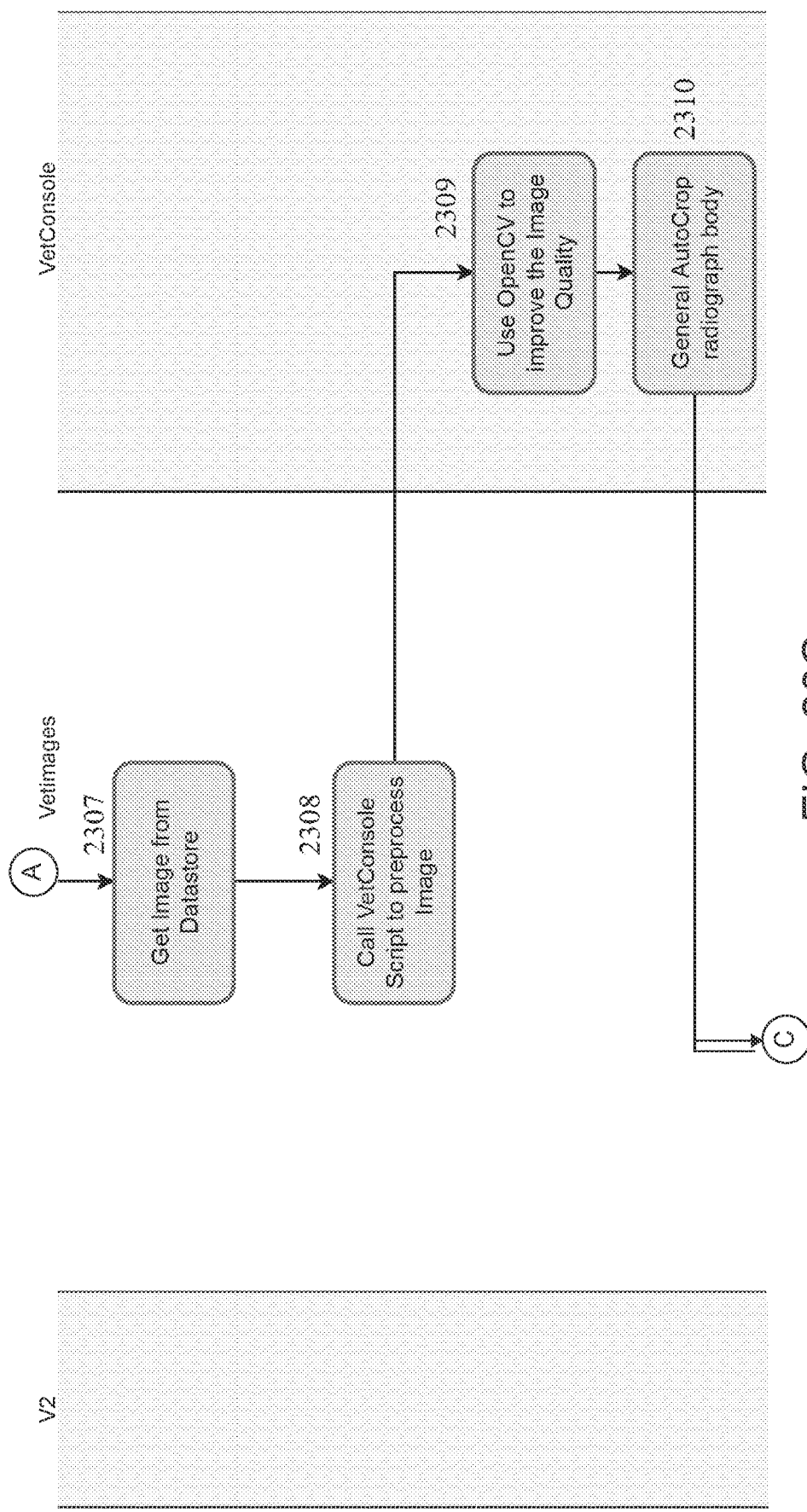
Figure 23D:
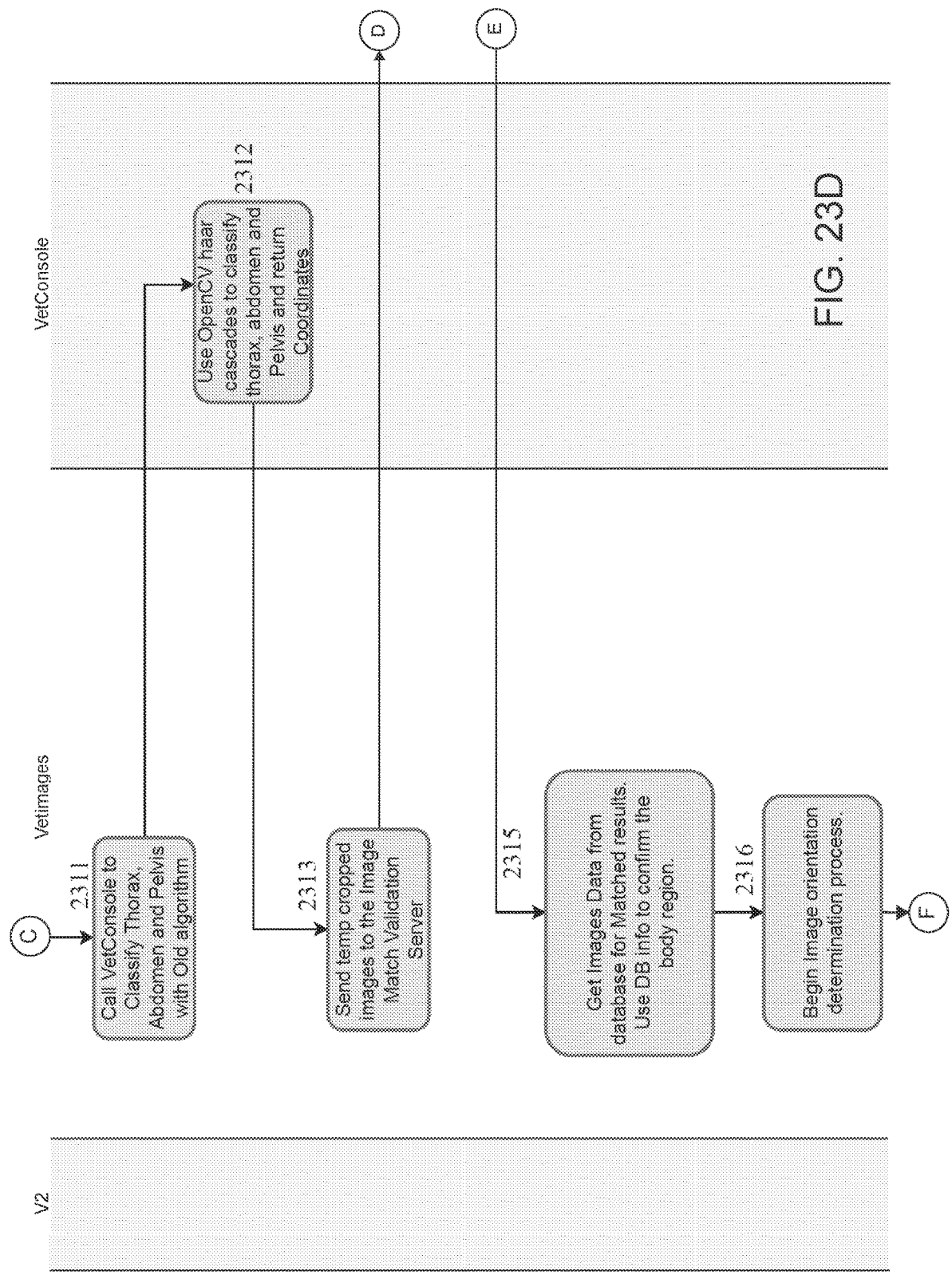
Figure 23E:
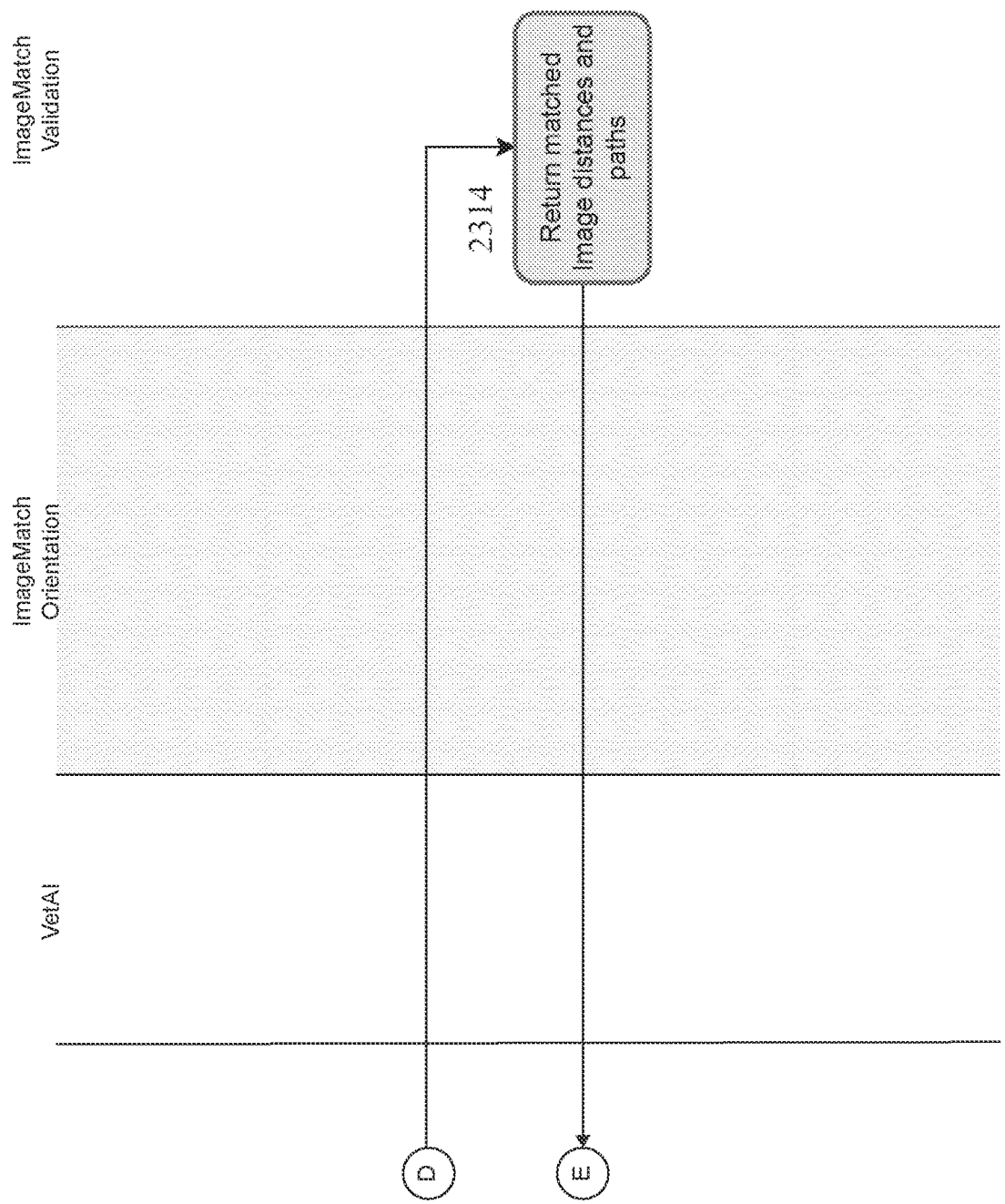
Figure 23F:
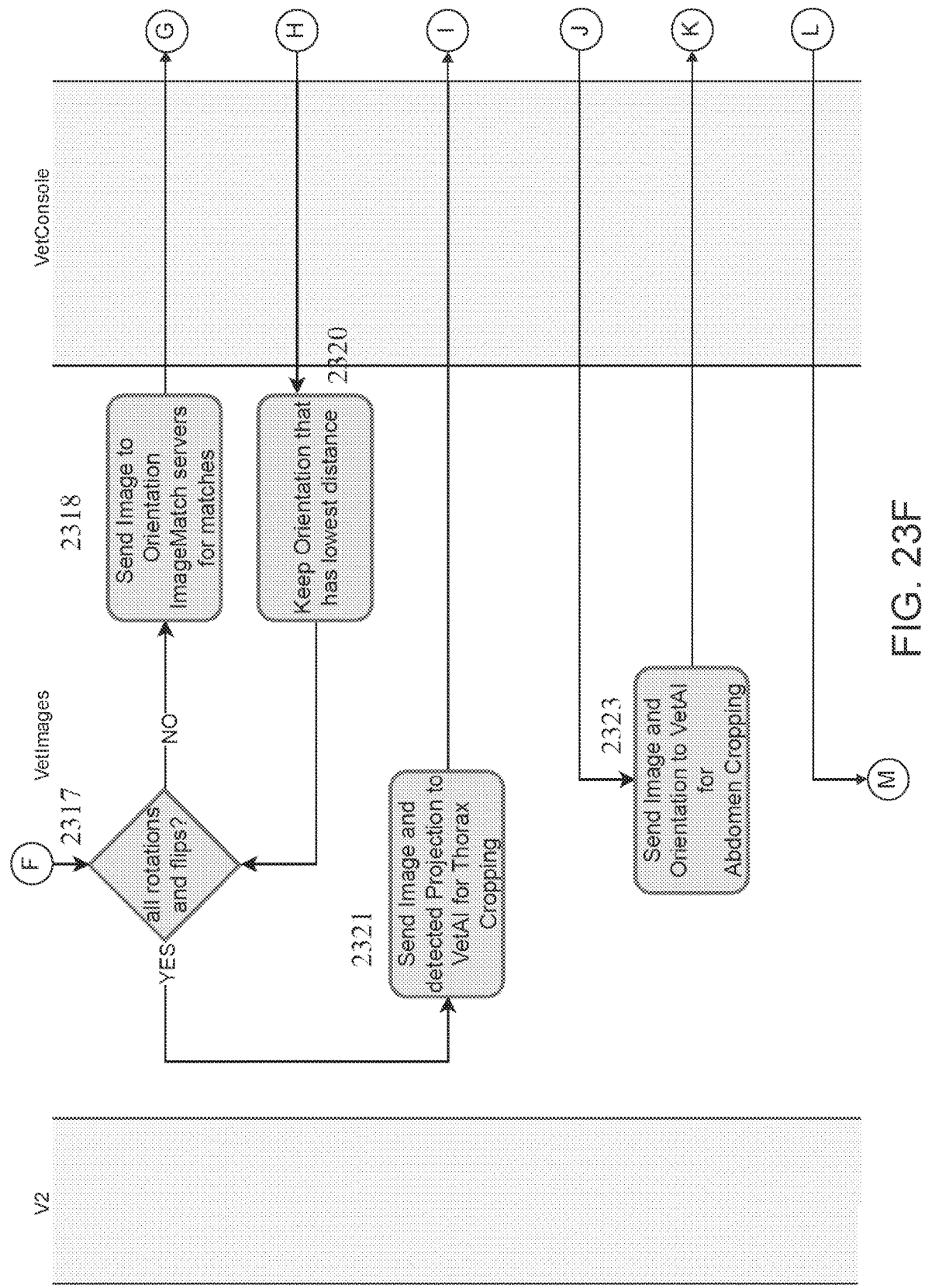
Figure 23G:
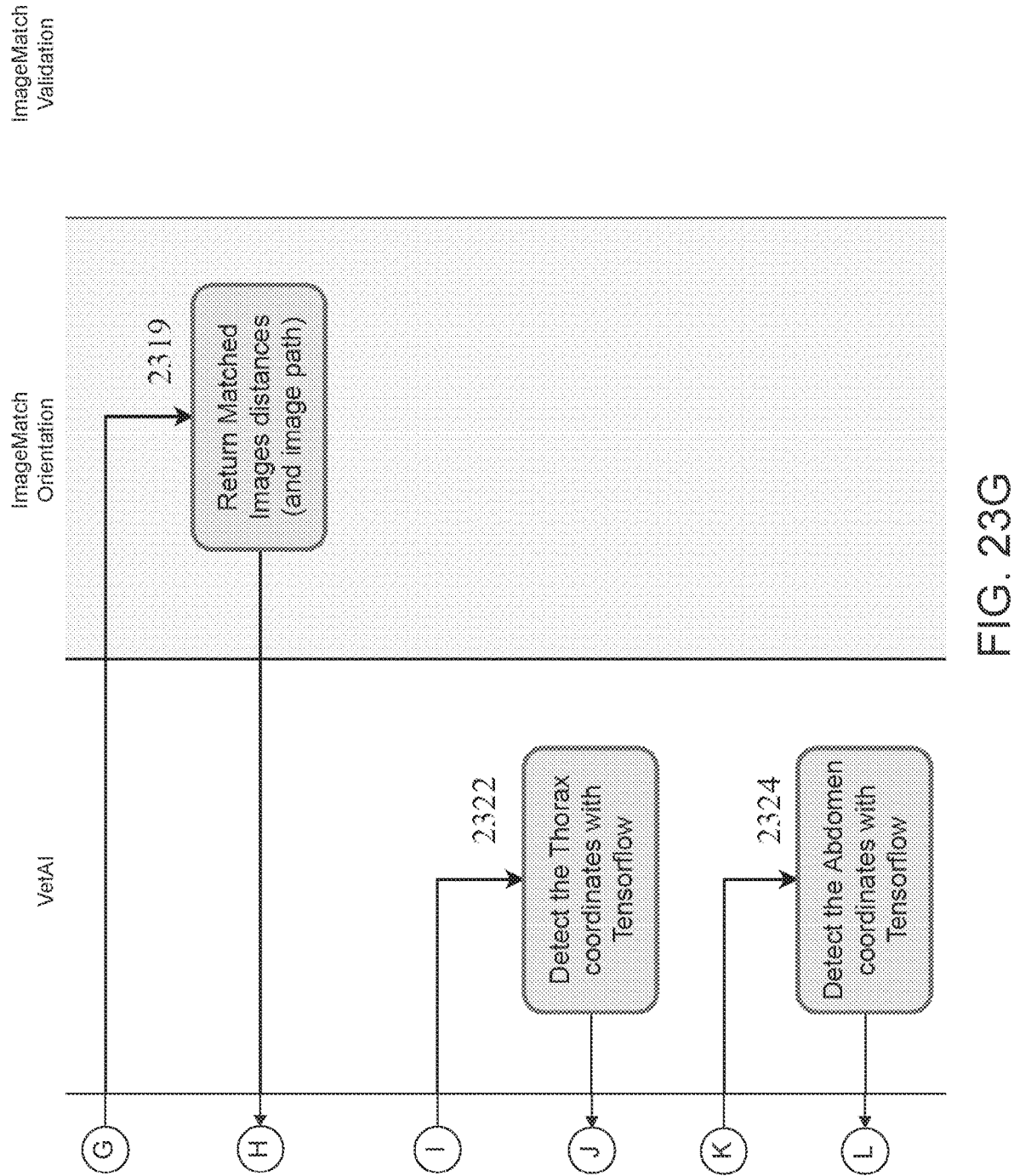
Figure 23H:
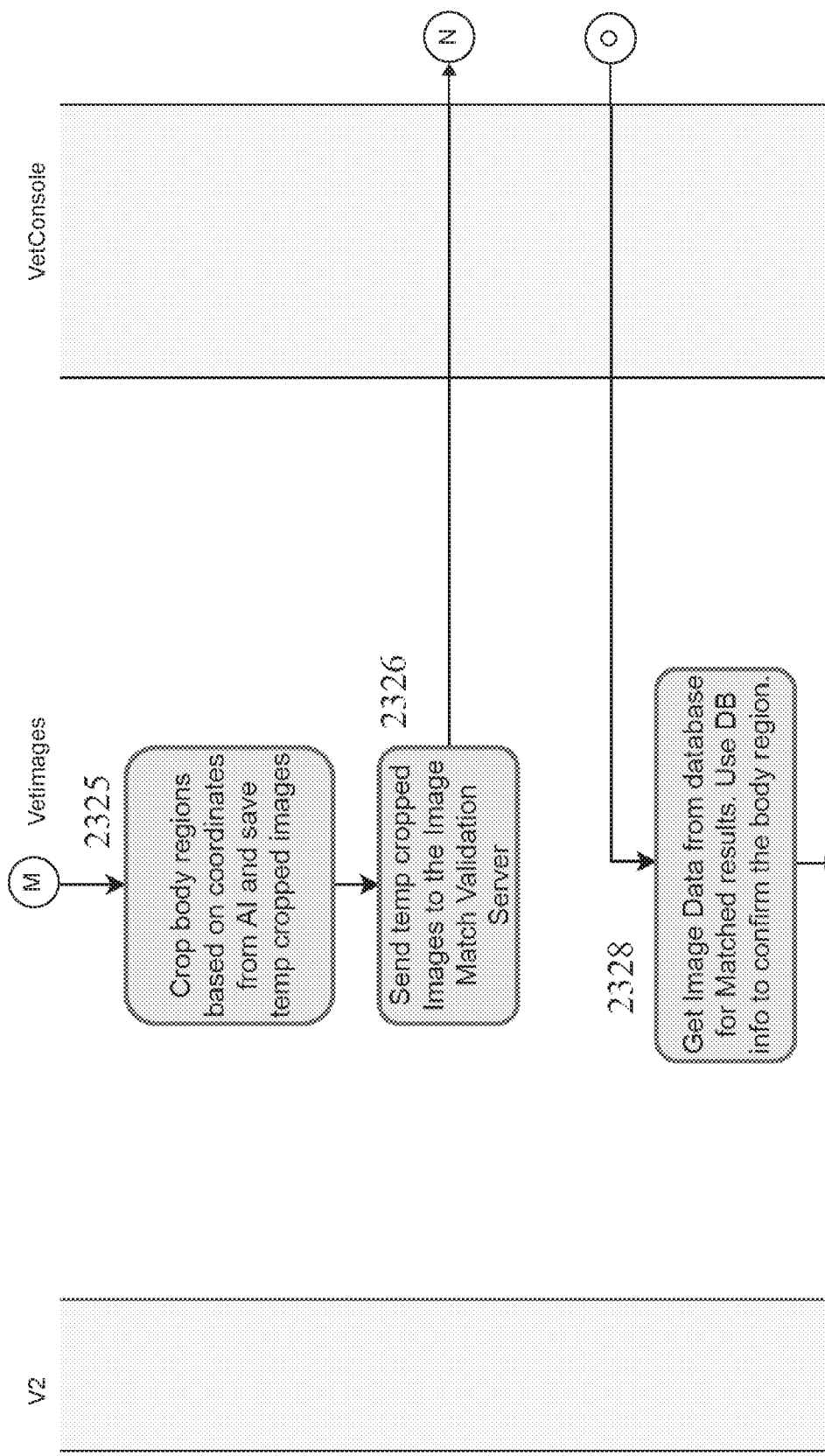
Figure 23:
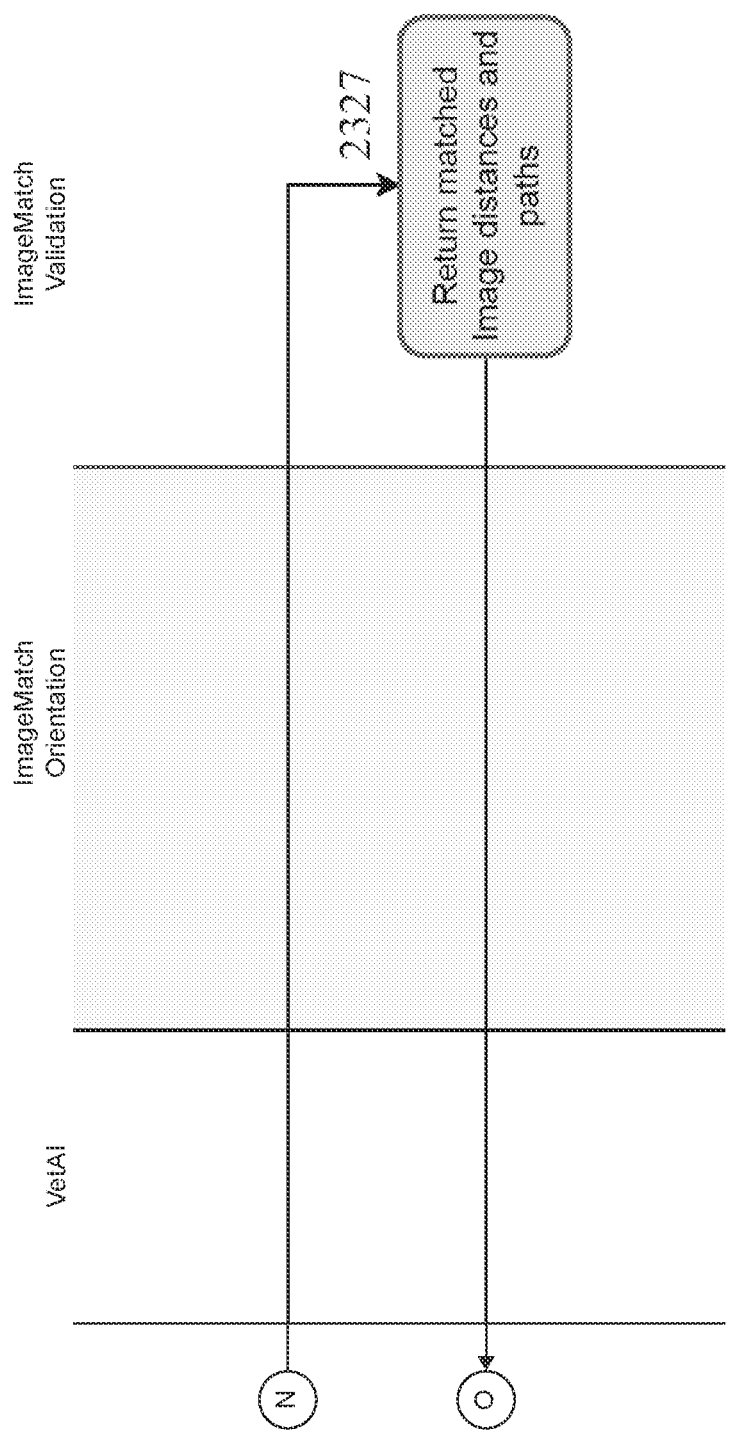
Figure 23J:
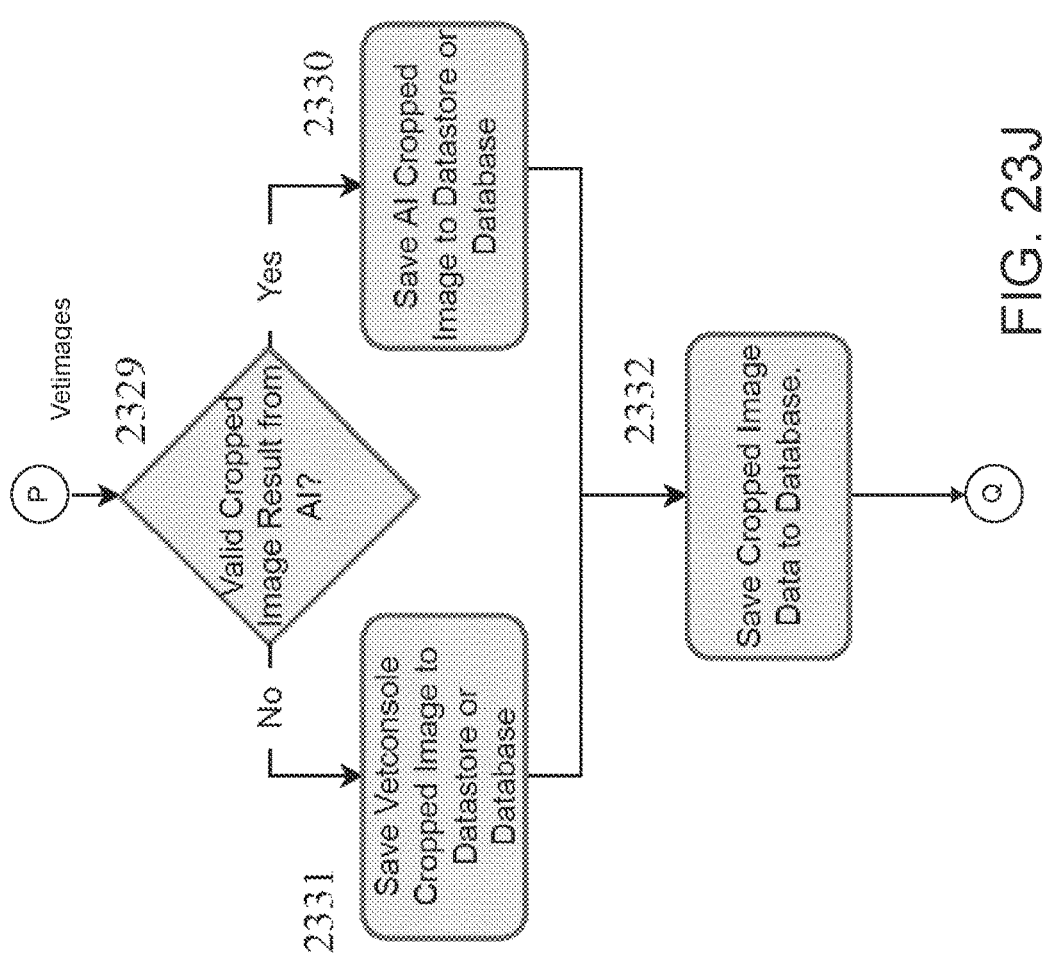
Figure 23K:
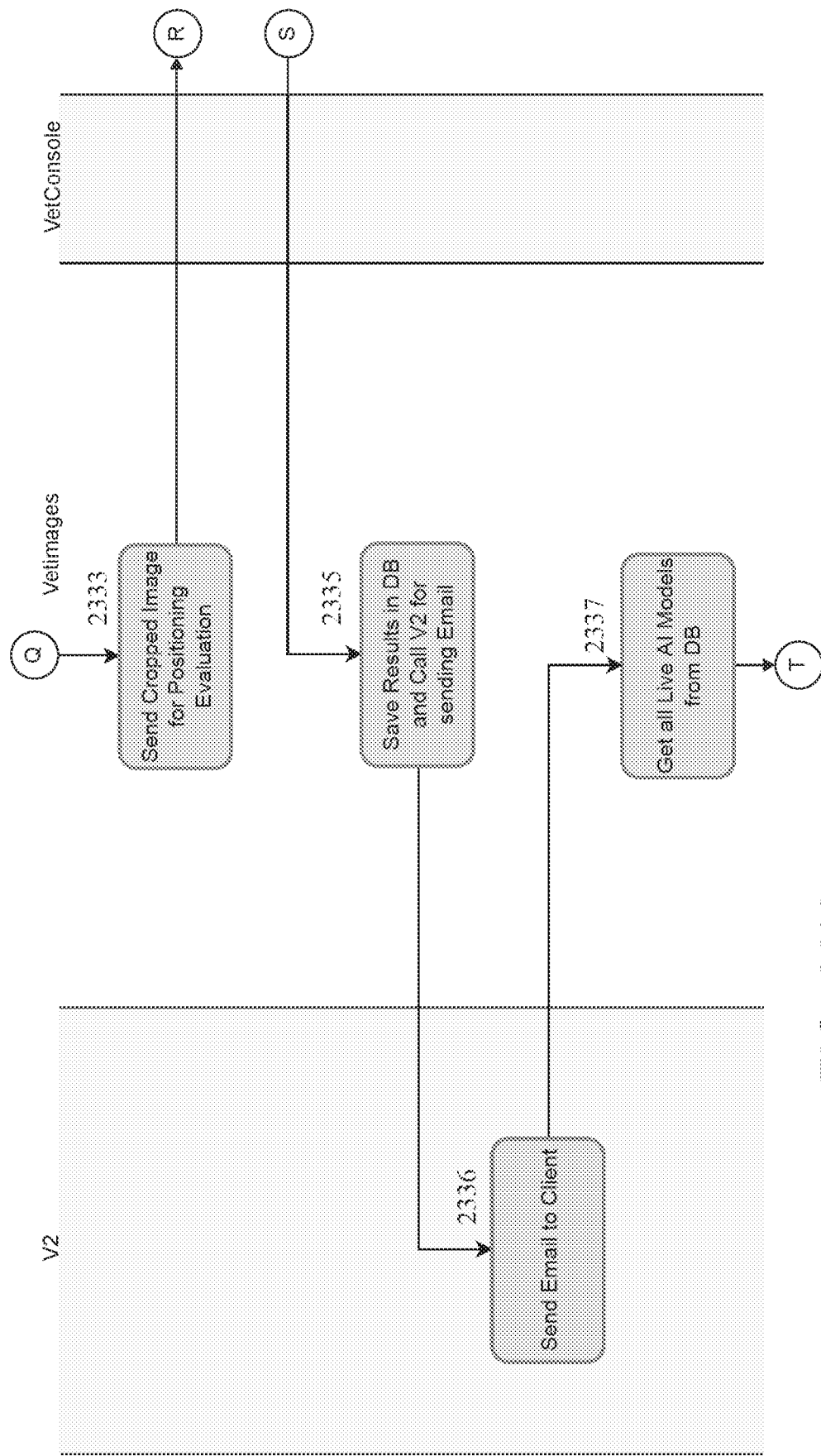
Figure 23L:
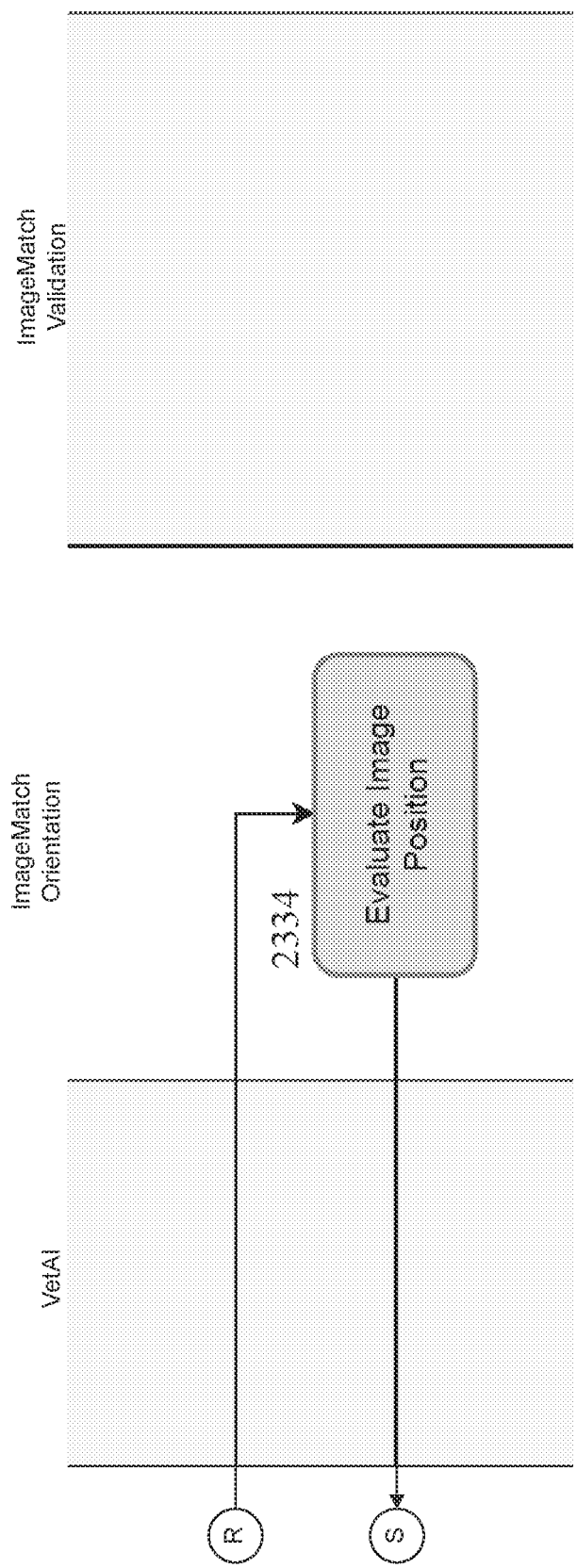
Figure 23M:
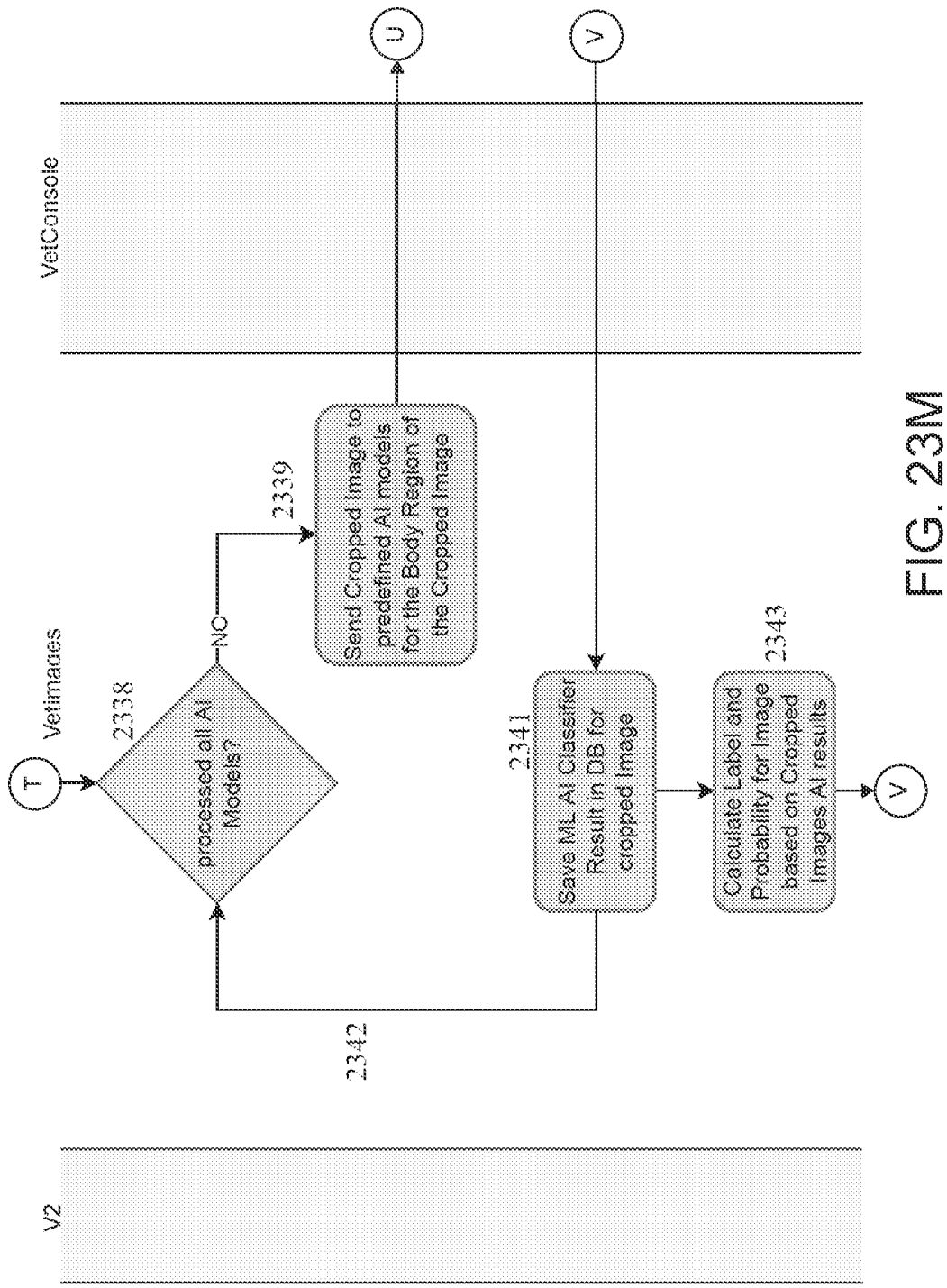
Figure 23N:
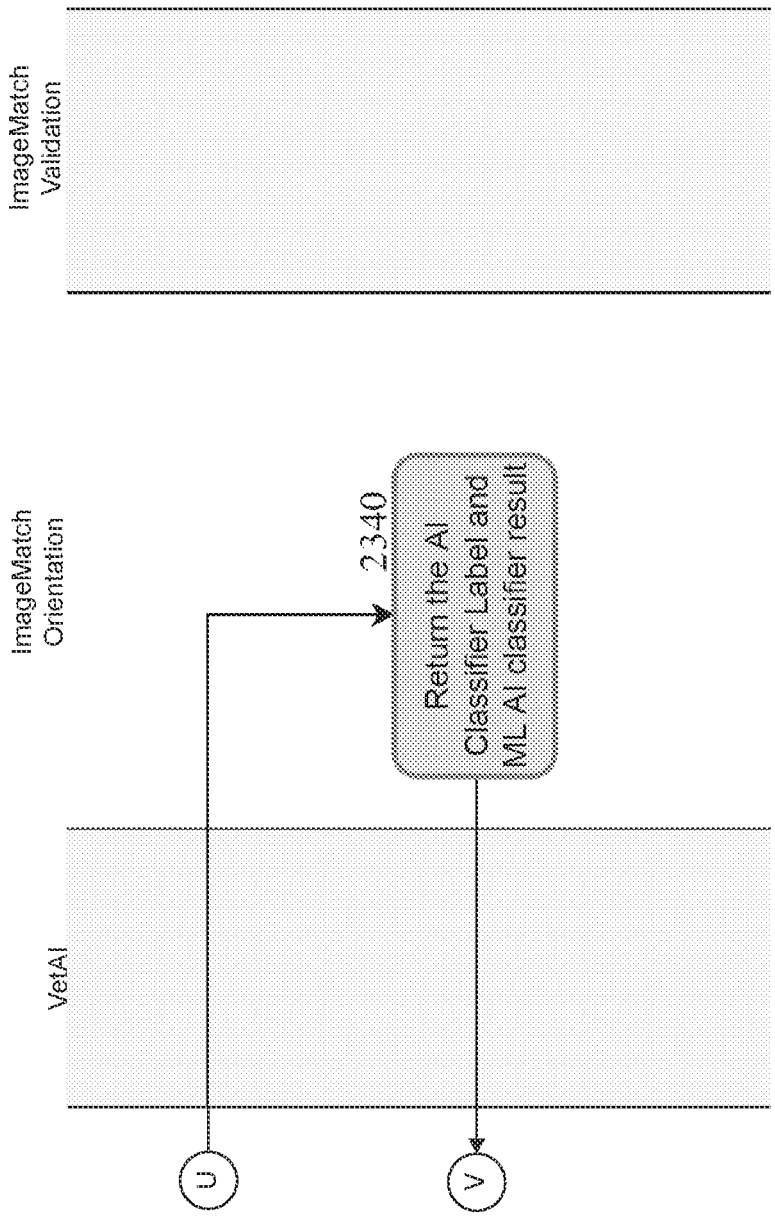
Figure 23O:
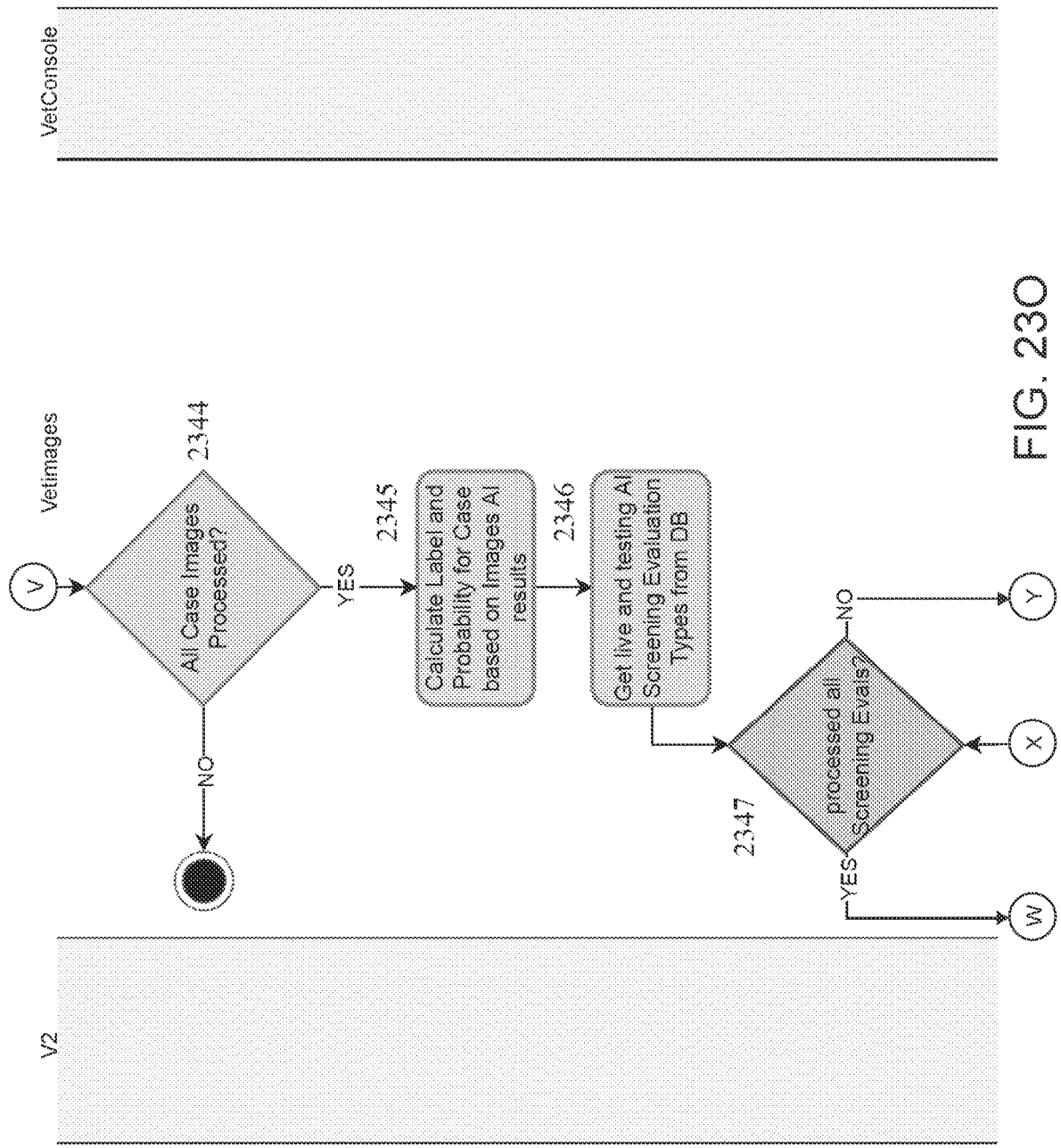
Figure 23P:
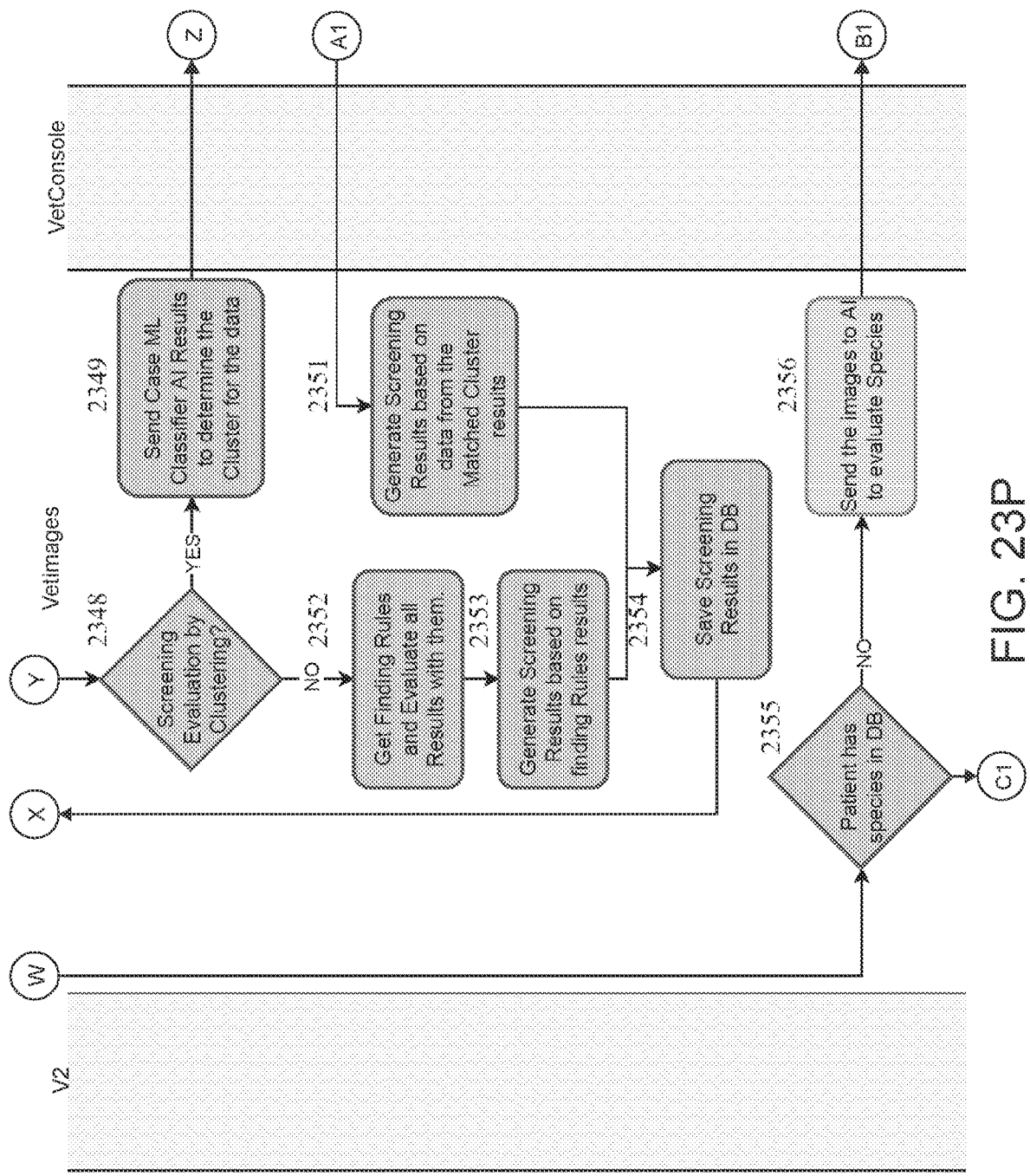
Figure 23R:
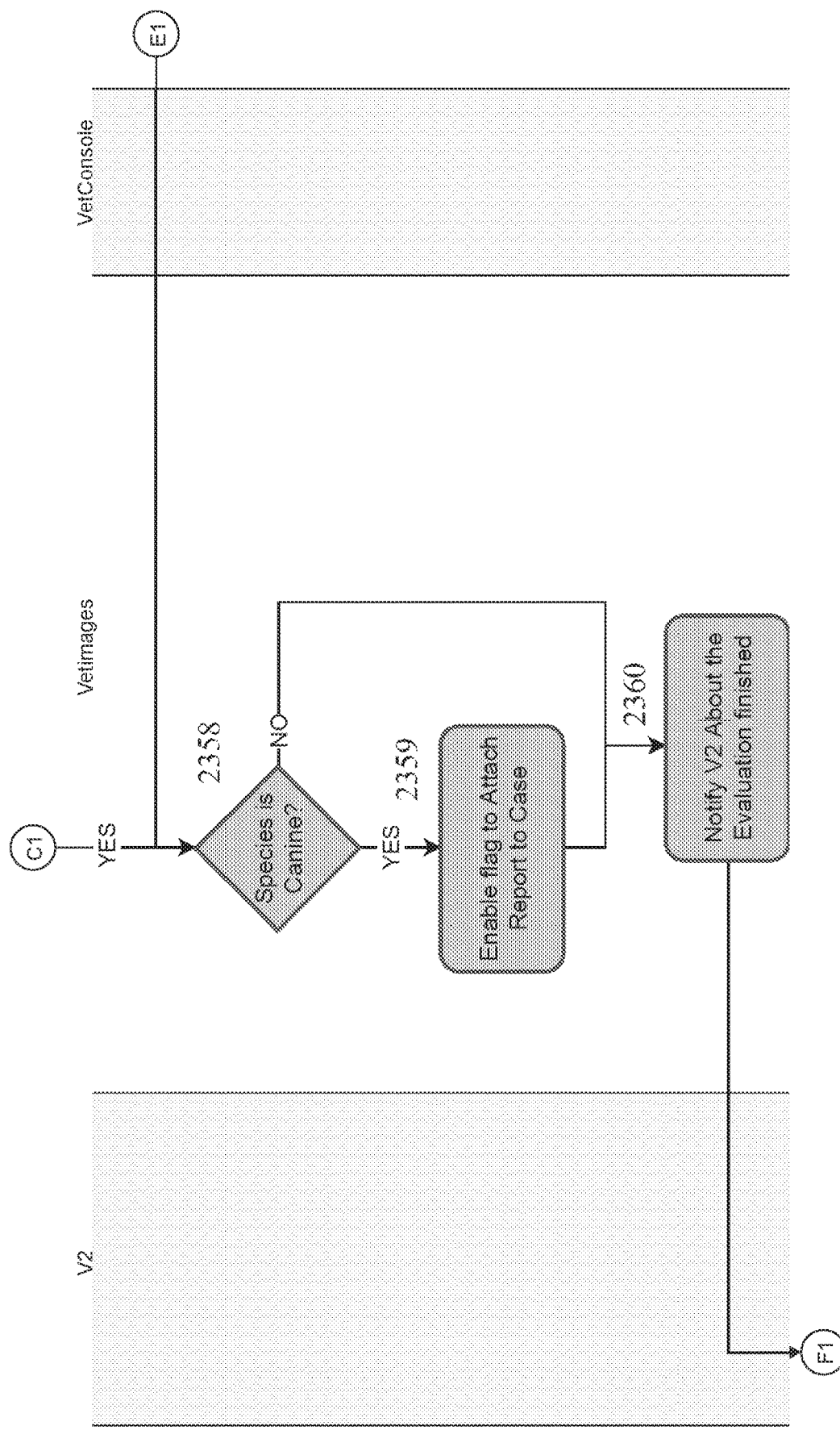
Figure 23S:
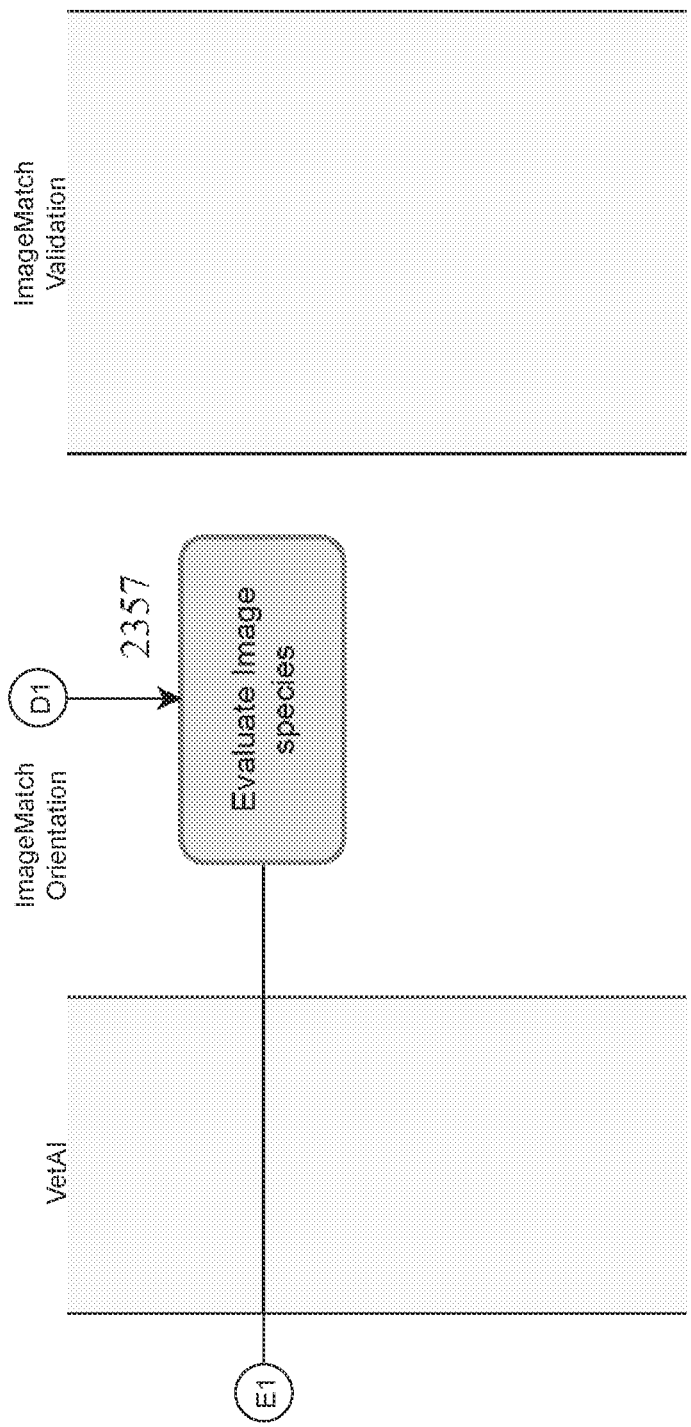
Figure 23T:
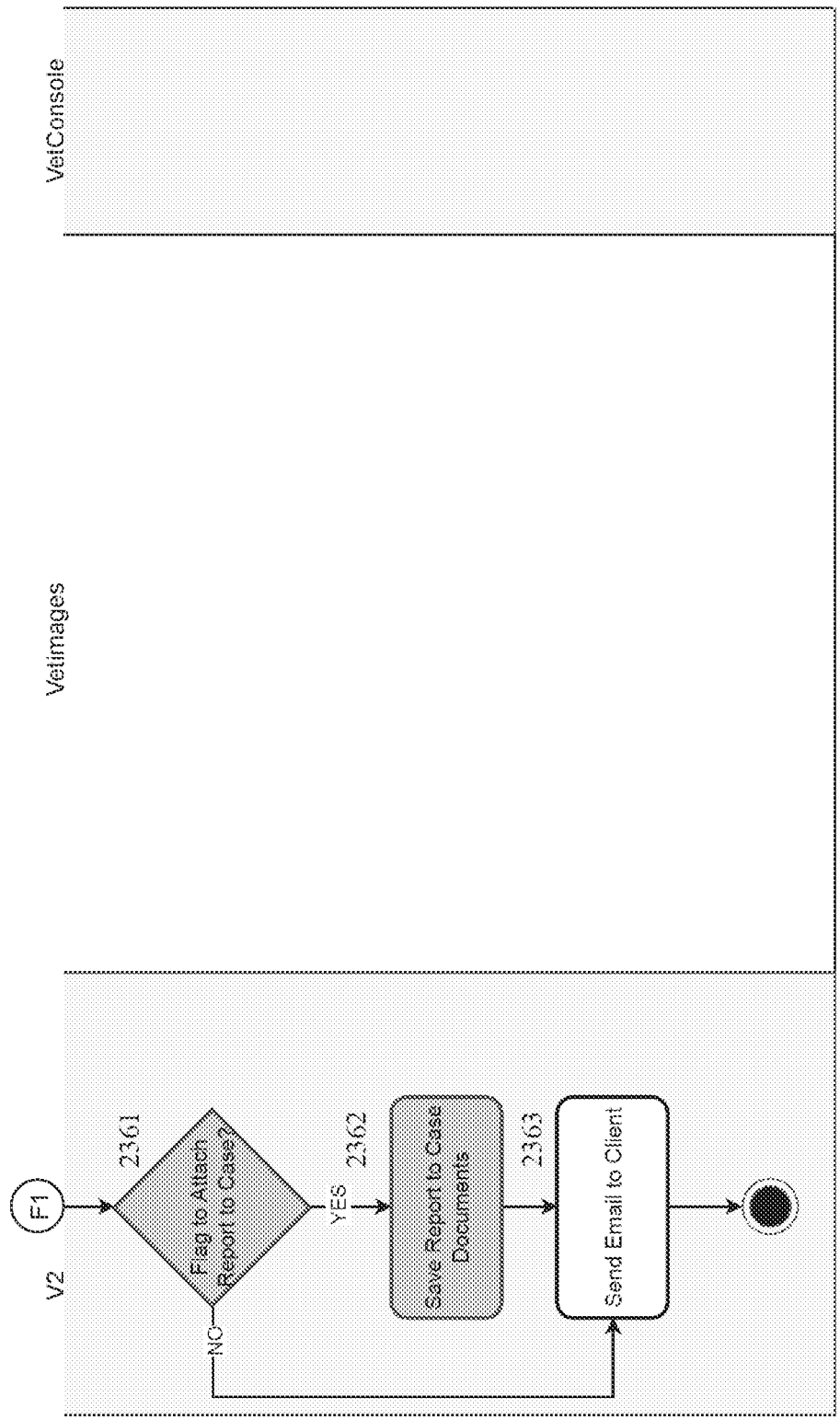

FIG. 23A-FIG. 23T are a series of schematic drawings of Artificial intelligence autocropping and evaluation workflow for an image obtained for a subject. The workflow is classified into six columns based on the platform used to accomplish the task such as, the clinic, the V2 end user application, VetImages web application, VetConsole python scripting application, VetAI machine learning application, ImageMatch orientation python application and ImageMatch validation python application. Further, the tasks are shaded a different shade of grey based on the processor that accomplishes the task, such as sub-image processor, evaluation processor and synthesis processor. The V2 application is an end user application in which a user interacts with the application and uploads the images to be analyzed. The VetImages application processes the images to generate AI result or AI report or evaluation result. The VetConsole is a python scripting app which improves the image quality and processes images in batches. The VetAI is a machine learning application to create AI models and evaluate images which are entered in the system. ImageMatch orientation is a python app which conducts search for correctly oriented images in its database similar to the inputted image. ImageMatch validation is a python app which conducts search for correct classified images in its database similar to the entered image. The sub-image processor accomplishes the tasks 2301-2332 listed in FIG. 23A-FIG. 23J. The evaluation processor conducts the tasks 2333-2346, 2356 and 2357 listed in FIG. 23K-FIG. 23O and a portion of FIG. 23P and FIG. 23S. The synthesis processor performs the tasks 2347-2355 and 2358-2363 listed in FIG. 23O-FIG. 23T and a portion of FIG. 23E.

DETAILED DESCRIPTION

An aspect of invention herein describes a novel system with several stages of analysis, including determining whether the received image includes a particular body region in a particular orientation (lateral view, etc.), cropping the image appropriately, and evaluating the cropped image by comparing the image to targeted AI models. In various embodiments, the newly-received images are pre-processed to automatically identify and label one or more body regions and/or views that are represented in the image without user input or intervention. In some embodiments, the image is cropped automatically to generate one or more sub-images corresponding to the respective body regions/views that were identified. In some embodiments the image and/or sub-images are selectively processed to targeted AI processors which are configured to evaluate the identified body regions/views, excluding the remainder of the AI processors in the system.

In some embodiments, the radiographic image pre-processor 106 additionally or alternatively tags the entire image 102 to identify the body regions and/or views that were identified within the image 102, and then pass the entire image 102 to only those AI processors 104 that correspond to the applied tags. Accordingly, in such embodiments, the AI processors 104 are be responsible for cropping the image 102 to focus on the pertinent regions for further analysis using one or more trained machine learning models or otherwise. In some embodiments, in addition to tagging the image 102 as corresponding to particular body regions/views, the radiographic image pre-processor 106 additionally crops the image 102 to focus primarily on the regions of the image that actually represent portions of the animal and to remove as much of the black border around those regions as possible. In some embodiments, performing such a cropping step facilitates further cropping and/or other processing by the AI processor(s) 104 that are subsequently deployed to evaluate particular body regions/views corresponding to the applied tags.

The radiographic image pre-processor 106 is implemented in any of several ways. In some embodiments, for example, the radiographic image pre-processor 106 employs one or more algorithms for identifying one or more features indicative of particular body regions, and automatically cropping the image 102 to focus on those regions that include such features and/or on those regions that actually represent the animal. In some implementations, such algorithms are implemented, for example, using elements of the OpenCV-Python library. A description of the Open Source Computer Vision ("OpenCV") library, as well as documentation and tutorials concerning the same, is found using the uniform resource locator (URL) for OpenCV. The entire contents of the materials accessible via the URL are incorporated herein by reference. In some embodiments, the radiographic image pre-processor 106 additionally or alternatively employs image matching techniques to compare the image 102 and/or one or more cropped sub-images 108 thereof against a repository of stored images that are known to represent particular views of specific body regions, and the image 102 and/or sub-images 108 are determined to represent the body region/view for which the strongest correlation is found with one or more of the stored images. In some embodiments, an AI processor trained to perform body region/view identification additionally or alternatively is employed within the radiographic image pre-processor 106.

In some embodiments, one or more the AI processors described herein are implemented using the TensorFlow platform. A description of the TensorFlow platform, documentation and tutorials are found using TensorFlow website. The entire contents of the materials accessible via the website are incorporated herein by reference. The TensorFlow platform and methods for building AI processors are fully described in Hope, Tom, et al. *Learning TensorFlow: A Guide to Building Deep Learning Systems*. O'Reilly, 2017 which is hereby incorporated by reference herein in its entirety.

In the example shown in FIG. 3, the pre-processing performed by the radiographic image pre-processor 106 included (1) an optional "general" auto-cropping step (reflected in the first five log entries delineated by the bracket 306) pursuant to which the image 302 was initially cropped to focus primarily on the regions of the image that represent portions of the animal and to remove as much of the black border around those regions as possible, (2) a "classified" auto-cropping step (reflected in log entries six through nine within the bracket 306) pursuant to which an initial effort was made, e.g., using elements of the OpenCV-Python library, to identify particular body regions/views and crop the image 302 to focus on the same, and (3) an "image matching" step (reflected in the final three log entries delineated by the bracket 306) pursuant to which the image 302 and/or one or more cropped sub-images 304*a-b* thereof was compared to a repository of stored images that are known to represent particular views of specific body regions. As indicated by the corresponding time stamps, the general auto-cropping step was observed to be completed in two seconds, the classified auto-cropping step was observed to be completed in three seconds, and the image matching step in nineteen seconds.

As shown by the log entries delineated by the bracket 308*a* in FIG. 3, the time taken by the lateral thorax AI processor 104*a* to determine whether the image 302 included a lateral view of an animal's thorax was four seconds. Similarly, as indicated by the log entries delineated by the bracket 308*b*, the lateral abdomen AI processor 104*c* determined whether the image 302 included a lateral view of the animal's abdomen in four seconds.

Had the system instead needed to process the newly-received image 302 with all of the possible AI processors 104*a-1*, rather than just the two AI processors corresponding to the body parts/views identified by the radiographic image pre-processor 106, the time by the AI processors would have been significantly longer and/or would have consumed significantly more processing resources to complete the analysis. In a system including thirty different AI processors 104, for example, the processing simply to identify pertinent AI models for determining condition(s) of the imaged animal would have been at least one hundred and twenty seconds of processing time by the AI processors 104 (i.e., thirty AI processors at four seconds per processor), and likely much longer when multiple possible orientations of the image are considered by each of the AI processors 104. By employing the radiographic image pre-processor 106, on the other hand, identification of the pertinent AI models was observed to be only eight seconds of processing time of the AI processors 104, plus twenty-four seconds of pre-processing time by the radiographic image pre-processor 106.

It is useful to process radiographic images of animals using artificial intelligence (AI) processors, e.g., trained neural networks, to determine probabilities that the imaged animals have certain medical conditions. Typically, separate AI processors are used to evaluate respective body regions (e.g., thorax, abdomen, shoulder, fore limbs, hind limbs, etc.) and/or particular orientations (e.g., ventral dorsal (VD) view, lateral view, etc.) of each such body region, with each such AI processor determining, for a respective body region and/or orientation, probabilities that particular conditions exist with respect to the body region in question. Each such AI processor may include a large number of trained models to evaluate respective conditions or organs within the imaged region. For example, with respect to a lateral view of an animal's thorax, an AI processor may employ different models to determine probabilities that the animal has certain conditions relating to the lungs, such as perihilar infiltrate, pneumonia, bronchitis, pulmonary nodules, etc.

The detection of a single disease condition, such as presence or absence of pneumonia or pneumothorax, is practiced in radiology AI at the present time. In contrast to single disease detection by current radiology AI, human radiologists analyze the radiographs in a whole-istic approach by evaluate the presence or absence of many conditions simultaneously. A limitation of the current AI process is the necessity to use a separate AI detector for each specific condition. However, a combination of conditions results in the diagnosis of a broader disease. For example, in some cases, one or more diagnostic results obtained from radiographic images are caused by several broader diseases. Determining the broader diseases that are present in the subject's radiograph requires use of supplemental diagnostic results in a process known as differential diagnosis. These supplemental diagnostic results are extracted from blood work, patient history, biopsies, or other tests and processes in addition to radiographic images. The current AI process is focused on single diagnostic results and is unable to identify broader diseases requiring differential diagnosis. A novel AI process which is able to combine multiple diagnostic results to diagnose broader diseases is described herein.

The AI process currently uses limited radiographic images which are directed to specific areas as is typical in radiographic images of human subjects. In contrast, veterinary radiology regularly includes multiple body regions within a single radiograph. A novel AI evaluation process to evaluate all body regions included in the study and providing a broader evaluation expected in veterinary radiology is described herein.

The current conventional workflow for AI reporting of a single disease process is illustrated in FIG. 4. The conventional single condition reporting shown in FIG. 4 is insufficient for differential diagnosis of radiographs. Further, using individualized rules for each combination of evaluation results is inefficient to create reports and is unable to meet reporting standards expected of veterinary radiologists. Even for a single disease process, a determination of the severity of a particular condition e.g. normal, minimal, mild, moderate, and severe results in an exponential number of AI models results templates. The process of creating and choosing a single report template from a collection AI model diagnostic results scales exponentially with the number of AI models. The number of AI models for a single disease process results in 57 different templates for five different severities as illustrated in FIG. 5A-FIG. 5N. Therefore, a manually created report for each combination of AI model diagnostic results does not scale well to a large number of AI models being interpreted together.

Automated System for AI Analysis

Described herein is a novel system that analyzes images of a subject animal, the system including: a receiver to receive an image of the subject; at least one sub-image processor to automatically identify, crop, orient and label at least one body region in the image to obtain a sub-image; at least one artificial intelligence evaluation processor to evaluate the sub-image for presence of at least one condition; at least one synthesis processor to generate an overall result report from at least one sub-image evaluation and, optionally, non-image data; and a device to display the sub-images and an overall synthesized diagnostic result report.

The system provides a substantial advancement in veterinary diagnostic image analysis by (1) automating sub-image extraction using a sub-image processor, a task that typically occurs manually or with user assistance, and (2) by synthesizing a large collection of evaluation results and other non-image datapoints into a concise and cohesive overall report using a synthesis processor.

A case includes a collection of one or more images of a subject animal and may include non-image data points such as, but not limited to, age, sex, location, medical history, and other medical test results. In an embodiment of the system, each image is sent to multiple sub-image processors producing many sub-images of various views of multiple body regions. Each sub-image is processed by multiple evaluation processors, generating a multitude of evaluation results for many different conditions, findings, or other features spanning many body regions. A synthesis processor processes all or a subset of evaluation results and non-image data points to produce an overall synthesized diagnostic result report. In an embodiment of the system, multiple synthesis processors produce multiple synthesized diagnostic result reports from differing subsets of evaluation results and non-image data points. These diagnostic reports are assembled together with ancillary data to create the final overall synthesized diagnostic result report.

In an embodiment of the system, each synthesis processor runs on a subset of sub-images and non-image data points corresponding to a body region, e.g. the thorax or abdomen. Each synthesized diagnostic report includes a body region, as is the typical practice in veterinary radiology. The overall synthesized diagnostic result report includes descriptive data of the subject, e.g. name, age, address, breed, and multiple sections corresponding to the output of each synthesis processor, e.g. a thorax diagnostic result section and an abdomen diagnostic result section.

In an embodiment of the system, the subject is selected from: a mammal, a reptile, a fish, an amphibian, a chordate, and a bird. The mammal is dog, cat, rodent, horse, sheep, cow, goat, camel, alpaca, water buffalo, elephant, and human. The subject is a pet, a farm animal, a high value zoo animal, a wild animal, and a research animal.

The images received by the system are images from a radiology exam such as X-ray (radiographs), magnetic resonance imaging (MRI), magnetic resonance angiography (MRA), computed tomography (CT), fluoroscopy, mammography, nuclear medicine, Positron emission tomography (PET), and ultrasound. In some embodiments, the images are photographs.

In some embodiments of the system, analyzing images of a subject generates and displays an overall synthesized result report in: less than about twenty minutes, less than about 10 minutes, less than about 5 minutes, less than about one minute, less than about 30 seconds, less than about 20 seconds, less than about 15 seconds, less than about 10 seconds, or less than about 5 seconds.

Sub-Image Processor

The sub-image processor orients, crops and labels at least one body region in an image to obtain a sub-image automatically and rapidly. The sub-image processor orients the image by rotating the image into a standard orientation depending on the specific view. The orientation is determined by veterinary radiograph standard hanging protocol. The sub-image processor crops the image by identifying a boundary in the image delineating one or more body regions and creating a sub-image containing image data within the identified boundary.

In some embodiments, the boundary is of a consistent aspect ratio. In alternative embodiments, the boundary is not of a consistent aspect ratio. The sub-image processor labels the sub-image by reporting boundary and/or location of each body region contained within the sub-image. Body regions are for example: thorax, abdomen, spine, forelimb, left shoulder, head, neck, etc. In some embodiments the sub-image processor labels the sub-image according to veterinary radiographic standard body region labels.

The sub-image processor matches the image to a plurality of reference images in at least one of a plurality of libraries to orient, crop and label one or more sub-images. Each of the plurality of libraries include respective plurality of reference images specific or non-specific to an animal species.

The sub-image processor extracts a signature of the image prior to orienting, cropping, and/or labeling the image, thereby allowing rapid matching of the image or sub-image to similar reference images. The sub-image processor processes the image to obtain the sub-image in: less than about twenty minutes, less than 10 minutes, less than about 5 minutes, less than about one minute, less than about 30 seconds, less than about 20 seconds, less than about 15 seconds, less than about 10 seconds, or less than about 5 seconds.

Evaluation Processor

The artificial intelligence evaluation processor assesses a sub-image for a presence or an absence of a condition, finding, or other feature. The evaluation processor reports the probability of presence of a condition, a finding, or a feature.

The evaluation processor diagnoses a medical condition from the sub-image. The evaluation processor assesses the sub-image for a non-medical feature, for example, proper positioning of the subject. The evaluation processor generates instructions for rectifying the positioning of the subject.

Typically, evaluation processor training includes negative control/normal and positive control/abnormal training sets with respect to a condition, finding, or other feature. The positive control/abnormal training set typically includes cases in which presence of the condition, finding, or other feature has been assessed. The negative control/normal training set includes cases in which the absence of the condition, finding or other feature has been assessed and/or the cases are deemed completely normal. In some embodiments, the negative control/normal training set includes cases in which a presence of other conditions, findings, or features distinct from the one of interest have been assessed. Therefore, the evaluation processor is robust.

The evaluation processor processes the sub-image to report the presence of the condition in: less than about twenty minutes, less than about 10 minutes, less than about 5 minutes, less than about one minute, less than about 30 seconds, less than about 20 seconds, less than about 15 seconds, less than about 10 seconds, or less than about 5 seconds.

Synthesis Processor

The synthesis processor receives at least one evaluation from an evaluation processor and generates a comprehensive result report. The synthesis processor may include non-image data points, for example species, breed, age, weight, location, sex, medical test history including blood, urine, and fecal tests, radiology reports, laboratory reports, histology reports, physical exam reports, microbiology reports, or other medical and non-medical tests or results. The subject's case exemplar result includes at least one image, associated evaluation processor results and a collection of zero or more up to date non-image data points.

In an embodiment of the method, the synthesis processor uses the case exemplar result to select a pre-written template to output as an overall result report. The template is customized automatically based on case exemplar result elements to provide a customized overall result report.

The synthesis processor assigns the subject's case exemplar result to a cluster group. The cluster group contains other similar case exemplar results from a reference library of case exemplar results from other subjects. In some cases, the cluster group contains partial case exemplar results, e.g. a result report. The reference library includes case exemplar results with known diseases and conditions from at least one of a plurality of animal species. New case exemplar results are added to the reference library to improve the synthesis processor performance over time. The synthesis processor assigns coordinates representing the location of each case exemplar result within a cluster group.

A single overall result report is assigned to the entire cluster group and the overall result report is assigned to the subject by the synthesis processor. In some embodiments, several overall result reports are assigned to various case exemplar results within the cluster and/or various custom coordinates within the cluster, such as the cluster centroid, with no associated case exemplar result. The coordinates of the subject's case exemplar result are used to calculate a distance to the nearest or non-nearest case exemplar result or custom coordinate that has an associated overall result report, which is then assigned to the subject.

The overall result report or reports are written by expert human evaluators. In an alternative embodiment, the overall result report or reports are generated from existing radiology reports. The existing radiology reports are modified by Natural Language Processing (NLP) to remove content that is not universally applicable, such as names, dates, references to prior studies, etc. to create suitable overall result reports. Statements contained within the overall result report are removed or edited if the statements do not meet a threshold of prevalence within the cluster.

The synthesis processor outputs the assigned overall result report for the subject, thereby identifying and diagnosing the presence of one or more findings, diseases and/or conditions in the subject. Cluster groups are established from a reference library of case exemplar results using a clustering tool selected from: K-means clustering, Mean shift clustering, Density-Based Spatial Clustering, Expectation-Maximization (EM) Clustering, and Agglomerative Hierarchical Clustering.

The synthesis processor processes the case exemplar result to generate an overall result report: less than about 20 minutes, less than about 10 minutes, less than about 9 minutes, less than about 8 minutes, less than about 7 minutes, less than about 6 minutes, less than about 5 minutes, less than about 4 minutes, less than about 3 minutes, less than about 2 minutes, less than about one minute, less than about 30 seconds, less than about 20 seconds, less than about 15 seconds, less than about 10 seconds, or less than about 5 seconds.

Clustering is an AI technique for grouping unlabeled examples by similarities in features of each example. A process for clustering patient studies based on AI processor diagnostic results in addition to non-radiographic and/or non-AI diagnostic results is described herein. The clustering process groups reports that share a similar diagnosis or output report, thereby facilitating a whole-istic detection of conditions or broader diseases in a scalable way.

A novel system and methods with multiple stages of analysis, combining multiple methods of AI predictive image analysis on the radiograph image and report library database and newly received image evaluation to accurately diagnose and report radiology cases are described herein. In various embodiments, the novel system described herein automatically detects the view and regions or regions covered by each radiographic image.

In some embodiments, the system pre-processes the newly received radiographic image 102 to crop, rotate, flip, create sub-images and/or normalize the image exposure using a radiographic image pre-processor 106 prior to AI evaluation. If more than one body region or view are identified, then the system further crops the image 102 to generate one or more sub-images 108a, 108b and 108c corresponding to the respective regions and view that were identified. In some embodiments, the system selectively processes and directs the image and/or sub-images to targeted AI processors configured to evaluate the identified regions/view. The image 108a is directed only to AI processor 104a which is a lateral thorax AI processor. The image 108b is directed only to AI processor 104c which is a lateral abdomen AI processor. The image 108c is directed only to AI processor 104k which is lateral pelvis AI processor. The image is not directed to AI processors which are not targeted or to the remainder of the AI processors in the system. For example, thoracic image FIG. 7 is directed to one or more AI processors for a disease listed in FIG. 6 such as heart failure, pneumonia, bronchitis, interstitial, diseased lung, hypoplastic trachea, cardiomegaly, pulmonary nodules, pleural effusion, gastritis, esophagitis, bronchiectasis, pulmonary hyperinflation, pulmonary vessel enlargement, thoracic lymphadenopathy, etc.

In some embodiments, the AI model processors are binary processors which provide a binary result of normal or abnormal. In various embodiments, the AI model processors provide a normal or abnormal diagnosis with a determination of the severity of a particular condition e.g. normal, minimal, mild, moderate, and severe.

In some embodiments, the newly received AI model processor results are displayed in a user interface. See FIG. 9A-FIG. 9E. The mean AI model processor result for each model is collected from the individual image or sub-images evaluation results and displayed. See FIG. 9A. The user interface displays the individual image or sub-images and the AI model processor result for that image. See FIG. 9B-FIG. 9E. The AI analysis is completed in less than one minute, two minutes, or three minutes.

In some embodiments, one or more clusters are built by the system using AI processor diagnostic results from a library of known radiographic images and corresponding radiology reports database to develop a closest match case or an AI processor "exemplar result" for one or more AI processor results. An exemplar result includes at least one image, the collection of associated evaluation processor results, and a collection of zero or more non-image data points such as age, sex, location, breed, medical test results, etc. The synthesis processor assigns coordinates representing the location of each case exemplar result within a cluster group. Therefore, if two cases have similar exemplar results, then the diagnosis is similar or largely identical and a single overall result report applies to the two cases. In some embodiments, single exemplar result is assigned to an entire cluster and a subject case that is located in the cluster gets assigned the exemplar result. In some embodiments, multiple exemplar results are assigned to the cluster which are either tied to specific coordinates (e.g. the centroid) or specific dataset cases in the cluster. In some embodiments, exemplar results are written by a human or autogenerated from existing radiology reports tied to cases.

In some embodiments, the user specifies various parameters for creating the cluster from the library of known radiographic images and corresponding radiology reports database with a user interface of FIG. 11. The user assigns a name 1101 for the new cluster under "Code". The user selects various parameters to create a cluster. The user chooses a start Case date 1102 and an end Case date 1103 to select the cases. The user chooses a start Case ID (1104) and an end Case ID 1105 to select the cases. The user chooses a maximum number of cases 1106 that are to be included in the cluster. The user chooses species 1107 such as dog, cat, dog or cat, human, avian pet, farm animal, etc. for the cases to be included in the cluster. The user selects a specific diagnostic modality 1108 such as X-ray, CT, MRI, blood analysis, urinalysis, etc. to be included in creating the cluster.

In various embodiments, the user specifies separating the evaluation results into a specific number of clusters. The number of clusters range from a minimum of one cluster to a maximum of clusters limited only by total number of cases entered into the cluster. The system builds one or more clusters using non-radiographic and/or non-AI diagnostic results, such as blood work, patient history, or other tests or processes, in addition to AI processor diagnostic results. The clusters are listed in a numerical form in a comma separated value (CSV) file format as shown in FIG. 12A-Fig. 12B. The CSV file lists the case IDs 1201 of the cases in the cluster. The mean evaluation results 1202 for each binary model for the specific case ID are listed in the CSV file. The cluster label or cluster location 1203 which includes the specific case based on the collection of evaluation results are listed in the CSV file. The CSV files lists the cluster coordinates. The case ID 1204 of the centroid or center of the specific cluster is listed in the CSV file.

In various embodiments, the cluster is represented by a clustering graph. See FIG. 13. The clustering graph is created by dividing the mean evaluation results into multiple different clusters depending on user defined parameters 1102-1108. The various different clusters are represented by a collection of dots plotted on the graph. The clustering graph of FIG. 13 shows 180 clusters of various sizes.

In some embodiments, a user interface shows AI cluster models generated based on user defined parameters 1102-1108. See FIG. 14. A user interface shows screening evaluation configuration in which a user assigns a specific "cluster model" 1502 to a specific "screening evaluation configuration" name 1501. The status 1503 of the screening evaluation configuration provides additional information about the configuration such as whether the configuration is in live, testing, or draft mode. The live mode is for production and the testing or draft mode is for development.

In some embodiments, a user interface describes the details for a specific cluster model 1601 Thorax 97. See FIG. 16A. In some embodiments, the user interface lists the AI evaluation classifier types 1602 included in the cluster. The user interface displays additional parameters used for building the cluster such as the species 1603 specific for the cluster model, the maximum number of cases 1604 with evaluation results, or the start and end dates 1605 for cases used to create the cluster. The user interface provides a link 1606 to the comma separated value (CSV) file showing the cluster in numerical table format. The user interface lists sub-clusters 1608 created from the parameters 1602-1605. The user interface displays the total number of sub-clusters 1609 created for the cluster group. The user interface provides a centroid case ID 1610 for each sub-cluster. The log for building the cluster is provided in the user interface. See FIG. 16B.

In various embodiments, the system utilizes one or more AI processors to evaluate newly received undiagnosed images and obtain newly received evaluation results. The system compares the newly received evaluation results to one or more clusters obtained from the library of known radiographic images and corresponding radiology reports database.

The user imports the newly received AI processor results into an AI Eval tester. See FIG. 17A. The user specifies the screening evaluation type 1702 and the corresponding cluster model 1703.

The system compares the non-radiographic and/or non-AI diagnostic results in addition to the newly received evaluation results to one or more clusters obtained from the library of known radiographic images and corresponding radiology reports database in addition to other available. The system measures the distance between the location of newly received AI processor results and the cluster results and utilizes one or more cluster results to create a radiologist report. In some embodiments, the system chooses to utilize the entire radiologist report or a portion of a radiologist report from the known cluster results depending on the location of the newly received AI processor results relative to the known cluster results. In various embodiments, the system chooses to utilize the entire radiologist report or a portion of the radiologist report from other results in the same cluster. In some embodiments, the system chooses to utilize the entire radiologist report or a portion of the radiologist report from the centroid of the cluster result.

A user interface displays the result of the AI Eval tester. See FIG. 18A. In various embodiments, the diagnosis and conclusory findings 1801 from a radiologist report that is closest to the evaluation results based on previously created cluster results is displayed. In some embodiments, evaluation findings 1802 are selected from radiologist reports in the cluster of the evaluation results and filtered based on the prevalence of a specific sentence in the findings section of the specific cluster. In some embodiments, recommendations 1803 from the radiologist report in the cluster are selected based on prevalence of each sentence or a similar sentence in the recommendations section of this cluster. The user interface displays the radiologist report of the cluster 1804 and the radiologist report of the centroid of the cluster 1805. A user interface allows the user to edit the report by editing the findings section 1809, the conclusion section 1810 or the recommendation section 1811 by adding or removing specific sentences. See FIG. 18D. A radiologist report for the closest match database case is used to generate the radiology report for the newly received radiographic image. The sentences in a radiology report based on the specific cluster results are ranked and listed according to the rank and prevalence. See FIG. 18A and FIG. 18B.

In various embodiments, the system utilizes one or more AI processors to evaluate newly received undiagnosed images and obtain newly received evaluation results. The system compares the newly received evaluation results to one or more clusters obtained from the library of known radiographic images and corresponding radiology reports database.

The system compares the non-radiographic and/or non-AI diagnostic results in addition to the newly received evaluation results to one or more clusters obtained from the library of known radiographic images and corresponding radiology reports database in addition to other available. The system measures the distance between the location of newly received AI processor results and the cluster results and utilizes one or more cluster results to create a radiologist report. In some embodiments, the system chooses to utilize the entire radiologist report or a portion of a radiologist report from the known cluster results depending on the location of the newly received AI processor results relative to the known cluster results. In various embodiments, the system chooses to utilize the entire radiologist report or a portion of the radiologist report from other results in the same cluster. In some embodiments, the system chooses to utilize the entire radiologist report or a portion of the radiologist report from the centroid of the cluster result.

In some embodiments, one or more of the AI processors described herein are implemented using the TensorFlow platform. A description of the TensorFlow platform, as well as documentation and tutorials concerning the same, is found on the TensorFlow website. The entire contents of the materials accessible in the TensorFlow website are incorporated herein by reference in its entirety.

In some embodiments, one or more of the clustering models described herein are implemented using the Plotly platform. A description of the Plotly platform, as well as documentation and tutorials concerning the same, are found on scikit learn website. The entire contents of the materials accessible on the scikit website are incorporated herein by reference in its entirety. The methods for developing AI processors and clustering models using TensorFlow platform and Scikit learn are fully described in the following references: Géron Aurélien. *Hands-on Machine Learning with Scikit-Learn and TensorFlow: Concepts, Tools, and Techniques to Build Intelligent Systems*. O'Reilly, 2019; Hope, Tom, et al. *Learning TensorFlow: A Guide to Building Deep Learning Systems*. O'Reilly, 2017; and Sievert, Carson. *Interactive Web-Based Data Visualization with R, Plotly, and Shiny*. CRC Press, 2020. Each of these references are hereby incorporated by reference herein in its entirety.

Had a radiologist attempted to evaluate each model and create rules based on separate AI processor results being found together, the creation of the rules and reports would be time prohibitive. Additionally, the addition of a single additional AI processor model into this scenario becomes exponentially more difficult as the number of already incorporated AI processor models increases. By employing the novel workflow of AI processor result clustering or "exemplar result" comparison between a new image and a known dataset to create the radiologist report, the issue of manual report building when multiple AI processor results are found is resolved. Report building manually via individual AI processor results and rule creation previously took months and with the novel workflow, only takes minimal time.

In some embodiments of the system, the components used for the AI evaluation are as described in FIG. 21A. In various embodiments of the system, the components used for image match AI processing are as described in FIG. 21B.

In various embodiments of the system, the server architecture for AI radiograph analysis includes pre-processing the radiographic images, analyzing the images using AI diagnostic processors and preparing reports based on clustering results. See FIG. 22B. In some embodiments, various servers are used including NGINX load balancing server 2202, V2 cloud platform 2203, database Microsoft SQL server 2207, and the datastore server 2208.

In various embodiments of the system, a user flags a case for training the AI system. In some embodiments of the system, the user flags cases if the radiology report requires editing because the radiology report is inaccurate, or if the report is inadequate or if the case has a novel diagnosis and hence the radiology report requires new language for diagnosis.

The series of schematics of AI autocropping and evaluation workflow are illustrated in FIG. 23A-FIG. 23T. The user accesses the V2 end user application 2301 to upload the image (in an image format such as DICOM, JPEG, JPG, PNG, etc.) to be analyzed by the system. In some embodiments the image is uploaded 2305 in the VetImages application directly. V2 processes 2302 the image, saves it to Datastore and requests 2303 VetImages to further process the image. VetImages receives the request from V2 and begins 2304 asynchronized processing. VetImages accesses 2307 the image from Datastore and requests 2308 VetConsole to preprocess the image. VetConsole uses OpenCV 2309 to improve the quality of the image and auto-crop 2310 the image. The tasks after accessing the image from Datastore are performed by the Sub-image processor.

The VetConsole sends the auto-cropped image with improved quality to VetImages which analyzes the image and requests VetConsole to classify 2311 thorax, abdomen and pelvis in the image. VetConsole classifies 2312 thorax, abdomen and pelvis in the image and sends coordinates to VetImages. The VetImages sends the image and the coordinates to ImageMatch validation 2313. The ImageMatch validation matches the image and the coordinates with correctly classified images in its database and sends 2314 the matched image distances and paths to VetImages. The VetImages application receives data for matched images and uses the database information to confirm 2315 the body region. The next task is to determine image orientation. The image is rotated and flipped 2317. After each rotation and flip the image is sent 2318 to ImageMatch orientation application to be compared to matched images and to measure distance and image paths between matched images and the newly received image. The ImageMatch orientation application sends results 2319 with distance between the newly received image and the matched images and image paths. The orientation of the newly received image that has the least distance from the matched image is selected 2320 by the VetImages application. The process of checking each orientation and each flip is repeated till the image is rotated 360 degrees and flipped at appropriate angles. In some embodiments, the image with selected orientation is sent to VetAI to detect thorax 2321 and abdomen 2323 and obtain coordinates for cropping the image to obtain sub-images with thorax 2322 and abdomen 2324. The process of obtaining coordinates is coordinated with TensorFlow.

The VetImages application obtains the coordinates from ImageMatch validation and crops 2325 the images according to the coordinates to obtain sub-images. The sub-images are sent 2326 to ImageMatch Validation application for matching. The database images are matched 2327 to the sub-images and the distance between the matched database images and sub-images and the image paths are sent to the VetImages application. The VetImages application receives 2328 the distance and image path data and confirms the body region using the data received from the matched images. The VetImages application analyzes each sub-image to check if each sub-image is valid. If the sub-image(s) is not valid 2331 then the general cropped image from VetConsole application is saved in the database or datastore 2332. If the sub-image(s) is valid 2330 then the sub-image is saved in the database or datastore 2332. The image saved in the database or the datastore is the cropped image used for further processing or analysis. The VetImages application saves the data obtained for the sub-image or the general cropped image from VetConsole in the database 2332.

The following tasks are performed by the evaluation processor. The VetImages application sends the cropped image for positioning evaluation 2333 to the VetAI application. The data received 2334 from the VetAI application by the VetImages application is saved in database 2335 and a signal is sent to V2 application to send an email 2336 to the clinic. The VetImages application accesses 2337 live AI models from database. The cropped image is sent 2339 to appropriate AI models in the VetAI application based on the body region of the cropped image. The appropriate AI models are predetermined for each body region. The VetAI application sends the AI evaluation label and the machine learning (ML) AI evaluation result 2340 to the VetImages application which saves 2341 these data in the database for the cropped image. The VetImages application calculates 2342 the label and the probability for image based on the AI evaluation results for the cropped image. The process of sending 2339 cropped images to obtain the AI evaluation result is reiterated 2342 until the predetermined AI models are processed 2338.

The VetImages application analyzes 2344 if each image from the case is processed to obtain AI evaluation result. If all images from the case are not processed then VetImages returns to process the next image in the case. If all images from the case are processed then VetImages calculates 2345 the label and the probability of the case as a whole based on the label and the probability of each cropped image. The VetImages application then changes 2346 its status to live and screening evaluation types from the database. Upon changing the status of VetImages application to live, the tasks are performed by the synthesis processor. The VetImages application assesses 2347 whether all screening evaluations are completed. If all screening evaluations are not completed then the VetImages application assesses 2348 if the screening evaluation has to be completed by clustering. If the screening evaluation has to be completed by clustering then the AI evaluation results for the processed images is sent 2349 to the VetAI application and the Best match cluster results are sent 2350 to VetImages application which generates and saves the screening results 2351 based on the best match cluster results in the database. If VetImages application determines that the screening evaluation is not to be performed with clustering then the finding rules are accessed 2352 and the AI evaluation results are processed based on the finding rules to obtain and save 2353 screening results in the database. The process of obtaining screening results and saving in the database is reiterated until screening evaluations for all images in the case are completed and a complete result report is obtained 2354.

The VetImages application assesses 2355 if the species of the subject has been identified and saved in the database. If the species has not been identified then the VetAI application evaluates 2357 the species of the subject and sends species evaluation results to VetImages application. The tasks for species evaluation 2356-2357 are performed by the Evaluation processor. In some embodiments, the VetImages application assesses 2358 if the species is canine. If the species is positively identified as canine then the case is flagged 2359 and the evaluation is attached to the result report. The VetImages application notifies 2360 V2 that the evaluation of the case is completed. V2 application assesses 2361 if the case is flagged. The result report is saved 2362 in the case documents if the report is flagged and the result report is emailed 2363 to the client. If the report is not flagged then the result report is emailed 2363 to the client without saving the report to case documents.

Clustering

Clustering is a type of unsupervised learning method. An unsupervised learning method is a method in which references from datasets consisting of input data without labeled responses are drawn. Generally, clustering is used as a process to find meaningful structure, explanatory underlying processes, generative features, and groupings inherent in a set of examples.

Clustering is a task of dividing the population or data points into a number of groups such that the data points in the same groups are similar to other data points in the same group and dissimilar to the data points in other groups. Therefore, clustering is a method of collecting objects into groups on the basis of similarity and dissimilarity between them.

Clustering is an important process as it determines the intrinsic grouping among the unlabeled data. There are no criteria for a good clustering as clustering depends on the user to choose a criterion that is useful to meet the purpose of the user. For example, clusters are based on finding representatives for homogeneous groups (data reduction), finding "natural clusters" and describing their unknown properties ("natural" data types), finding useful and suitable groupings ("useful" data classes) or finding unusual data objects (outlier detection). This algorithm makes assumptions which constitute the similarity of points and each assumption makes different and equally valid clusters.

Clustering Methods:

There are various methods for clustering which are as follows:

Density-based methods: These methods consider the cluster as a dense region having some similarity and differs from the lower dense region of the space. These methods have good accuracy and ability to merge two clusters. Examples of density-based methods are Density-Based Spatial Clustering of Applications with Noise (DBSCAN), Ordering Points to Identify Clustering Structure (OPTICS), etc.

Hierarchical based methods: The clusters formed by this method form a tree-type structure based on the hierarchy. New clusters are formed using the previously formed clusters. The hierarchical based methods are divided into two categories: Agglomerative (bottom up approach) and Divisive (top down approach). Examples of hierarchical based methods are: Clustering Using Representatives (CURE), Balanced Iterative Reducing Clustering, Hierarchies (BIRCH), etc.

Partitioning methods: The partitioning methods divide the objects into k clusters and each partition forms one cluster. This method is used to optimize an objective criterion similarity function. Examples of partitioning methods are:

K-means, Clustering Large Applications based upon Randomized Search (CLARANS), etc.

Grid-based methods: In grid-based method the data space is formulated into a finite number of cells that form a grid-like structure. All the clustering operation performed on these grids are fast and independent of the number of data objects. Examples of grid-based methods are: Statistical Information Grid (STING), wave cluster, CLustering In Quest (CLIQUE), etc.

K-Means Clustering

K-means clustering is one of the unsupervised machine learning algorithms. Typically, unsupervised algorithms make inferences from datasets using only input vectors without referring to known or labelled outcomes. The objective of K-means is to simply group similar data points together and discover underlying patterns. To achieve this objective, K-means looks for a fixed number (k) of clusters in a dataset.

A cluster refers to a collection of data points aggregated together because of certain similarities. A target number k refers to the number of centroids that a user would require in a dataset. A centroid is the imaginary or real location representing the center of the cluster. Every data point is allocated to each of the clusters through reducing the in-cluster sum of squares. The K-means algorithm identifies k number of centroids, and then allocates every data point to the nearest cluster, while keeping the centroids as small as possible.

The 'means' in the K-means refers to averaging of the data which is finding the centroid. To process the learning data, the K-means algorithm in data mining starts with a first group of randomly selected centroids, which are used as the beginning points for every cluster, and then performs iterative (repetitive) calculations to optimize the positions of the centroids. The algorithm halts creating and optimizing clusters when the centroids have stabilized and there are no changes in their values because the clustering has been successful, or the defined number of iterations has been achieved.

The method for K-mean clustering follows a simple method to classify a given data set through a certain number of clusters (assume k clusters) fixed a priori. The k centers or centroids one for each cluster are defined. The next step is to take each point belonging to a given data set and associate it to the nearest center. When no point is pending, the first step is completed and an early group age is performed. The next step is to re-calculate k new centroids as barycenter of the clusters resulting from the previous step. Upon calculating the k new centroids, a new binding is performed between the same data set points and the nearest new center thereby generating a loop. As a result of this loop the k centers change their location step by step until the k centers stop changing their location. The K-means cluster algorithm aims at minimizing an objective function know as squared error function which is calculated by the formula:

$$J(V) = \sum_{i=1}^{c}\sum_{j=1}^{c_i}(\|x_i - v_j\|)^2$$

in which,

'$\|x_i - v_j\|$' is the Euclidean distance between $x_i$ and $v_j$.
'$c_i$' is the number of data points in $i^{th}$ cluster.
'c' is the number of cluster centers.

Algorithmic Steps for K-Means Clustering

The algorithm for K-means clustering is as follows:

In K-means clustering 'c' cluster centers are randomly selected, the distance between each data point and cluster centers is calculated, the data point is assigned to the closest cluster center, the new cluster centers are recalculated using the formula $$v_i = (1/c_i)\sum_{j=1}^{c_i} x_i$$

where, '$c_i$' is the number of data points in $i^{th}$ cluster,
X is $\{x_1, x_2, x_3, \ldots, x_n\}$ the set of data points, and
V is $\{v_1, v_2, \ldots, v_c\}$ the set of centers.

The distance between each data point and newly obtained cluster centers is measured and if a data point is reassigned then the process continues till no data point is reassigned.

AI Application Process Flow

In some embodiments, Digital Imaging and Communications in Medicine (DICOM) images are submitted via LION and transmitted over Hypertext Transfer Protocol Secure (HTTPS) by DICOM ToolKit library (Offis.de DCMTK library) to a V2 platform. The DICOM images are temporarily stored in the V2 platform. In some embodiments a DICOM record is created with limited information and the status is set to zero. In various embodiments, once the DICOM images are available in temporary storage a V2 PHP/Laravel application begins processing the DICOM images through a Cron job.

In some embodiments, Cron job (1) monitors V2 for new DICOM images, obtains the DICOM images from temporary storage, extracts tags, extracts frames (single sub-image or multi sub-images), saves the images and tags in a data store and sets the processing status in a database. In some embodiments, Cron job (1) converts and compresses the DICOM images into a lossless JPG format using the Offis.de library DCMTK and sets the processing status to one. In some embodiments, the Cron job (1) automatically runs every few minutes such as every five minutes, every four minutes, every three minutes, every two minutes or every minute. In some embodiments, the Cron job (1) saves DICOM image metadata to a table called DICOM in a Microsoft SQL server and extracts the images/frames and stores the images/frames in a directory for the image manager. In various embodiments, records are created during processing which contain additional information about the image and the case ID associated with the image. The records contain additional data such as physical exam findings for the subject, study of multiple visits for the subject, series of images obtained during each exam, and hierarchy of the images within the case.

In various embodiments, the DICOM image and metadata are processed by a Vet Images application written in PHP Laravel Framework. V2 makes a REST service request to VetImages to process each image asynchronously. In some embodiments, VetImages responds to V2 immediately to confirm that the request has been received and that the processes for cropping and evaluation of the images will continue in background. Because the images are processed in parallel the overall process is performed at high speed.

In various embodiments, VetImages passes or transfers the image to a module called VetConsole, which is written in Python and uses Computer Vision technology OpenCV to preprocess the image. VetConsole identifies body regions in the image such as thorax, abdomen, pelvis, as a reserve in case the AI Cropping server is unable to classify body region in the image. VetImages rotates and flips the image until a correct orientation is achieved. In some embodiments, VetImages uses image match servers to validate the different angles and projections of the image. In various embodiments, the image match servers are written in Python and Elastic Search to identify image matches. In some embodiments, the image database for the image match servers are carefully selected to return results only if the image is accepted to be in correct orientation and projection.

In various embodiments, upon determining the orientation of the image VetImages sends a REST API request to Keras/TensorFlow server to classify and determine the region of interest of the body regions in the image. The VetImages REST API request is validated using Image Match servers to confirm that the returned regions of the image are classified into body regions such as thorax, abdomen, pelvis, stifles, etc. In some embodiments, if the evaluation result for cropping is invalid, VetConsole cropping result is validated and utilized.

In various embodiments, the AI Evaluation process to generate the AI report is launched if VetImages determines that the image contains a classified and validated body region. In alternative embodiments, if VetImages determines that the image does not contain a classified and validated body region, the cropping image process ends without results and without generation of a report.

In various embodiments, VetImages sends a REST service call to a Keras/TensorFlow with the classified cropped image to AI Evaluation models for diseases hosted on the TensorFlow application servers written in Python/Django. VetImages saves the results of the AI evaluation models for final evaluation and for report generation.

VetImages also directs the thorax cropped images to TensorFlow server to determine if the image is well positioned with respect to the parameters set by the user. VetImages sends the results of the AI evaluation models to V2 Platform to notify the Clinic the results of the positioning evaluation per image.

In some embodiments, VetImages waits while images are being processed in parallel until all images of a case are cropped and evaluated by the TensorFlow server. In some embodiments, upon completing the evaluation of all images of a case, VetImages process all results of the case using rules defined by a specialist to determine the content of the report in a more human readable way. In an alternate embodiment, VetImages uses a Clustering model created by the user to determine the content of the AI report. In some embodiments, the AI report is assembled using previous radiologist reports which are used to build the Cluster Model in VetImages. In some embodiments, clustering is used to classify the case/image using the prediction results from other diagnostic models using scikit-learn.

In some embodiments, upon determining the content of the AI Report using Specialist Rules or Cluster Models, VetImages checks the species of the case. In some embodiments, only if the species of the case is determined by VetImages to be canine, the report is generated and sent to V2 clinic.

In some embodiments, VetImages sends a request to V2 Platform to notify the Clinic that the new AI report has been sent to the Clinic. In some embodiments, the V2 Platform validates the clinic admin user's or users' licenses. In various embodiments, V2 attaches a copy of the report in or to the Case Documents so that the report is accessible from V1 platform if the clinic has a valid license. In some embodiments, V2 sends an email notification to clinic emails, containing a link or links so that the email receiver can conveniently and immediately open the generated reports.

The methods for machine learning, clustering, and programming are fully described in the following references: Shaw, Zed. *Learn Python the Hard Way: A Very Simple Introduction to the Terrifyingly Beautiful World of Computers and Code*. Addison-Wesley, 2017; Ramalho, Luciano. *Fluent Python*. O'Reilly, 2016; Atienza, Rowel. *Advanced Deep Learning with TensorFlow 2 and Keras: Apply DL, GANs, VAEs, Deep RL, Unsupervised Learning, Object Detection and Segmentation, and More*. Packt, 2020; Vincent, William S. *Django for Professionals: Production Websites with Python & Django*. Still River Press, 2020; Bradski, Gary R., and Adrian Kaehler. *Learning OpenCV*. O'Reilly, 2011; Battiti, Roberto, and Mauro Brunato. *The LION Way: Machine Learning plus Intelligent Optimization*, Version 2.0, April 2015. LIONlab Trento University, 2015; Pianykh, Oleg S. *Digital Imaging and Communications in Medicine (DICOM) a Practical Introduction and Survival Guide*. Springer Berlin Heidelberg, 2012; Busuioc, Alexandru. *The PHP Workshop: a New, Interactive Approach to Learning PHP*. Packt Publishing, Limited, 2019; Stauffer, Matt. *Laravel—Up and Running: a Framework for Building Modern PHP Apps*. O'Reilly Media, Incorporated, 2019; Kassambara, Alboukadel. *Practical Guide to Cluster Analysis in R: Unsupervised Machine Learning*. STHDA, 2017; and Wu, Junjie. *Advances in K-Means Clustering: A Data Mining Thinking*. Springer, 2012. Each of these references are hereby incorporated by reference herein in its entirety.

It is understood that any feature described in relation to any one of the embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention now having been fully described, it is further exemplified by the following claims. Those skilled in the art will recognize or be able to ascertain using no more than routine experimentation, numerous equivalents to the specific methods described herein. Such equivalents are within the scope of the present invention and claims. The contents of all references including issued patents and published patent applications cited in this application are hereby incorporated by reference in their entirety.

What is claimed is:

1. A method for identifying and diagnosing a presence of a disease or a condition in at least one image of a subject, the method comprising:
    classifying the image to at least one body region of a plurality of body regions, labelling and orientating the image using a sub-image processor to obtain a classified, labeled and oriented sub-image based on the body region, the body region defining a veterinary species;
    directing the sub-image to at least one artificial intelligence (AI) evaluation processor based on the body region to obtain an evaluation result, and comparing the evaluation result to a database having a plurality of dataset clusters computed based on previous evaluation results and matched written templates corresponding to the classified image, or at least one dataset cluster, to obtain at least one cluster result;

measuring the distance between the cluster result and the evaluation result to obtain at least one cluster diagnosis using a synthesis processor; and assembling the cluster diagnosis to obtain a report thereby identifying and diagnosing the presence of the disease or the condition in the subject.

2. The method according to claim 1 further comprising prior to classifying, obtaining at least one image or one data point of the subject.

3. The method according to claim 1 further comprising prior to comparing, compiling the dataset cluster using a clustering tool selected from: K-means clustering, Mean shift clustering, Density-Based Spatial Clustering, Expectation-Maximization (EM) Clustering, and Agglomerative Hierarchical Clustering.

4. The method according to claim 3 compiling further comprises obtaining, processing, evaluating, and constructing a library of a plurality of identified and diagnosed dataset and corresponding medical reports selected from: radiology reports, laboratory reports, histology reports, physical exam reports, and microbiology reports, with a plurality of known diseases or conditions.

5. The method according to claim 4, processing further comprises classifying the plurality of identified and diagnosed dataset images to the body regions to obtain a plurality of classified dataset images, and orienting and cropping the plurality of classified dataset images to obtain a plurality of oriented, cropped and labeled dataset sub-images.

6. The method according to claim 5, evaluating further comprises directing the plurality of oriented, cropped and labeled dataset sub-images and corresponding medical reports to at least one AI processor to obtain at least one diagnosed AI processor result.

7. The method according to claim 6 directing further comprises classifying the plurality of oriented, cropped and labeled dataset sub-images and corresponding medical reports with at least one variable selected from: age, species, breed, weight, sex, and location.

8. The method according to claim 7, constructing the library of the plurality of identified and diagnosed dataset images further comprises creating at least one cluster of the diagnosed AI processor result to obtain at least one AI processor exemplar result and thereby compiling the dataset cluster.

9. The method according to claim 8 further comprising assigning at least one cluster diagnosis to the cluster of the diagnosed AI processor result.

10. The method according to claim 9, assigning cluster diagnosis further comprises adding reports within the cluster and/or additional information written by an evaluator.

11. The method according to claim 1, measuring further comprises determining a distance between the cluster result and at least one selected from: the evaluation result, the dataset cluster, and a centroid of the cluster result.

12. The method according to claim 11 further comprises selecting a result from: a case within the cluster that has the nearest match, a result from another case in the cluster, and a centroid case.

13. The method according to claim 12 selecting further comprises adding result information of the cluster result by an evaluator to the report generated from the cluster.

14. The method according to claim 11 further comprising editing the report by removing a portion of the report of the cluster diagnosis which is less than a threshold of prevalence in a plurality of reports in the cluster.

15. The method according to claim 14, wherein the threshold of prevalence designated by an evaluator, is selected to be less than 100% and more than 0%.

16. The method according to claim 14 wherein the threshold of prevalence designated by an evaluator, is selected to be less than about 80%.

17. The method according to claim 1, rapidly processing the evaluation result by a diagnostic AI processor to obtain the report.

18. The method according to claim 17, the diagnostic AI processor processing the image to obtain the report in: less than ten minutes.

19. The method according to claim 4, the library of identified and diagnosed dataset images with known diseases and conditions are categorized to at least one of a plurality of animal species.

20. The method according to claim 9 further comprising identifying the diagnosed AI processor result with an identification tag.

21. The method according to claim 3 further comprising selecting and adding the image and/or a medical result of the subject to the dataset cluster.

22. A system for diagnosing a presence of a disease or a condition in an image and/or a medical result, of a subject, the system comprising:

a receiver to receive an image and/or the medical result of the subject; at least one processor to automatically classify the image to at least one body region of a plurality of body regions, run an image identification and processing algorithm to identify, crop, orient and label at least one body region in the image to obtain a sub-image, the body region defining a veterinary species;

a plurality of artificial intelligence processors selected based on the body region to evaluate the sub-image and/or the medical result and obtain an evaluation result;

a database having a plurality of dataset clusters computed based on previous evaluation results and matched written templates; and at least one diagnostic artificial intelligence processor to automatically run a cluster algorithm to compare the evaluation result to the database to obtain a cluster result and measure a distance between the cluster result and a previously created cluster result from a specific dataset to obtain a cluster diagnosis, and assemble a report.

23. The system according to claim 22, the diagnostic AI processor automatically rapidly processes the image, and/or the medical result to generate a report.

24. The system according to claim 23, the diagnostic AI processor processes the image and/or the medical result to obtain the report in: less than ten minutes.

25. The system according to claim 22 further comprises a device to display the generated report.

26. A method for diagnosing a presence of a disease or a condition in at least one image of a subject, the method comprising:

classifying the image to at least one body region of a plurality of body regions, labelling, cropping, and orientating the image to obtain at least one classified, labeled, cropped, and oriented sub-image based on the body region, the body region defining a veterinary species;

directing the sub-image to at least one artificial intelligence (AI) processor based on the body region for processing and obtaining an evaluation result, and comparing the evaluation result to a database library having a plurality of dataset clusters computed based on previous evaluation results and matched written templates corresponding to the classified image, or at least one dataset cluster, to obtain at least one cluster result;

measuring the distance between the cluster result and the evaluation result to obtain at least one cluster diagnosis; and assembling the cluster diagnosis and the matched written templates to obtain a report and displaying the report to a radiologist thereby identifying and diagnosing the presence of the disease or the condition in the subject.

27. The method according to claim 26 further comprising after displaying, analyzing the report and confirming the presence of the disease or the condition.

28. The method according to claim 27 further comprising editing the written templates.

29. The method according to claim 26, wherein the method of obtaining the report has a process time: less than about 5 minutes, less than about 2 minutes, or less than about 1 minute.

30. The method according to claim 26, wherein the method of obtaining the report has a process time: less than about 10 minutes, less than about 7 minutes, or less than about 6 minutes.

31. The method according to claim 26, processing the sub-image further comprises training the AI processor for diagnosing the presence of the disease or the condition in the image of the subject.

32. The method according to claim 31, training the AI processor further comprises:

communicating a library of training images to the AI processor;

choosing a training image having the disease or the condition from the library of training images; and comparing the training image to the library of training images thereby training the AI processor.

33. The method according to claim 32, the library of training images comprises positive control training images and negative control training images.

34. The method according to claim 33, the positive control training images have the disease or the condition of the training image.

35. The method according to claim 33, the negative control training images do not have the disease or the condition of the training image.

36. The method according to claim 32, the library of training images further comprises at least one of medical data, metadata, and auxiliary data.

* * * * *